US011713449B2

(12) United States Patent
Lock et al.

(10) Patent No.: US 11,713,449 B2
(45) Date of Patent: *Aug. 1, 2023

(54) SCALABLE PURIFICATION METHOD FOR AAVRH10

(71) Applicant: The Trustees of the University of Pennsylvania, Philadelphia, PA (US)

(72) Inventors: Martin Lock, Southampton, PA (US); Mauricio Alvira, Philadelphia, PA (US)

(73) Assignee: Ths Trustees of the University of Pennsylvania, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/236,448

(22) Filed: Apr. 21, 2021

(65) Prior Publication Data
US 2021/0238560 A1 Aug. 5, 2021

Related U.S. Application Data

(63) Continuation of application No. 16/060,404, filed as application No. PCT/US2016/066013 on Dec. 9, 2016, now Pat. No. 11,028,372.

(60) Provisional application No. 62/322,055, filed on Apr. 13, 2016, provisional application No. 62/266,347, filed on Dec. 11, 2015.

(51) Int. Cl.
| C12N 7/02 | (2006.01) |
| C12N 7/00 | (2006.01) |
| B01D 15/38 | (2006.01) |
| B01J 20/281 | (2006.01) |
| C12N 15/864 | (2006.01) |
| G01N 21/33 | (2006.01) |
| B01J 41/05 | (2017.01) |
| B01D 15/16 | (2006.01) |
| B01D 15/36 | (2006.01) |
| B01J 41/20 | (2006.01) |

(52) U.S. Cl.
CPC ............ *C12N 7/02* (2013.01); *B01D 15/3804* (2013.01); *B01J 20/281* (2013.01); *C12N 7/00* (2013.01); *C12N 15/8645* (2013.01); *G01N 21/33* (2013.01); *B01D 15/166* (2013.01); *B01D 15/363* (2013.01); *B01J 41/05* (2017.01); *B01J 41/20* (2013.01); *C12N 2750/14143* (2013.01); *C12N 2750/14151* (2013.01)

(58) Field of Classification Search
CPC ........ C12N 7/02; C12N 7/00; C12N 15/8645; C12N 2750/14143; C12N 2750/14151; B01D 15/3804; B01D 15/166; B01D 15/363; B01J 20/281; B01J 41/05; B01J 41/20; G01N 21/33
See application file for complete search history.

(56) References Cited

U.S. PATENT DOCUMENTS

| 5,658,785 | A | 8/1997 | Johnson |
| 6,566,118 | B1 | 5/2003 | Atkinson et al. |
| 6,723,551 | B2 | 4/2004 | Kotin et al. |
| 7,906,111 | B2 | 3/2011 | Wilson et al. |
| 2004/0110266 | A1 | 6/2004 | Chiorini et al. |
| 2005/0024467 | A1 | 2/2005 | Silverbrook |
| 2013/0045186 | A1 | 2/2013 | Gao et al. |
| 2014/0044794 | A1 | 2/2014 | Okada et al. |

FOREIGN PATENT DOCUMENTS

| EP | 3054007 | 2/2015 |
| JP | 2007/117003 A | 5/2007 |
| WO | WO-1999/011764 | 3/1999 |
| WO | WO-1999/015685 | 4/1999 |
| WO | WO-2004/113494 | 12/2004 |
| WO | WO-2005/033321 | 4/2005 |
| WO | WO-2007/127264 | 11/2007 |
| WO | WO-2009/088786 | 7/2009 |
| WO | WO-2009/108274 | 9/2009 |
| WO | WO-2011/094198 | 8/2011 |
| WO | WO-2012/112832 | 8/2012 |
| WO | WO-2014/125101 | 8/2014 |
| WO | WO-2016/128408 | 8/2016 |
| WO | WO-2016/200543 | 12/2016 |
| WO | WO 2019/212921 | 11/2019 |
| WO | WO2019/241535 A2 | 12/2019 |

OTHER PUBLICATIONS

Adachi et al., Drawing a high-resolution functional map of adeno-associated virus capsid by massively parallel sequencing, Nat Commun, vol. 5:3075, Jan. 2014.
Allay, J. A., et al., Good Manufacturing Practice Production of Self-Complementary Serotype 8 Adeno-Associated Viral Vector for a Hemophilia B Clinical Trial, Human gene Therapy, May 2011, 22:595-604, epub Mar. 17, 2011.
Brument et al., A Versatile and Scalable Two-Step Ion-Exchange Chromatography Process for the Purification of Recombinant Adeno-associated Virus Serotypes–2 and –5, Mol Ther, vol. 6(5):678-686, Nov. 2002.
Clement et al., Large-scale adeno-associated viral vector production using a herpesvirus-based system enables manufacturing for clinical studies, Hum Gene Therapy, vol. 20(8):796-806, Aug. 2009.
Davidoff et al., Purification of recombinant adeno-associated virus type 8 vectors by ion exchange chromatography generates clinical grade vector stock, J Virol Methods, vol. 121(2):209-215, Nov. 2004 (ePub Aug. 2004).

(Continued)

Primary Examiner — Rachel B Gill
(74) Attorney, Agent, or Firm — Howson & Howson; Cathy A. Kodroff

(57) ABSTRACT

A two-step chromatography purification scheme is described which selectively captures and isolates the genome-containing rAAV vector particles from the clarified, concentrated supernatant of a rAAV production cell culture. The process utilizes an affinity capture method performed at a high salt concentration followed by an anion exchange resin method performed at high pH to provide rAAV vector particles which are substantially free of rAAV intermediates.

24 Claims, 17 Drawing Sheets
Specification includes a Sequence Listing.

(56) References Cited

OTHER PUBLICATIONS

Gao et al., Adeno-associated viruses undergo substantial evolution in primates during natural infections, Proc. Natl. Acad. Sci. U.S.A., vol. 100 (10):6081-6086, May 2003 (ePub Apr. 2003).
GenBank Accession No. AAB95452, capsid protein VP1 [Adeno-associated virus 3B], Jan. 1998.
GenBank Accession No. AAO88201, capsid protein [Non-human primate Adeno-associated virus], May 2003.
GenBank Accession No. AAS99264, capsid protein VP1 [Adeno-associated virus 9], Jun. 2004.
GenBank Accession No. AAS99285, capsid protein VP1 [Adeno-associated virus], Jun. 2004.
GenBank Accession No. ACB55316, capsid protein VP1, partial (endogenous virus) [Adeno-associated virus], Jul. 2016.
GenBank Accession No. NP_043941, capsid protein [Adeno-associated virus—3], Aug. 2018.
GenBank Accession No. NP_049542, capsid protein [Adeno-associated virus—1], Aug. 2018.
GenBank Accession No. YP_068409, capsid protein [Adeno-associated virus—5], Aug. 2018.
GenBank Accession No. YP_077180, capsid protein [Adeno-associated virus—8], Aug. 2018.
GenBank Accession No. YP_680426, major coat protein VP1 [Adeno-associated virus—2], Aug. 2018.
Grimm et al., Titration of AAV-2 particles via a novel capsid ELISA: packaging of genomes can limit production of recombinant AAV-2, Gene Therapy, vol. 6(7):1322-1330, Jul. 1999.
Gurda et al., Capsid antibodies to different adeno-associated virus serotypes bind common regions, Journal of Virology, vol. 87(16):9111-9124, Aug. 2013 (ePub Jun. 2013).
Gurda et al., Mapping a neutralizing epitope onto the capsid of adeno-associated virus serotype 8, Journal of Virology, vol. 86(15):7739-7751, Aug. 2012 (ePub May 2012).
Harbison et al., Examining the cross-reactivity and neutralization mechanisms of a panel of mAbs against adeno-associated virus serotypes 1 and 5, Journal of General Virology, vol. 93(Pt 2):347-355, Feb. 2012 (ePub Nov. 2011).
Hellström et al., Cellular tropism and transduction properties of seven adeno-associated viral vector serotypes in adult retina after intravitreal injection, Gene Ther, vol. 16(4):521-532, Apr. 2009 (ePub Dec. 2008).
Kaludov et al., Scalable purification of adeno-associated virus type 2, 4, or 5 using ion-exchange chromatography, Hum. Gene Therapy, vol. 13(10):1235-1243, Jul. 2002.
Kotin et al., Large-scale recombinant adeno-associated virus production, Hu Mol Genet, vol. 20(1):R2-R6, Apr. 2011.
Lock et al., Absolute determination of single-stranded and self-complementary adeno-associated viral vector genome titers by droplet digital PCR, Hu Gene Therapy Methods, vol. 25(2):115-25, Apr. 2014 (ePub Feb. 2014).
Lock et al., Analysis of Particle Content of Recombinant Adeno-Associated Virus Serotype 8 Vectors by Ion-Exchange Chromatography, Human Gene Therapy Methods, vol. 23(1):56-64, Feb. 2012.
Lock et al., Rapid, Simple, and Versatile Manufacturing of Recombinant Adeno-Associated Viral Vectors at Scale, Hum Gene Ther, vol. 21(1):1259-1271, Oct. 2010.
Mietzsch et al., OneBac: platform for scalable and high-titer production of adeno-associated virus serotype 1-12 vectors for gene therapy, Hum Gene Therapy, vol. 25(3):212-222, Mar. 2014 (Jan. 2014).
Mingozzi et al., Overcoming preexisting humoral immunity to AAV using capsid decoys, Sci Transl med, vol. 5(194), Jul. 2013.
Moskalenko et al., Epitope mapping of human anti-adeno-associated virus type 2 neutralizing antibodies: implications for gene therapy and virus structure, Journal of Virology, vol. 74:1761-1766, Feb. 2000.
Nam et al., Structure of adeno-associated virus serotype 8, a gene therapy vector, J Virol, vol. 81:12260-12271, Nov. 2007 (Aug. 2007).
Okada et al., Scalable purification of adeno-associated virus serotype 1 (AAV1) and AAV8 vectors, using dual ion-exchange adsorptive membranes, Hum Gene Ther, vol. 20:1013-1021, Sep. 2009.
Pettersen et al., UCSF Chimera—a visualization system for exploratory research and analysis, J Comput Chem, vol. 25:1605-1612, Oct. 2004.
Potter et al., A simplified purification protocol for recombinant adeno-associated virus vectors, Molecular Therapy—Methods & Clinical Development, vol. 1:14034, Aug. 2014.
Pulicheria N. and Asokan A., Peptide affinity reagents for AAV capsid recognition and purification, Gene Ther. Oct. 18, 2011, 18(10):1020-1024, epub Apr. 14, 2011.
Qu et al., Separation of adeno-associated virus type 2 empty particles from genome containing vectors by anion-exchange column chromatography, Journal of Virological Methods, vol. 140(1-2):183-192, Feb. 2007.
Sanner et al., Reduced surface: an efficient way to compute molecular surfaces, Biopolymers, vol. 38:305-320, Mar. 1996.
Shen et al., Characterization of the relationship of AAV capsid domain swapping to liver transduction efficiency, Molecular Therapy, vol. 15:1955-1962, Nov. 2007 (ePub Aug. 2007).
Sommer et al., Quantification of adeno-associated virus particles and empty capsids by optical density measurement, Molec. Ther, vol. 7:122-128, Jan. 2003.
Sonntag et al., A viral assembly factor promotes AAV2 capsid formation in the nucleolus, Proc Natl Acad Sci USA, vol. 107:10220-10225, Jun. 2010 (ePub May 2010).
Tenney et al., AAV8 capsid variable regions at the two-fold symmetry axis contribute to high liver transduction by mediating nuclear entry and capsid uncoating, Virology, vol. 454:227-236, Apr. 2014 (ePub Mar. 2014).
Thomas et al., Scalable recombinant adeno-associated virus production using recombinant herpes simplex virus type 1 coinfection of suspension-adapted mammalian cells, Hum Gene Ther, vol. 20:861-870, Aug. 2009.
Thomson et al., A comprehensive comparison of multiple sequence alignments, Nucl. Acids Res., vol. 27(13):2682-2690, Jul. 1999.
Urabe et al., Removal of empty capsids from type 1 adeno-associated virus vector stocks by anion-exchange chromatography potentiates transgene expression, Molecular Therapy, vol. 13(4):823-828, Apr. 2006 (ePub Feb. 2006).
Virag et al., Producing recombinant adeno-associated virus in foster cells: overcoming production limitations using a baculovirus-insect cell expression strategy, Hu Gene Therapy, vol. 20:807-817, Aug. 2009.
Wang et al., Identification of an adeno-associated virus binding epitope for AV8 sepharose affinity resin, Molecular Therapy, vol. 2:15040, Jan. 2015.
Wobus et al., Monoclonal antibodies against the adeno-associated virus type 2 (AAV-2) capsid: epitope mapping and identification of capsid domains involved in AAV-2-cell interaction and neutralization of AAV-2 infection, Journal of Virology, vol. 74(19): 9281-9293, Oct. 2000.
Ye et al., Herpes simplex virus clearance during purification of a recombinant adeno-associated virus serotype 1 vector, Hu Gene Ther Clin Dev, vol. 25(4):212-217, Dec. 2014.
Zolotukhin et al., Production and purification of serotype 1, 2, and 5 recombinant adeno-associated viral vectors, Methods, vol. 28(2):158-167, Oct. 2002.
Final Office Action issued on related U.S. Appl. No. 16/060,405, dated Jan. 8, 2021.
Notice of Allowance issued on related U.S. Appl. No. 16/060,406, dated Jan. 25, 2021.
Notice of Allowance issued on related U.S. Appl. No. 16/060,408, dated Jan. 22, 2021.
Office action issued on related European Application No. 16822315.4, dated Apr. 30, 2020.
Office action issued on related European Application No. 16822315.4, dated Apr. 21, 2021.
Office Action issued on related European Application No. 16825937.2, dated Sep. 12, 2019.
Office action issued on counterpart European Application No. 16825937.2, dated Apr. 30, 2020.

(56) References Cited

OTHER PUBLICATIONS

Office action issued on counterpart European application No. 16884241.7, dated Aug. 7, 2020.
Office Action issued on related European Application No. 16884241.7, dated Mar. 29, 2019.
Response to Office Action dated Oct. 8, 2019 issued on related European Patent Application No. 16884241.7, dated Mar. 29, 2019.
Office action issued on related European application No. 16884241.7, dated Nov. 26, 2019.
Response to Office action dated Nov. 26, 2020 issued on related European Patent Application No. 16884241.7, dated Jun. 8, 2020.
U.S. Appl. No. 62/266,347, filed Dec. 11, 2015.
U.S. Appl. No. 62/322,055, filed Apr. 13, 2016.
International Search Report and Written Opinion issued on International Patent Application No. PCT/US2016/066013, dated Mar. 13, 2017.
Blouin et al., "Improving rAAV production and purification: towards the definition of a scaleable process," The Journal of Gene Medicine, vol. 6:S223-S228, DOI: 10.1002/jgm.505, Feb. 2004.
GE Healthcare, Ion Exchange Chromatography & Chromatofocusing: Principles and Methods, pp. 1-59, Jan. 2010.
Giove et al., "Transduction of the inner mouse retina using AAVrh8 and AAVrh10 via intravitreal injection," Experimental Eye Research, vol. 91(5):652-659, Nov. 2010.
Grosse et al., "Relevance of Assembly-Activating Protein for Adeno-Associated Virus Vector Production and Capsid Protein Stability in Mammalian and Insect Cells," American Sociate for Microbiology Journal of Virology, vol. 91(20):e01198-17, Oct. 2017.
Hordeaux et al., "Efficient central nervous system AAVrh10-mediated intrathecal gene transfer in adult and neonate rats," Gene Therapy, vol. 22(4):316-324, Apr. 2015.
Mary et al., "Post-translational modifications in capsid proteins of recombinant adeno-associated virus (AAV) 1-rh10 serotypes," The FEBS Journal, vol. 286:4964-4981, Jul. 2019.
Merten, "AAV vector production: state of the art developments and remaining challenges," Bioinsights: Cell & Gene therapy Insights, pp. 521-551, DOI: 10.18609/cgti.2016.067, Dec. 2016.
Qu et al., "Calcium-ion-modulated ceramic hydroxyapatite resin for the scalable purification of recombinant Adeno Associated Virus serotype 9," Journal of Chromatography B, vol. 990(2015):15-22, Mar. 2015.
Thwaite et al., "AAVrh.10 immunogenicity in mice and humans. Relevance of antibody cross-reactivity in human gene therapy," Gene Therapy, vol. 22(2):196-201, Nov. 2014.
ScienceDriect Topics, https://www.sciencedirect.com/topics/agricultural-andbiological-sciences/fast-protein-liquid-chromatography, retrieved Feb. 21, 2023.
Product Sheet & Instruction Manual. CIMac™ QA-0.1 Analytical Column (Quaternary amine) (Pores 1.3 μm), BIA Separations. Publication #:PSIM-110.5113-1.3-1903-FZE, pp. 1-9. 2019.
Product Information Sheet. POROS™ HQ and PI Perfusion Chromatography™ Columnns for Anion Exchange Chromatography. Thermoscientific, pp. 1-6, Jul. 14, 2017.
Ion Exchange Chromatography. Webpage assessed from https://www.separations.eu.tosohbioscience.com/solutions/hplc-products/ionexchange on May 2, 2019, 2 pages.
Response to Communication issued pursuant to Art. 94(2) EPC issued on European Patent Application No. 16884241.7, dated Oct. 8, 2019.
Office Action issued on U.S. Appl. No. 17/328,687, dated Aug. 18, 2022.
Office Action issued on U.S. Appl. No. 17/379,359, dated Sep. 21, 2022.
Notice of Opposition filed for European Patent No. 3387138, dated Nov. 9, 2022.
Extended European Search Report issued on European Patent Application No. 21188952.2, dated Mar. 31, 2022.
U.S. Appl. No. 62/266,357, filed Dec. 11, 2015.
U.S. Appl. No. 62/322,071 P2, filed Apr. 13, 2016.

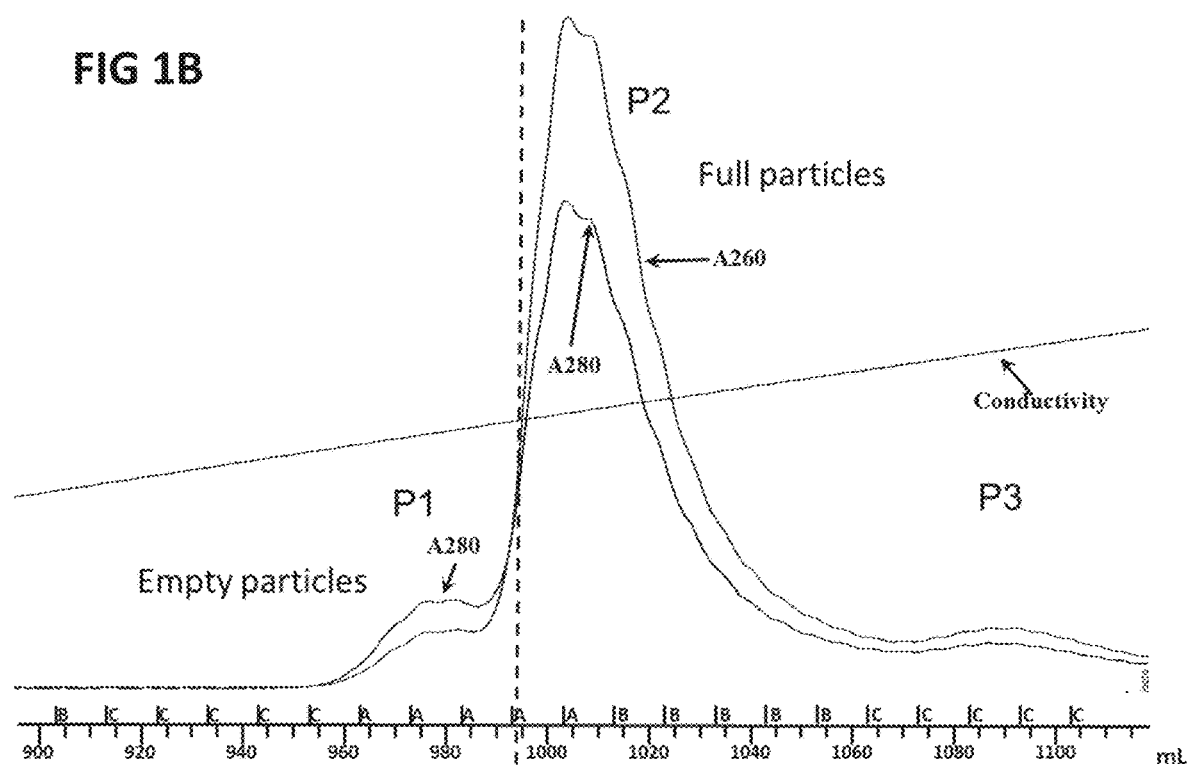
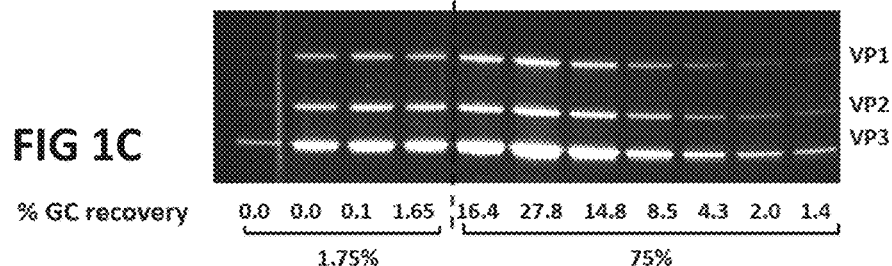

FIG 1F

| | GC | VP3 Raw vol | Calc particles | pt:vg |
|---|---|---|---|---|
| PD005 | 5.20E+10 | 101871 | 4.86E+10 | 0.93 |
| | 2.60E+10 | 48745 | 2.20E+10 | 0.85 |
| | 1.30E+10 | 25875 | 1.06E+10 | 0.81 |

FIG 1G

| | | | | |
|---|---|---|---|---|
| PD008 | 5.20E+10 | 108188 | 5.17E+10 | 0.99 |
| | 2.60E+10 | 49527 | 2.24E+10 | 0.86 |
| | 1.30E+10 | 25680 | 1.05E+10 | 0.80 |

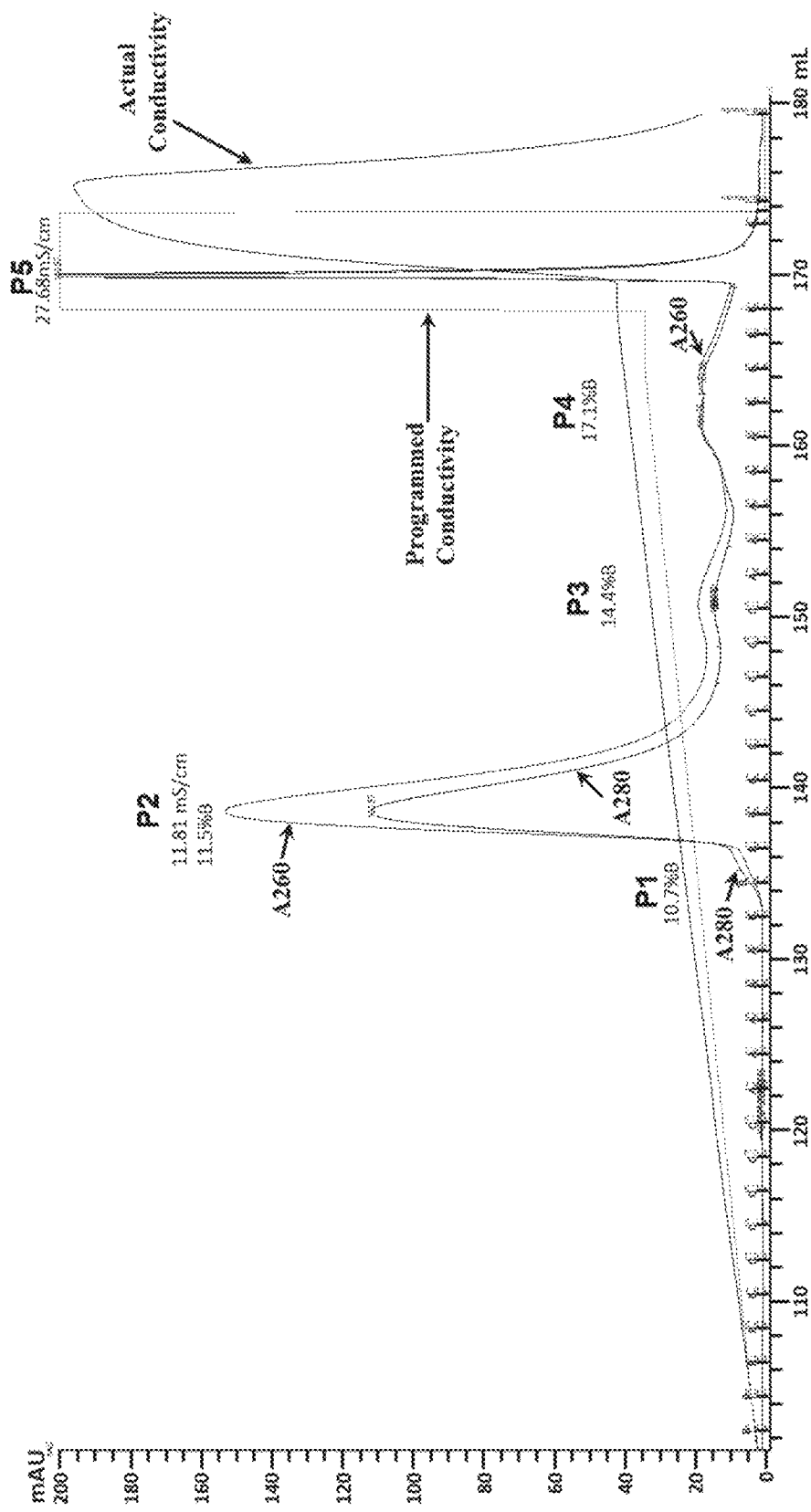

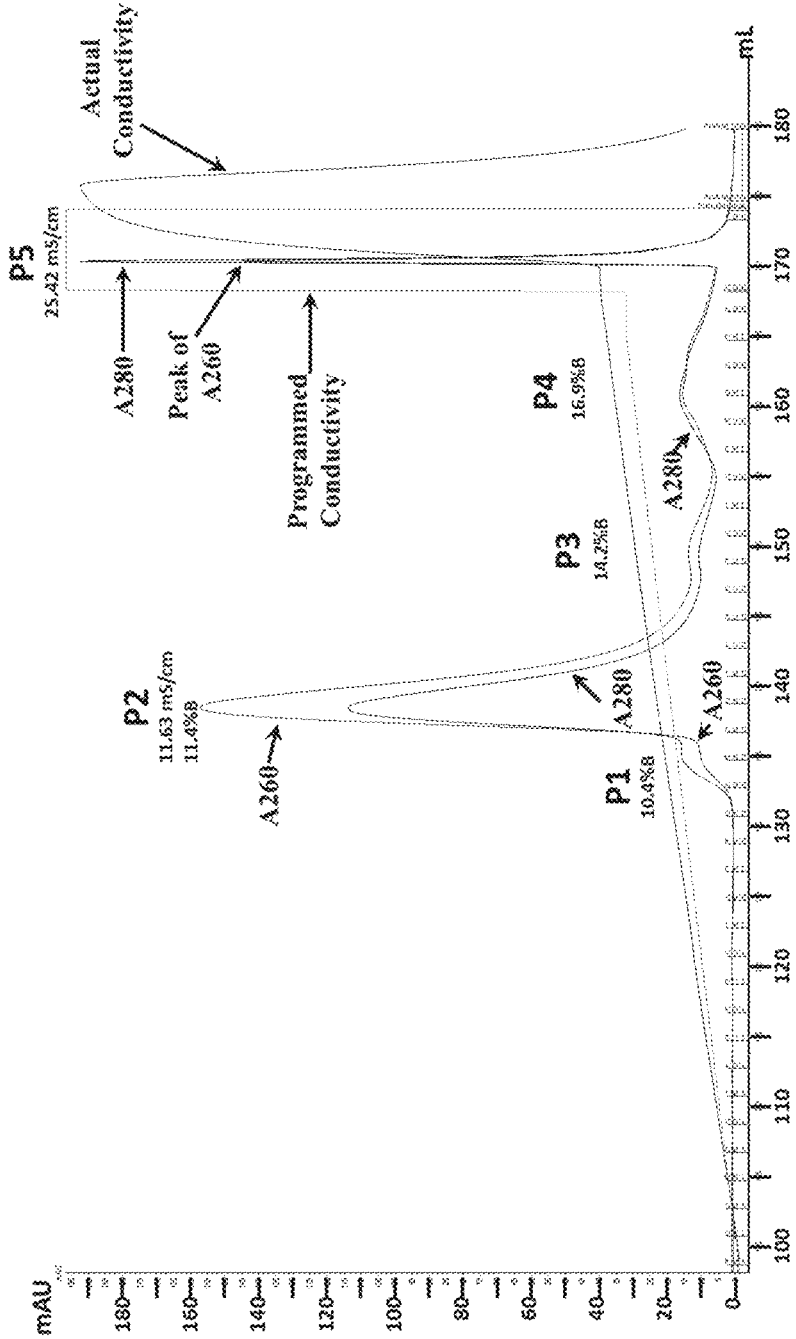

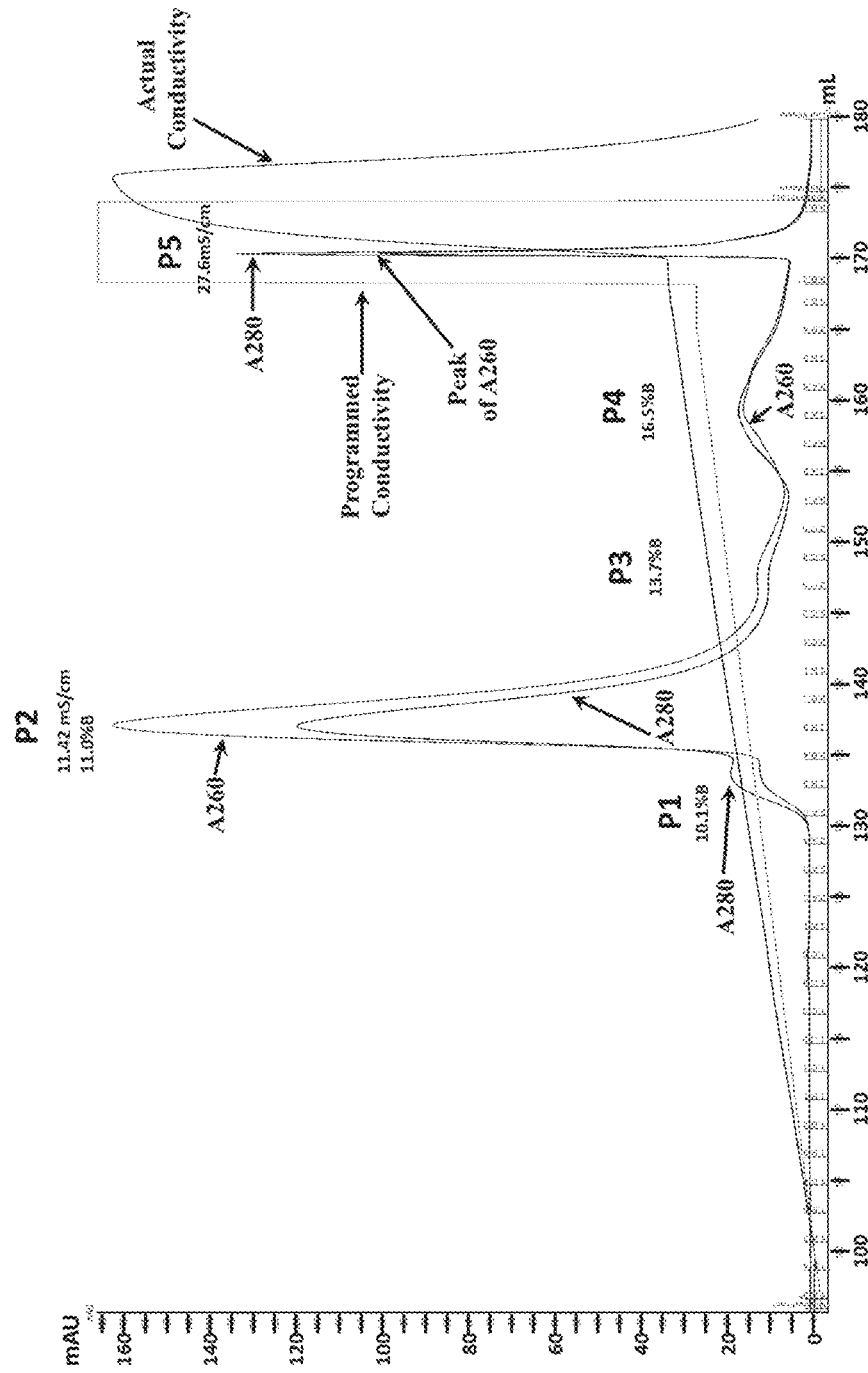

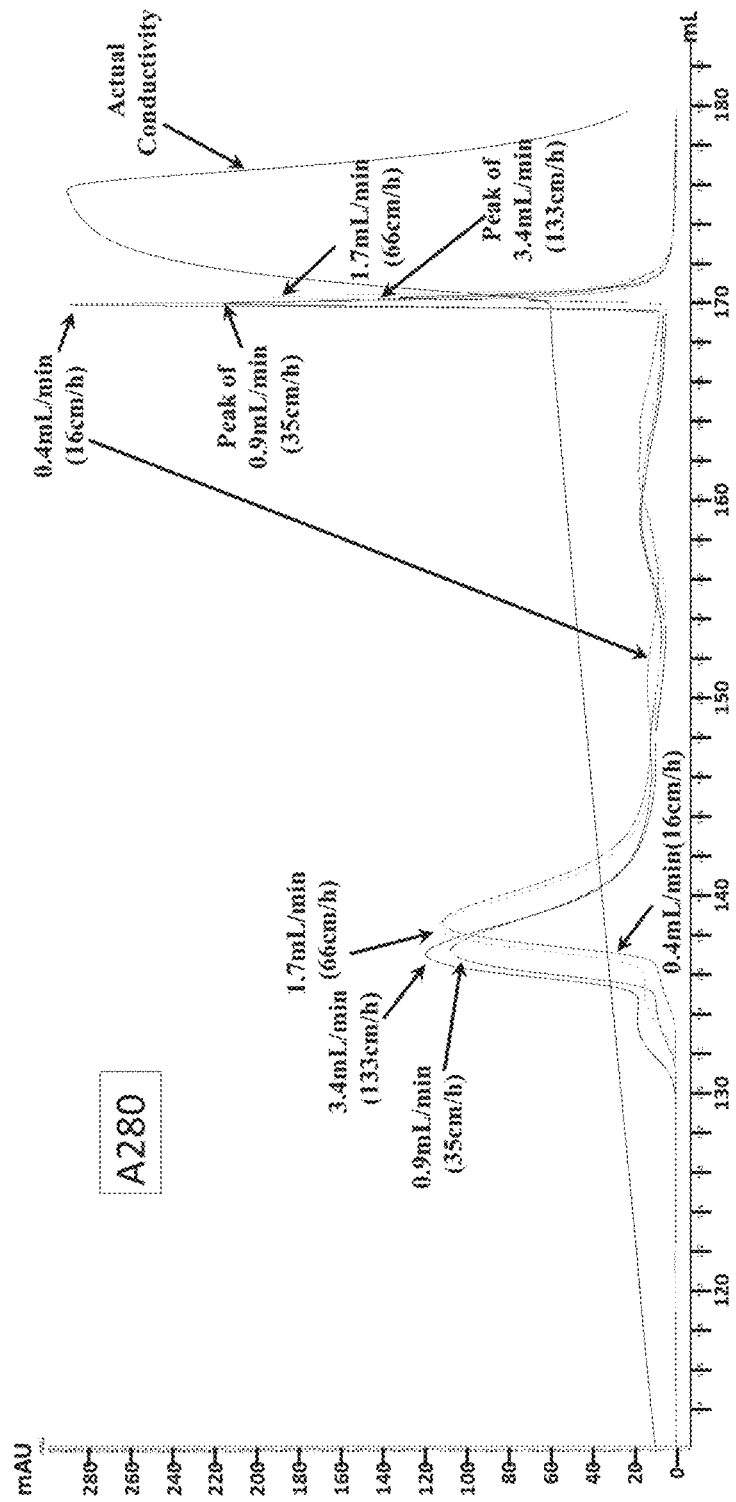

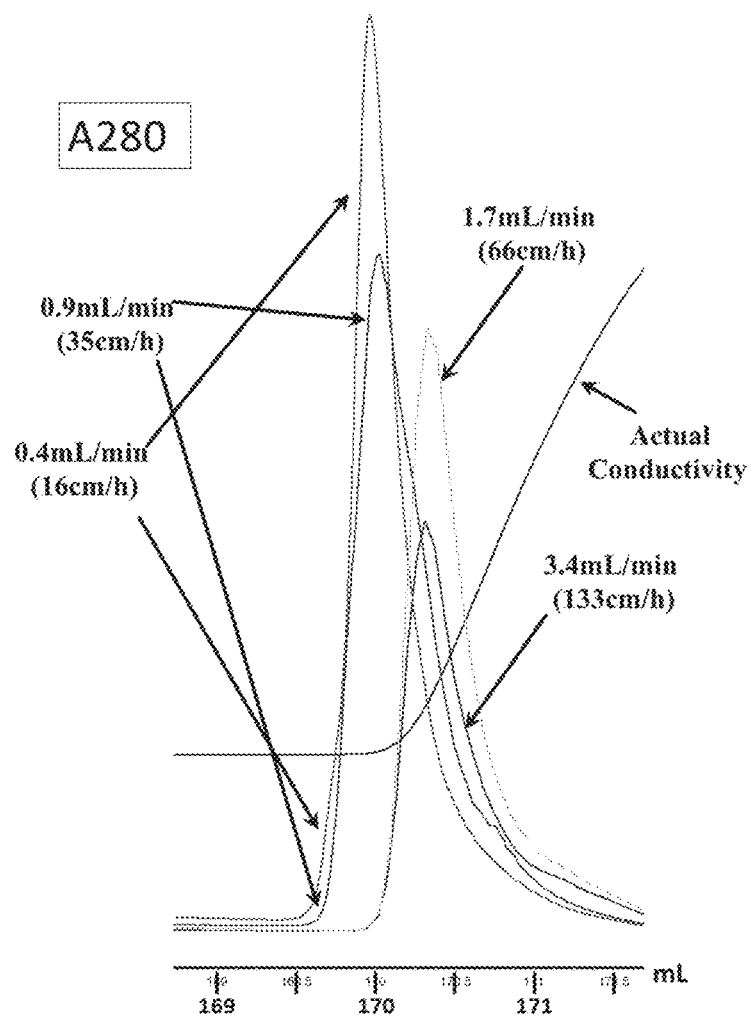

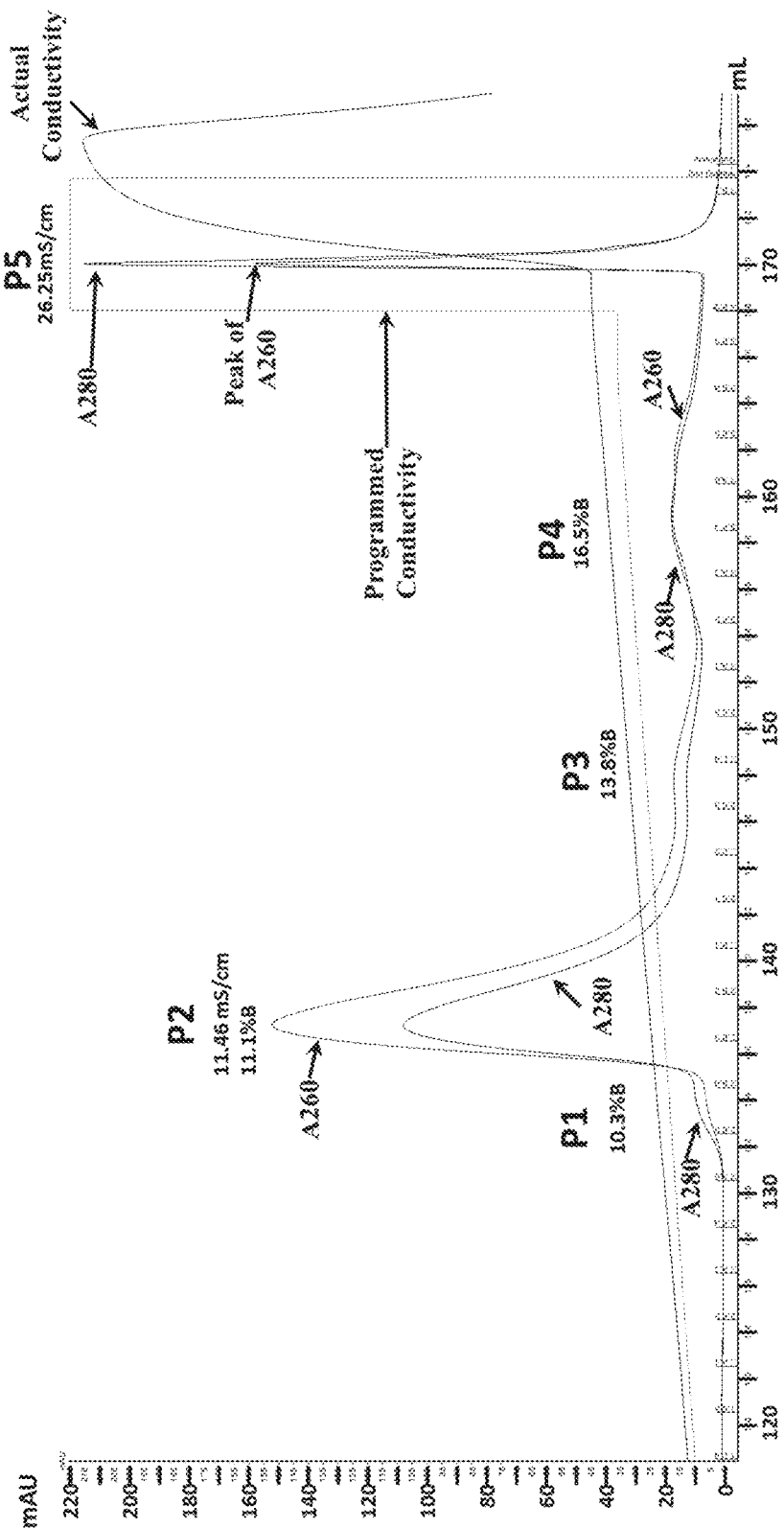

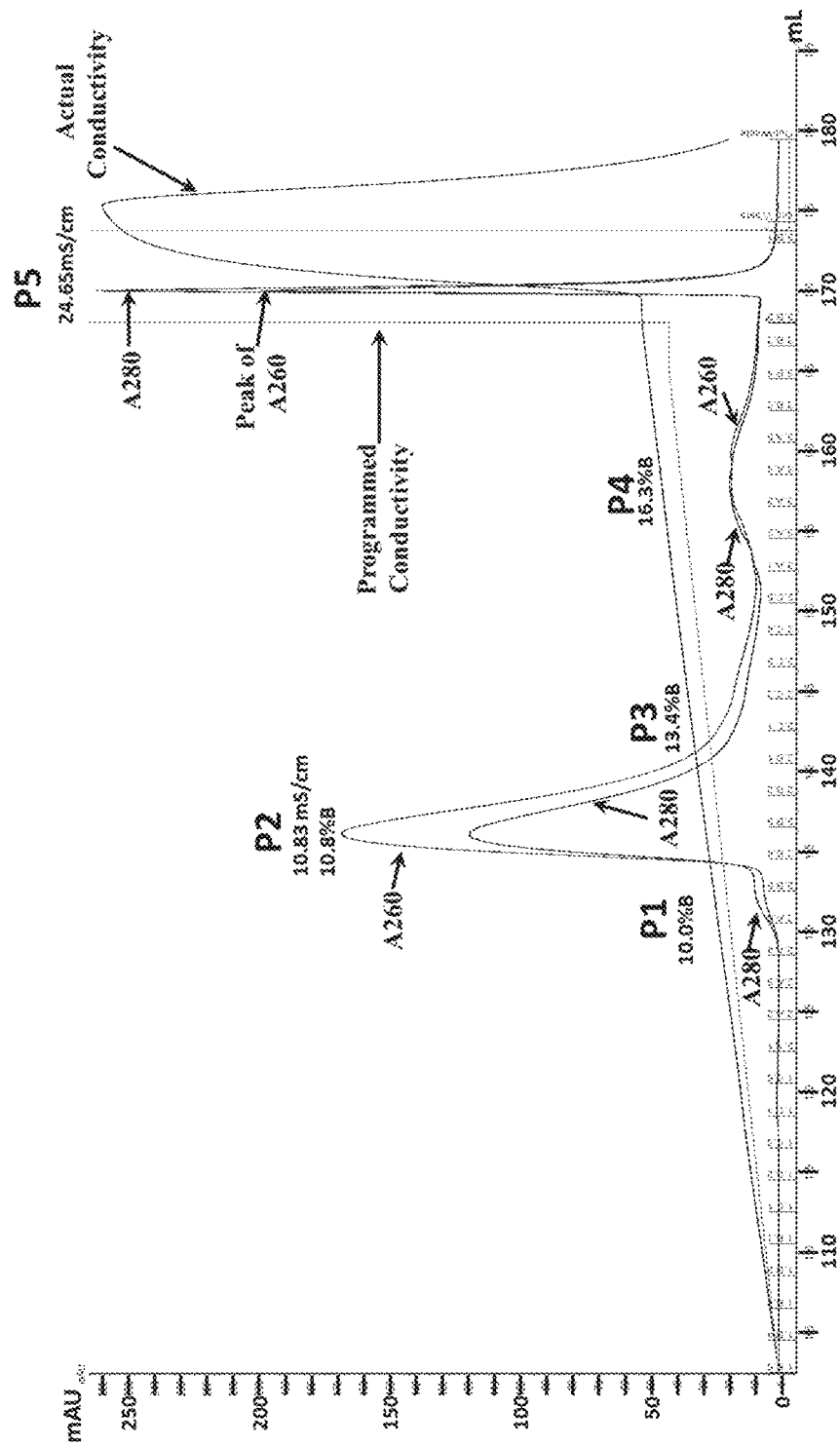

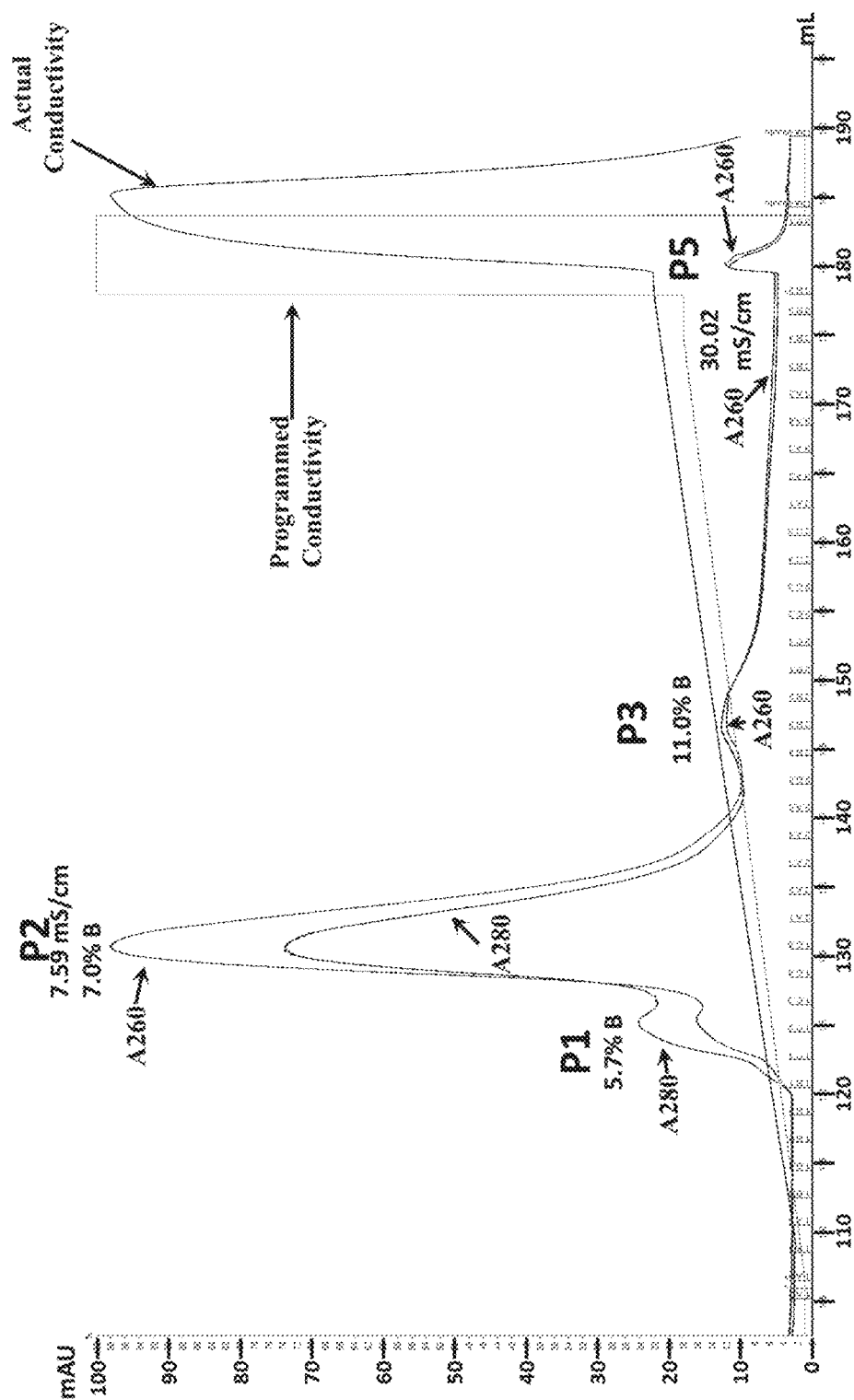

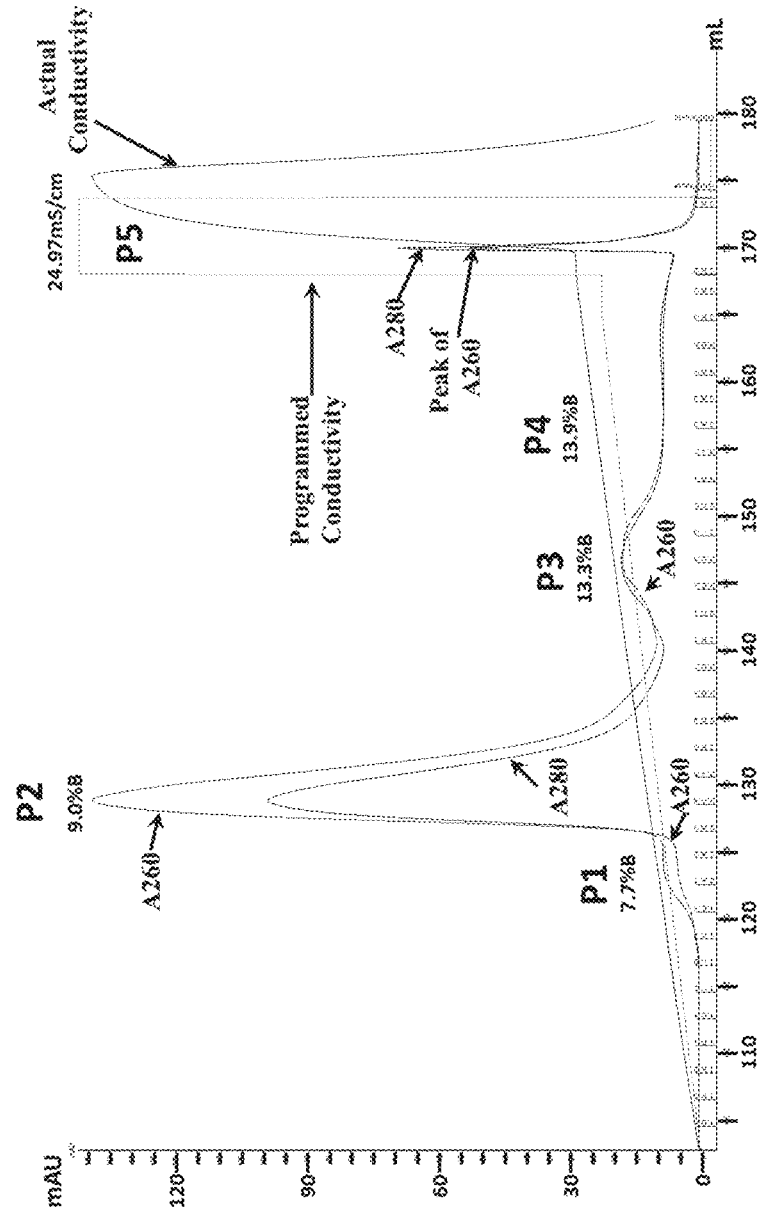

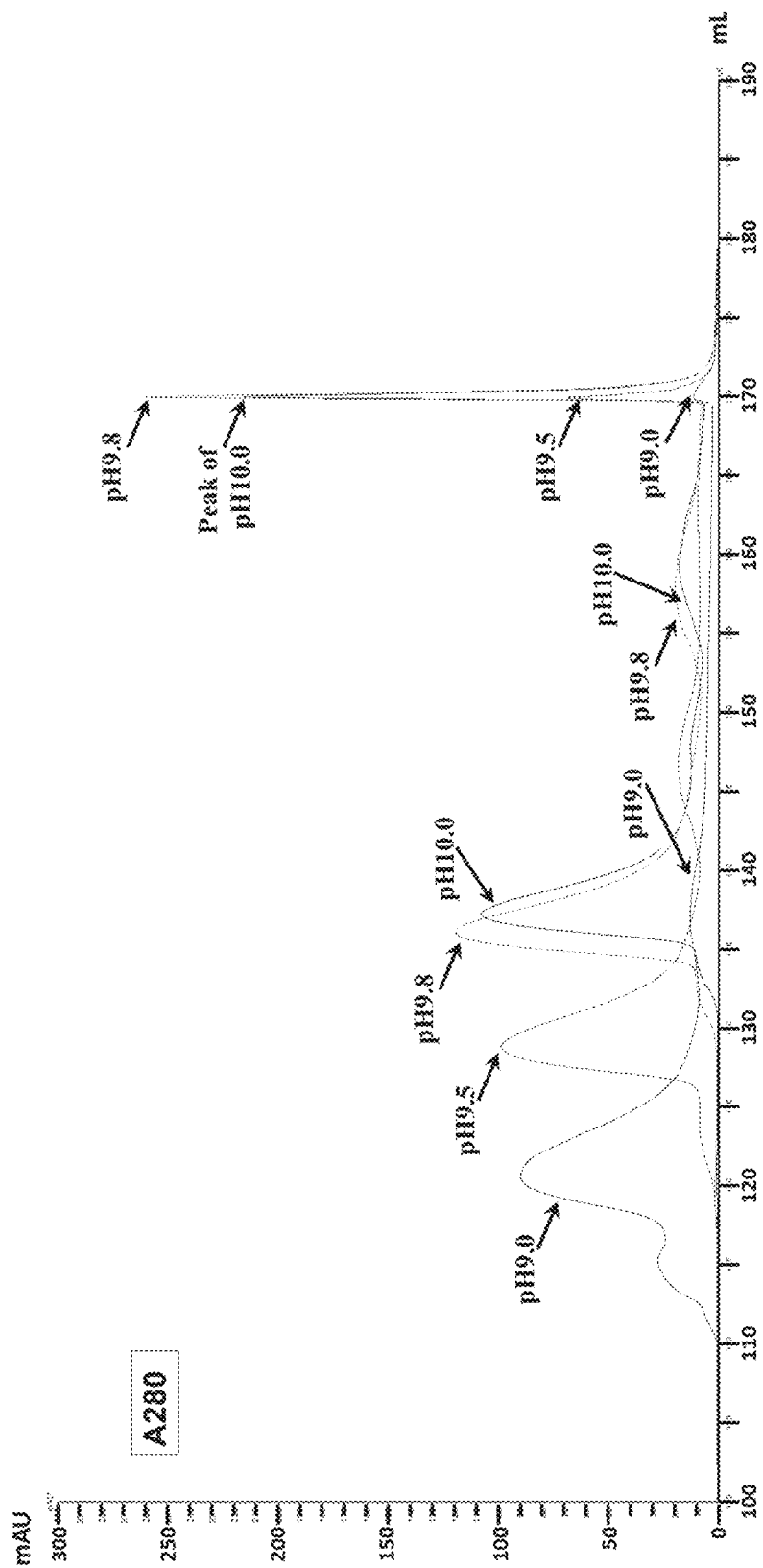

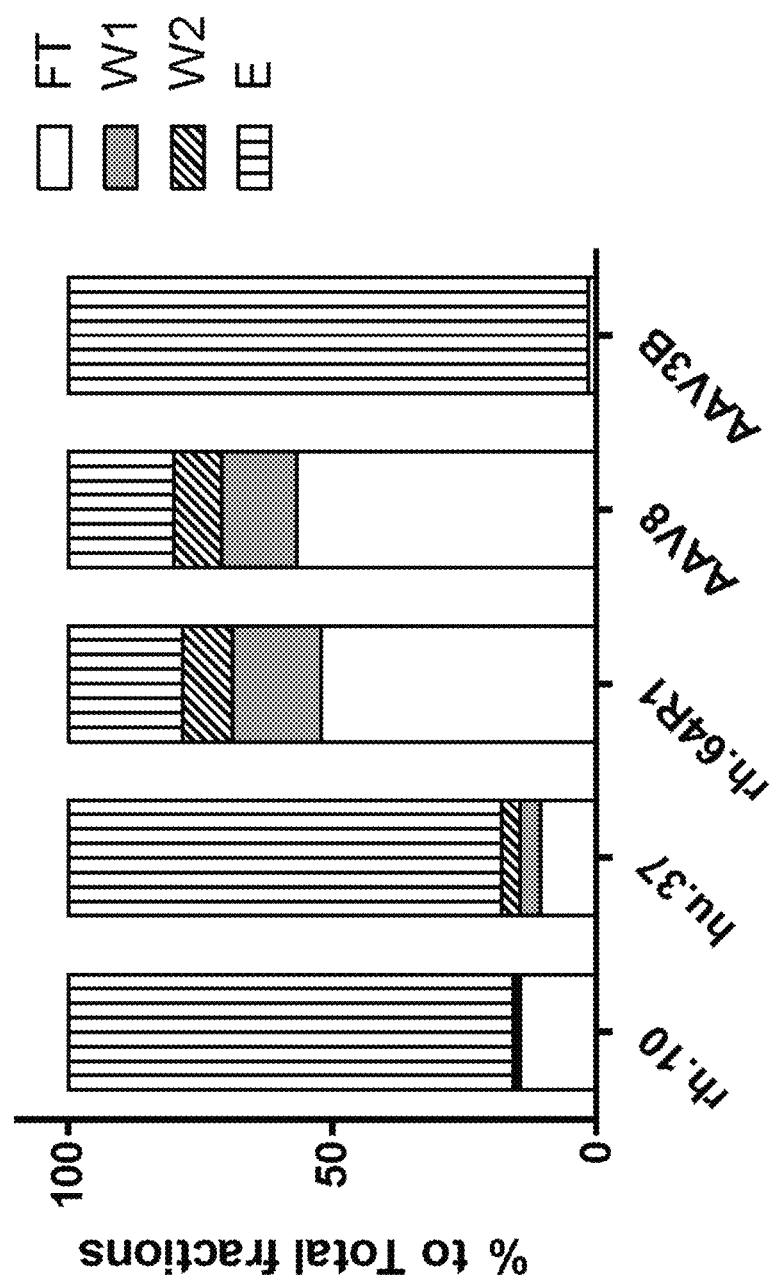

```
                       SEQUENCE LISTING

<160> NUMBER OF SEQ ID NOS: 22

<210> SEQ ID NO 1
<211> LENGTH: 736
<212> TYPE: PRT
<213> ORGANISM: Artificial Sequence
<220> FEATURE:
<223> OTHER INFORMATION: Adeno-associated virus 1 vp1 capsid protein

<400> SEQUENCE: 1

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp Gln
65                  70                  75                  80

Gln Leu Lys Ala Gly Asp Asn Pro Tyr Leu Arg Tyr Asn His Ala Asp
                85                  90                  95

Ala Glu Phe Gln Glu Arg Leu Gln Glu Asp Thr Ser Phe Gly Gly Asn
            100                 105                 110

Leu Gly Arg Ala Val Phe Gln Ala Lys Lys Arg Val Leu Glu Pro Leu
        115                 120                 125

Gly Leu Val Glu Glu Gly Ala Lys Thr Ala Pro Gly Lys Lys Arg Pro
    130                 135                 140

Val Glu Gln Ser Pro Gln Glu Pro Asp Ser Ser Ser Gly Ile Gly Lys
145                 150                 155                 160

Thr Gly Gln Gln Pro Ala Lys Lys Arg Leu Asn Phe Gly Gln Thr Gly
                165                 170                 175

Asp Ser Glu Ser Val Pro Asp Pro Gln Pro Leu Gly Glu Pro Pro
            180                 185                 190
```

-continued

```
Ala Thr Pro Ala Ala Val Gly Pro Thr Thr Met Ala Ser Gly Gly
            195                 200                 205
Ala Pro Met Ala Asp Asn Asn Glu Gly Ala Asp Gly Val Gly Asn Ala
210                 215                 220
Ser Gly Asn Trp His Cys Asp Ser Thr Trp Leu Gly Asp Arg Val Ile
225                 230                 235                 240
Thr Thr Ser Thr Arg Thr Trp Ala Leu Pro Thr Tyr Asn Asn His Leu
            245                 250                 255
Tyr Lys Gln Ile Ser Ser Ala Ser Thr Gly Ala Ser Asn Asp Asn His
                260                 265                 270
Tyr Phe Gly Tyr Ser Thr Pro Trp Gly Tyr Phe Asp Phe Asn Arg Phe
            275                 280                 285
His Cys His Phe Ser Pro Arg Asp Trp Gln Arg Leu Ile Asn Asn Asn
            290                 295                 300
Trp Gly Phe Arg Pro Lys Arg Leu Asn Phe Lys Leu Phe Asn Ile Gln
305                 310                 315                 320
Val Lys Glu Val Thr Thr Asn Asp Gly Val Thr Thr Ile Ala Asn Asn
                325                 330                 335
Leu Thr Ser Thr Val Gln Val Phe Ser Asp Ser Glu Tyr Gln Leu Pro
            340                 345                 350
Tyr Val Leu Gly Ser Ala His Gln Gly Cys Leu Pro Pro Phe Pro Ala
            355                 360                 365
Asp Val Phe Met Ile Pro Gln Tyr Gly Tyr Leu Thr Leu Asn Asn Gly
            370                 375                 380
Ser Gln Ala Val Gly Arg Ser Ser Phe Tyr Cys Leu Glu Tyr Phe Pro
385                 390                 395                 400
Ser Gln Met Leu Arg Thr Gly Asn Asn Phe Thr Phe Ser Tyr Thr Phe
            405                 410                 415
Glu Glu Val Pro Phe His Ser Ser Tyr Ala His Ser Gln Ser Leu Asp
            420                 425                 430
Arg Leu Met Asn Pro Leu Ile Asp Gln Tyr Leu Tyr Tyr Leu Asn Arg
            435                 440                 445
Thr Gln Asn Gln Ser Gly Ser Ala Gln Asn Lys Asp Leu Leu Phe Ser
            450                 455                 460
Arg Gly Ser Pro Ala Gly Met Ser Val Gln Pro Lys Asn Trp Leu Pro
465                 470                 475                 480
Gly Pro Cys Tyr Arg Gln Gln Arg Val Ser Lys Thr Lys Thr Asp Asn
            485                 490                 495
Asn Asn Ser Asn Phe Thr Trp Thr Gly Ala Ser Lys Tyr Asn Leu Asn
            500                 505                 510
Gly Arg Glu Ser Ile Ile Asn Pro Gly Thr Ala Met Ala Ser His Lys
            515                 520                 525
Asp Asp Glu Asp Lys Phe Phe Pro Met Ser Gly Val Met Ile Phe Gly
530                 535                 540
Lys Glu Ser Ala Gly Ala Ser Asn Thr Ala Leu Asp Asn Val Met Ile
545                 550                 555                 560
Thr Asp Glu Glu Glu Ile Lys Ala Thr Asn Pro Val Ala Thr Glu Arg
                565                 570                 575
Phe Gly Thr Val Ala Val Asn Phe Gln Ser Ser Ser Thr Asp Pro Ala
            580                 585                 590
Thr Gly Asp Val His Ala Met Gly Ala Leu Pro Gly Met Val Trp Gln
            595                 600                 605
```

```
Asp Arg Asp Val Tyr Leu Gln Gly Pro Ile Trp Ala Lys Ile Pro His
    610                 615                 620

Thr Asp Gly His Phe His Pro Ser Pro Leu Met Gly Gly Phe Gly Leu
625                 630                 635                 640

Lys Asn Pro Pro Gln Ile Leu Ile Lys Asn Thr Pro Val Pro Ala
            645                 650                 655

Asn Pro Pro Ala Glu Phe Ser Ala Thr Lys Phe Ala Ser Phe Ile Thr
            660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Val Gln Tyr Thr Ser Asn
690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
                725                 730                 735

<210> SEQ ID NO 2
<211> LENGTH: 735
<212> TYPE: PRT
<213> ORGANISM: Artificial Sequence
<220> FEATURE:
<223> OTHER INFORMATION: Adeno-associated virus 2 vp1 capsid protein

<400> SEQUENCE: 2

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro
            20                  25                  30

Lys Pro Ala Glu Arg His Lys Asp Asp Ser Arg Gly Leu Val Leu Pro
            35                  40                  45

Gly Tyr Lys Tyr Leu Gly Pro Phe Asn Gly Leu Asp Lys Gly Glu Pro
        50                  55                  60

Val Asn Glu Ala Asp Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Met Gly Asp Arg Val Ile
225                 230                 235                 240
```

```
Thr Thr Ser Thr Arg Thr Trp Ala Leu Pro Thr Tyr Asn Asn His Leu
            245                 250                 255

Tyr Lys Gln Ile Ser Ser Gln Ser Gly Ala Ser Asn Asp Asn His Tyr
        260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Ile Ala Asn Asn Leu
                325                 330                 335

Thr Ser Thr Val Gln Val Phe Thr Asp Ser Glu Tyr Gln Leu Pro Tyr
                340                 345                 350

Val Leu Gly Ser Ala His Gln Gly Cys Leu Pro Pro Phe Pro Ala Asp
            355                 360                 365

Val Phe Met Val Pro Gln Tyr Gly Tyr Leu Thr Leu Asn Asn Gly Ser
    370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
                420                 425                 430

Leu Met Asn Pro Leu Ile Asp Gln Tyr Leu Tyr Tyr Leu Ser Arg Thr
            435                 440                 445

Asn Thr Pro Ser Gly Thr Thr Thr Gln Ser Arg Leu Gln Phe Ser Gln
        450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
            500                 505                 510

Arg Asp Ser Leu Val Asn Pro Gly Pro Ala Met Ala Ser His Lys Asp
        515                 520                 525

Asp Glu Glu Lys Phe Phe Pro Gln Ser Gly Val Leu Ile Phe Gly Lys
        530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
                565                 570                 575

Gly Ser Val Ser Thr Asn Leu Gln Arg Gly Asn Arg Gln Ala Ala Thr
                580                 585                 590

Ala Asp Val Asn Thr Gln Gly Val Leu Pro Gly Met Val Trp Gln Asp
            595                 600                 605

Arg Asp Val Tyr Leu Gln Gly Pro Ile Trp Ala Lys Ile Pro His Thr
        610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
                645                 650                 655
```

Pro Ser Thr Thr Phe Ser Ala Ala Lys Phe Ala Ser Phe Ile Thr Gln
            660                 665                 670

Tyr Ser Thr Gly Gln Val Ser Val Glu Ile Glu Trp Glu Leu Gln Lys
        675                 680                 685

Glu Asn Ser Lys Arg Trp Asn Pro Glu Ile Gln Tyr Thr Ser Asn Tyr
    690                 695                 700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
                725                 730                 735

<210> SEQ ID NO 3
<211> LENGTH: 736
<212> TYPE: PRT
<213> ORGANISM: Artificial Sequence
<220> FEATURE:
<223> OTHER INFORMATION: Adeno-associated virus 3 vp1 capsid protein

<400> SEQUENCE: 3

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Val Pro Gln Pro
            20                  25                  30

Lys Ala Asn Gln Gln His Gln Asp Asn Arg Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Glu Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Ile Leu Glu Pro
        115                 120                 125

Leu Gly Leu Val Glu Glu Ala Ala Lys Thr Ala Pro Gly Lys Lys Gly
    130                 135                 140

Ala Val Asp Gln Ser Pro Gln Glu Pro Asp Ser Ser Ser Gly Val Gly
145                 150                 155                 160

Lys Ser Gly Lys Gln Pro Ala Arg Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Ala Pro Thr Ser Leu Gly Ser Asn Thr Met Ala Ser Gly Gly Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

-continued

```
Cys His Phe Ser Pro Arg Asp Trp Gln Arg Leu Ile Asn Asn Asn Trp
    290                 295                 300
Gly Phe Arg Pro Lys Lys Leu Ser Phe Lys Leu Phe Asn Ile Gln Val
305                 310                 315                 320
Arg Gly Val Thr Gln Asn Asp Gly Thr Thr Thr Ile Ala Asn Asn Leu
                325                 330                 335
Thr Ser Thr Val Gln Val Phe Thr Asp Ser Glu Tyr Gln Leu Pro Tyr
            340                 345                 350
Val Leu Gly Ser Ala His Gln Gly Cys Leu Pro Pro Phe Pro Ala Asp
        355                 360                 365
Val Phe Met Val Pro Gln Tyr Gly Tyr Leu Thr Leu Asn Asn Gly Ser
370                 375                 380
Gln Ala Val Gly Arg Ser Ser Phe Tyr Cys Leu Glu Tyr Phe Pro Ser
385                 390                 395                 400
Gln Met Leu Arg Thr Gly Asn Asn Phe Gln Phe Ser Tyr Thr Phe Glu
                405                 410                 415
Asp Val Pro Phe His Ser Ser Tyr Ala His Ser Gln Ser Leu Asp Arg
            420                 425                 430
Leu Met Asn Pro Leu Ile Asp Gln Tyr Leu Tyr Tyr Leu Asn Arg Thr
        435                 440                 445
Gln Gly Thr Thr Ser Gly Thr Thr Asn Gln Ser Arg Leu Leu Phe Ser
450                 455                 460
Gln Ala Gly Pro Gln Ser Met Ser Leu Gln Ala Arg Asn Trp Leu Pro
465                 470                 475                 480
Gly Pro Cys Tyr Arg Gln Gln Arg Leu Ser Lys Thr Ala Asn Asp Asn
                485                 490                 495
Asn Asn Ser Asn Phe Pro Trp Thr Ala Ala Ser Lys Tyr His Leu Asn
            500                 505                 510
Gly Arg Asp Ser Leu Val Asn Pro Gly Pro Ala Met Ala Ser His Lys
        515                 520                 525
Asp Asp Glu Glu Lys Phe Phe Pro Met His Gly Asn Leu Ile Phe Gly
530                 535                 540
Lys Glu Gly Thr Thr Ala Ser Asn Ala Glu Leu Asp Asn Val Met Ile
545                 550                 555                 560
Thr Asp Glu Glu Glu Ile Arg Thr Thr Asn Pro Val Ala Thr Glu Gln
                565                 570                 575
Tyr Gly Thr Val Ala Asn Asn Leu Gln Ser Ser Asn Thr Ala Pro Thr
            580                 585                 590
Thr Gly Thr Val Asn His Gln Gly Ala Leu Pro Gly Met Val Trp Gln
        595                 600                 605
Asp Arg Asp Val Tyr Leu Gln Gly Pro Ile Trp Ala Lys Ile Pro His
610                 615                 620
Thr Asp Gly His Phe His Pro Ser Pro Leu Met Gly Gly Phe Gly Leu
625                 630                 635                 640
Lys His Pro Pro Pro Gln Ile Met Ile Lys Asn Thr Pro Val Pro Ala
                645                 650                 655
Asn Pro Pro Thr Thr Phe Ser Pro Ala Lys Phe Ala Ser Phe Ile Thr
            660                 665                 670
Gln Tyr Ser Thr Gly Gln Val Ser Val Glu Ile Glu Trp Glu Leu Gln
        675                 680                 685
Lys Glu Asn Ser Lys Arg Trp Asn Pro Glu Ile Gln Tyr Thr Ser Asn
690                 695                 700
```

Tyr Asn Lys Ser Val Asn Val Asp Phe Thr Val Asp Thr Asn Gly Val
705                 710                 715                 720

Tyr Ser Glu Pro Arg Pro Ile Gly Thr Arg Tyr Leu Thr Arg Asn Leu
            725                 730                 735

<210> SEQ ID NO 4
<211> LENGTH: 736
<212> TYPE: PRT
<213> ORGANISM: Artificial Sequence
<220> FEATURE:
<223> OTHER INFORMATION: Adeno-associated virus 3B vp1 capsid protein

<400> SEQUENCE: 4

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Val Pro Gln Pro
            20                  25                  30

Lys Ala Asn Gln Gln His Gln Asp Asn Arg Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Glu Ala Asp Ala Ala Leu Glu His Asp Lys Ala Tyr Asp Gln
65                  70                  75                  80

Gln Leu Lys Ala Gly Asp Asn Pro Tyr Leu Lys Tyr Asn His Ala Asp
                85                  90                  95

Ala Glu Phe Gln Glu Arg Leu Gln Glu Asp Thr Ser Phe Gly Gly Asn
            100                 105                 110

Leu Gly Arg Ala Val Phe Gln Ala Lys Lys Arg Ile Leu Glu Pro Leu
        115                 120                 125

Gly Leu Val Glu Glu Ala Ala Lys Thr Ala Pro Gly Lys Lys Arg Pro
    130                 135                 140

Val Asp Gln Ser Pro Gln Glu Pro Asp Ser Ser Ser Gly Val Gly Lys
145                 150                 155                 160

Ser Gly Lys Gln Pro Ala Arg Lys Arg Leu Asn Phe Gly Gln Thr Gly
                165                 170                 175

Asp Ser Glu Ser Val Pro Asp Pro Gln Pro Leu Gly Glu Pro Pro Ala
            180                 185                 190

Ala Pro Thr Ser Leu Gly Ser Asn Thr Met Ala Ser Gly Gly Gly Ala
        195                 200                 205

Pro Met Ala Asp Asn Asn Glu Gly Ala Asp Gly Val Gly Asn Ser Ser
    210                 215                 220

Gly Asn Trp His Cys Asp Ser Gln Trp Leu Gly Asp Arg Val Ile Thr
225                 230                 235                 240

Thr Ser Thr Arg Thr Trp Ala Leu Pro Thr Tyr Asn Asn His Leu Tyr
                245                 250                 255

Lys Gln Ile Ser Ser Gln Ser Gly Ala Ser Asn Asp Asn His Tyr Phe
            260                 265                 270

Gly Tyr Ser Thr Pro Trp Gly Tyr Phe Asp Phe Asn Arg Phe His Cys
        275                 280                 285

His Phe Ser Pro Arg Asp Trp Gln Arg Leu Ile Asn Asn Asn Trp Gly
    290                 295                 300

Phe Arg Pro Lys Lys Leu Ser Phe Lys Leu Phe Asn Ile Gln Val Lys
305                 310                 315                 320

```
Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

Val Phe Met Val Pro Gln Tyr Gly Tyr Leu Thr Leu Asn Asn Gly Ser
    370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Gln Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Asn Arg Thr
        435                 440                 445

Gln Gly Thr Thr Ser Gly Thr Thr Asn Gln Ser Arg Leu Leu Phe Ser
    450                 455                 460

Gln Ala Gly Pro Gln Ser Met Ser Leu Gln Ala Arg Asn Trp Leu Pro
465                 470                 475                 480

Gly Pro Cys Tyr Arg Gln Gln Arg Leu Ser Lys Thr Ala Asn Asp Asn
                485                 490                 495

Asn Asn Ser Asn Phe Pro Trp Thr Ala Ala Ser Lys Tyr His Leu Asn
            500                 505                 510

Gly Arg Asp Ser Leu Val Asn Pro Gly Pro Ala Met Ala Ser His Lys
        515                 520                 525

Asp Asp Glu Glu Lys Phe Phe Pro Met His Gly Asn Leu Ile Phe Gly
    530                 535                 540

Lys Glu Gly Thr Thr Ala Ser Asn Ala Glu Leu Asp Asn Val Met Ile
545                 550                 555                 560

Thr Asp Glu Glu Glu Ile Arg Thr Thr Asn Pro Val Ala Thr Glu Gln
                565                 570                 575

Tyr Gly Thr Val Ala Asn Asn Leu Gln Ser Ser Asn Thr Ala Pro Thr
            580                 585                 590

Thr Arg Thr Val Asn Asp Gln Gly Ala Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly His Phe His Pro Ser Pro Leu Met Gly Gly Phe Gly Leu
625                 630                 635                 640

Lys His Pro Pro Pro Gln Ile Met Ile Lys Asn Thr Pro Val Pro Ala
                645                 650                 655

Asn Pro Pro Thr Thr Phe Ser Pro Ala Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Asn Lys Ser Val Asn Val Asp Phe Thr Val Asp Thr Asn Gly Val
705                 710                 715                 720

Tyr Ser Glu Pro Arg Pro Ile Gly Thr Arg Tyr Leu Thr Arg Asn Leu
                725                 730                 735
```

-continued

```
<210> SEQ ID NO 5
<211> LENGTH: 724
<212> TYPE: PRT
<213> ORGANISM: Artificial Sequence
<220> FEATURE:
<223> OTHER INFORMATION: Adeno-associated virus 5 vp1 capsid protein

<400> SEQUENCE: 5

Met Ser Phe Val Asp His Pro Pro Asp Trp Leu Glu Glu Val Gly Glu
1               5                   10                  15

Gly Leu Arg Glu Phe Leu Gly Leu Glu Ala Gly Pro Pro Lys Pro Lys
            20                  25                  30

Pro Asn Gln Gln His Gln Asp Gln Ala Arg Gly Leu Val Leu Pro Gly
        35                  40                  45

Tyr Asn Tyr Leu Gly Pro Gly Asn Gly Leu Asp Arg Gly Glu Pro Val
    50                  55                  60

Asn Arg Ala Asp Glu Val Ala Arg Glu His Asp Ile Ser Tyr Asn Glu
65                  70                  75                  80

Gln Leu Glu Ala Gly Asp Asn Pro Tyr Leu Lys Tyr Asn His Ala Asp
                85                  90                  95

Ala Glu Phe Gln Glu Lys Leu Ala Asp Asp Thr Ser Phe Gly Gly Asn
            100                 105                 110

Leu Gly Lys Ala Val Phe Gln Ala Lys Lys Arg Val Leu Glu Pro Phe
        115                 120                 125

Gly Leu Val Glu Glu Gly Ala Lys Thr Ala Pro Thr Gly Lys Arg Ile
    130                 135                 140

Asp Asp His Phe Pro Lys Arg Lys Lys Ala Arg Thr Glu Glu Asp Ser
145                 150                 155                 160

Lys Pro Ser Thr Ser Ser Asp Ala Glu Ala Gly Pro Ser Gly Ser Gln
                165                 170                 175

Gln Leu Gln Ile Pro Ala Gln Pro Ala Ser Ser Leu Gly Ala Asp Thr
            180                 185                 190

Met Ser Ala Gly Gly Gly Gly Pro Leu Gly Asp Asn Asn Gln Gly Ala
        195                 200                 205

Asp Gly Val Gly Asn Ala Ser Gly Asp Trp His Cys Asp Ser Thr Trp
    210                 215                 220

Met Gly Asp Arg Val Val Thr Lys Ser Thr Arg Thr Trp Val Leu Pro
225                 230                 235                 240

Ser Tyr Asn Asn His Gln Tyr Arg Glu Ile Lys Ser Gly Ser Val Asp
                245                 250                 255

Gly Ser Asn Ala Asn Ala Tyr Phe Gly Tyr Ser Thr Pro Trp Gly Tyr
            260                 265                 270

Phe Asp Phe Asn Arg Phe His Ser His Trp Ser Pro Arg Asp Trp Gln
        275                 280                 285

Arg Leu Ile Asn Asn Tyr Trp Gly Phe Arg Pro Arg Ser Leu Arg Val
    290                 295                 300

Lys Ile Phe Asn Ile Gln Val Lys Glu Val Thr Val Gln Asp Ser Thr
305                 310                 315                 320

Thr Thr Ile Ala Asn Asn Leu Thr Ser Thr Val Gln Val Phe Thr Asp
                325                 330                 335

Asp Asp Tyr Gln Leu Pro Tyr Val Val Gly Asn Gly Thr Glu Gly Cys
            340                 345                 350

Leu Pro Ala Phe Pro Pro Gln Val Phe Thr Leu Pro Gln Tyr Gly Tyr
        355                 360                 365
```

```
Ala Thr Leu Asn Arg Asp Asn Thr Glu Asn Pro Thr Glu Arg Ser Ser
    370                 375                 380

Phe Phe Cys Leu Glu Tyr Phe Pro Ser Lys Met Leu Arg Thr Gly Asn
385                 390                 395                 400

Asn Phe Glu Phe Thr Tyr Asn Phe Glu Glu Val Pro Phe His Ser Ser
                405                 410                 415

Phe Ala Pro Ser Gln Asn Leu Phe Lys Leu Ala Asn Pro Leu Val Asp
            420                 425                 430

Gln Tyr Leu Tyr Arg Phe Val Ser Thr Asn Asn Thr Gly Gly Val Gln
        435                 440                 445

Phe Asn Lys Asn Leu Ala Gly Arg Tyr Ala Asn Thr Tyr Lys Asn Trp
    450                 455                 460

Phe Pro Gly Pro Met Gly Arg Thr Gln Gly Trp Asn Leu Gly Ser Gly
465                 470                 475                 480

Val Asn Arg Ala Ser Val Ser Ala Phe Ala Thr Thr Asn Arg Met Glu
                485                 490                 495

Leu Glu Gly Ala Ser Tyr Gln Val Pro Pro Gln Pro Asn Gly Met Thr
            500                 505                 510

Asn Asn Leu Gln Gly Ser Asn Thr Tyr Ala Leu Glu Asn Thr Met Ile
        515                 520                 525

Phe Asn Ser Gln Pro Ala Asn Pro Gly Thr Thr Ala Thr Tyr Leu Glu
    530                 535                 540

Gly Asn Met Leu Ile Thr Ser Glu Ser Glu Thr Gln Pro Val Asn Arg
545                 550                 555                 560

Val Ala Tyr Asn Val Gly Gly Gln Met Ala Thr Asn Asn Gln Ser Ser
                565                 570                 575

Thr Thr Ala Pro Ala Thr Gly Thr Tyr Asn Leu Gln Glu Ile Val Pro
            580                 585                 590

Gly Ser Val Trp Met Glu Arg Asp Val Tyr Leu Gln Gly Pro Ile Trp
        595                 600                 605

Ala Lys Ile Pro Glu Thr Gly Ala His Phe His Pro Ser Pro Ala Met
    610                 615                 620

Gly Gly Phe Gly Leu Lys His Pro Pro Met Met Leu Ile Lys Asn
625                 630                 635                 640

Thr Pro Val Pro Gly Asn Ile Thr Ser Phe Ser Asp Val Pro Val Ser
                645                 650                 655

Ser Phe Ile Thr Gln Tyr Ser Thr Gly Gln Val Thr Val Glu Met Glu
            660                 665                 670

Trp Glu Leu Lys Lys Glu Asn Ser Lys Arg Trp Asn Pro Glu Ile Gln
        675                 680                 685

Tyr Thr Asn Asn Tyr Asn Asp Pro Gln Phe Val Asp Phe Ala Pro Asp
    690                 695                 700

Ser Thr Gly Glu Tyr Arg Thr Thr Arg Pro Ile Gly Thr Arg Tyr Leu
705                 710                 715                 720

Thr Arg Pro Leu

<210> SEQ ID NO 6
<211> LENGTH: 738
<212> TYPE: PRT
<213> ORGANISM: Artificial Sequence
<220> FEATURE:
<223> OTHER INFORMATION: Adeno-associated virus rh.10 vp1 capsid protein
```

```
<400> SEQUENCE: 6

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Lys Lys Arg Leu Asn Phe Gly Gln
                165                 170                 175

Thr Gly Asp Ser Glu Ser Val Pro Asp Pro Gln Pro Ile Gly Glu Pro
            180                 185                 190

Pro Ala Gly Pro Ser Gly Leu Gly Ser Gly Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Asn Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
    370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
                405                 410                 415
```

```
Gln Phe Glu Asp Val Pro Phe His Ser Ser Tyr Ala His Ser Gln Ser
                420                 425                 430

Leu Asp Arg Leu Met Asn Pro Leu Ile Asp Gln Tyr Leu Tyr Tyr Leu
            435                 440                 445

Ser Arg Thr Gln Ser Thr Gly Gly Thr Ala Gly Thr Gln Gln Leu Leu
        450                 455                 460

Phe Ser Gln Ala Gly Pro Asn Asn Met Ser Ala Gln Ala Lys Asn Trp
465                 470                 475                 480

Leu Pro Gly Pro Cys Tyr Arg Gln Gln Arg Val Ser Thr Thr Leu Ser
                485                 490                 495

Gln Asn Asn Asn Ser Asn Phe Ala Trp Thr Gly Ala Thr Lys Tyr His
            500                 505                 510

Leu Asn Gly Arg Asp Ser Leu Val Asn Pro Gly Val Ala Met Ala Thr
        515                 520                 525

His Lys Asp Asp Glu Glu Arg Phe Phe Pro Ser Ser Gly Val Leu Met
    530                 535                 540

Phe Gly Lys Gln Gly Ala Gly Lys Asp Asn Val Asp Tyr Ser Ser Val
545                 550                 555                 560

Met Leu Thr Ser Glu Glu Glu Ile Lys Thr Thr Asn Pro Val Ala Thr
                565                 570                 575

Glu Gln Tyr Gly Val Val Ala Asp Asn Leu Gln Gln Gln Asn Ala Ala
            580                 585                 590

Pro Ile Val Gly Ala Val Asn Ser Gln Gly Ala Leu Pro Gly Met Val
        595                 600                 605

Trp Gln Asn Arg Asp Val Tyr Leu Gln Gly Pro Ile Trp Ala Lys Ile
    610                 615                 620

Pro His Thr Asp Gly Asn Phe His Pro Ser Pro Leu Met Gly Gly Phe
625                 630                 635                 640

Gly Leu Lys His Pro Pro Gln Ile Leu Ile Lys Asn Thr Pro Val
                645                 650                 655

Pro Ala Asp Pro Pro Thr Thr Phe Ser Gln Ala Lys Leu Ala Ser Phe
            660                 665                 670

Ile Thr Gln Tyr Ser Thr Gly Gln Val Ser Val Glu Ile Glu Trp Glu
        675                 680                 685

Leu Gln Lys Glu Asn Ser Lys Arg Trp Asn Pro Glu Ile Gln Tyr Thr
    690                 695                 700

Ser Asn Tyr Tyr Lys Ser Thr Asn Val Asp Phe Ala Val Asn Thr Asp
705                 710                 715                 720

Gly Thr Tyr Ser Glu Pro Arg Pro Ile Gly Thr Arg Tyr Leu Thr Arg
                725                 730                 735

Asn Leu

<210> SEQ ID NO 7
<211> LENGTH: 738
<212> TYPE: PRT
<213> ORGANISM: Artificial Sequence
<220> FEATURE:
<223> OTHER INFORMATION: Adeno-associated virus hu.37 vp1 capsid protein

<400> SEQUENCE: 7

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30
```

```
Lys Ala Asn Gln Gln Lys Gln Asp Asp Gly Arg Gly Leu Val Leu Pro
             35                  40                  45

Gly Tyr Lys Tyr Leu Gly Pro Phe Asn Gly Leu Asp Lys Gly Glu Pro
 50                  55                  60

Val Asn Ala Ala Asp Ala Ala Leu Glu His Asp Lys Ala Tyr Asp
 65              70                  75                  80

Gln Gln Leu Lys Ala Gly Asp Asn Pro Tyr Leu Arg Tyr Asn His Ala
                 85                  90                  95

Asp Ala Glu Phe Gln Glu Arg Leu Gln Glu Asp Thr Ser Phe Gly Gly
                100                 105                 110

Asn Leu Gly Arg Ala Val Phe Gln Ala Lys Lys Arg Val Leu Glu Pro
                115                 120                 125

Leu Gly Leu Val Glu Glu Ala Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Lys Lys Arg Leu Asn Phe Gly Gln
                165                 170                 175

Thr Gly Asp Ser Glu Ser Val Pro Asp Pro Gln Pro Ile Gly Glu Pro
                180                 185                 190

Pro Ala Gly Pro Ser Gly Leu Gly Ser Gly Thr Met Ala Ala Gly Gly
    195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
                260                 265                 270

Asn Thr Tyr Phe Gly Tyr Ser Thr Pro Trp Gly Tyr Phe Asp Phe Asn
                275                 280                 285

Arg Phe His Cys His Phe Ser Pro Arg Asp Trp Gln Arg Leu Ile Asn
                290                 295                 300

Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
                340                 345                 350

Leu Pro Tyr Val Leu Gly Ser Ala His Gln Gly Cys Leu Pro Pro Phe
                355                 360                 365

Pro Ala Asp Val Phe Met Ile Pro Gln Tyr Gly Tyr Leu Thr Leu Asn
                370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
                405                 410                 415

Thr Phe Glu Asp Val Pro Phe His Ser Ser Tyr Ala His Ser Gln Ser
                420                 425                 430

Leu Asp Arg Leu Met Asn Pro Leu Ile Asp Gln Tyr Leu Tyr Tyr Leu
                435                 440                 445
```

```
Ser Arg Thr Gln Ser Thr Gly Gly Thr Gln Gly Thr Gln Gln Leu Leu
    450                 455                 460

Phe Ser Gln Ala Gly Pro Ala Asn Met Ser Ala Gln Ala Lys Asn Trp
465                 470                 475                 480

Leu Pro Gly Pro Cys Tyr Arg Gln Gln Arg Val Ser Thr Thr Leu Ser
                485                 490                 495

Gln Asn Asn Asn Ser Asn Phe Ala Trp Thr Gly Ala Thr Lys Tyr His
                500                 505                 510

Leu Asn Gly Arg Asp Ser Leu Val Asn Pro Gly Val Ala Met Ala Thr
            515                 520                 525

His Lys Asp Asp Glu Glu Arg Phe Phe Pro Ser Ser Gly Val Leu Met
    530                 535                 540

Phe Gly Lys Gln Gly Ala Gly Arg Asp Asn Val Asp Tyr Ser Ser Val
545                 550                 555                 560

Met Leu Thr Ser Glu Glu Glu Ile Lys Thr Thr Asn Pro Val Ala Thr
                565                 570                 575

Glu Gln Tyr Gly Val Val Ala Asp Asn Leu Gln Gln Thr Asn Thr Gly
                580                 585                 590

Pro Ile Val Gly Asn Val Asn Ser Gln Gly Ala Leu Pro Gly Met Val
            595                 600                 605

Trp Gln Asn Arg Asp Val Tyr Leu Gln Gly Pro Ile Trp Ala Lys Ile
    610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                645                 650                 655

Pro Ala Asp Pro Pro Thr Thr Phe Ser Gln Ala Lys Leu Ala Ser Phe
                660                 665                 670

Ile Thr Gln Tyr Ser Thr Gly Gln Val Ser Val Glu Ile Glu Trp Glu
            675                 680                 685

Leu Gln Lys Glu Asn Ser Lys Arg Trp Asn Pro Glu Ile Gln Tyr Thr
    690                 695                 700

Ser Asn Tyr Tyr Lys Ser Thr Asn Val Asp Phe Ala Val Asn Thr Glu
705                 710                 715                 720

Gly Thr Tyr Ser Glu Pro Arg Pro Ile Gly Thr Arg Tyr Leu Thr Arg
                725                 730                 735

Asn Leu

<210> SEQ ID NO 8
<211> LENGTH: 738
<212> TYPE: PRT
<213> ORGANISM: Artificial Sequence
<220> FEATURE:
<223> OTHER INFORMATION: Adeno-associated virus 8 vp1 capsid protein

<400> SEQUENCE: 8

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60
```

```
Val Asn Ala Ala Asp Ala Ala Leu Glu His Asp Lys Ala Tyr Asp
 65                  70                  75                  80

Gln Gln Leu Gln Ala Gly Asp Asn Pro Tyr Leu Arg Tyr Asn His Ala
             85                  90                  95

Asp Ala Glu Phe Gln Glu Arg Leu Gln Glu Asp Thr Ser Phe Gly Gly
        100                 105                 110

Asn Leu Gly Arg Ala Val Phe Gln Ala Lys Lys Arg Val Leu Glu Pro
    115                 120                 125

Leu Gly Leu Val Glu Glu Gly Ala Lys Thr Ala Pro Gly Lys Lys Arg
130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Gly Val Gly Pro Asn Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ala Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
    370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Gln Phe Thr Tyr
                405                 410                 415

Thr Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Thr Thr Gly Gly Thr Ala Asn Thr Gln Thr Leu Gly
    450                 455                 460

Phe Ser Gln Gly Gly Pro Asn Thr Met Ala Asn Gln Ala Lys Asn Trp
465                 470                 475                 480
```

Leu Pro Gly Pro Cys Tyr Arg Gln Gln Arg Val Ser Thr Thr Thr Gly
                485                 490                 495

Gln Asn Asn Asn Ser Asn Phe Ala Trp Thr Ala Gly Lys Tyr His
            500                 505                 510

Leu Asn Gly Arg Asn Ser Leu Ala Asn Pro Gly Ile Ala Met Ala Thr
            515                 520                 525

His Lys Asp Asp Glu Glu Arg Phe Phe Pro Ser Asn Gly Ile Leu Ile
        530                 535                 540

Phe Gly Lys Gln Asn Ala Ala Arg Asp Asn Ala Asp Tyr Ser Asp Val
545                 550                 555                 560

Met Leu Thr Ser Glu Glu Ile Lys Thr Thr Asn Pro Val Ala Thr
                565                 570                 575

Glu Glu Tyr Gly Ile Val Ala Asp Asn Leu Gln Gln Gln Asn Thr Ala
                580                 585                 590

Pro Gln Ile Gly Thr Val Asn Ser Gln Gly Ala Leu Pro Gly Met Val
            595                 600                 605

Trp Gln Asn Arg Asp Val Tyr Leu Gln Gly Pro Ile Trp Ala Lys Ile
    610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                645                 650                 655

Pro Ala Asp Pro Pro Thr Thr Phe Asn Gln Ser Lys Leu Asn Ser Phe
                660                 665                 670

Ile Thr Gln Tyr Ser Thr Gly Gln Val Ser Val Glu Ile Glu Trp Glu
            675                 680                 685

Leu Gln Lys Glu Asn Ser Lys Arg Trp Asn Pro Glu Ile Gln Tyr Thr
        690                 695                 700

Ser Asn Tyr Tyr Lys Ser Thr Ser Val Asp Phe Ala Val Asn Thr Glu
705                 710                 715                 720

Gly Val Tyr Ser Glu Pro Arg Pro Ile Gly Thr Arg Tyr Leu Thr Arg
                725                 730                 735

Asn Leu

<210> SEQ ID NO 9
<211> LENGTH: 738
<212> TYPE: PRT
<213> ORGANISM: Artificial Sequence
<220> FEATURE:
<223> OTHER INFORMATION: Adeno-associated virus rh.64R1 vp1 capsid
      protein

<400> SEQUENCE: 9

Met Ala Ala Asp Gly Tyr Leu Pro Asp Trp Leu Glu Asp Asn Leu Ser
1                   5                   10                  15

Glu Gly Ile Arg Glu Trp Trp Asp Leu Lys Pro Gly Ala Pro Lys Pro
                20                  25                  30

Lys Ala Asn Gln Gln Lys Gln Asp Asp Gly Arg Gly Leu Val Leu Pro
            35                  40                  45

Gly Tyr Lys Tyr Leu Gly Pro Phe Asn Gly Leu Asp Lys Gly Glu Pro
        50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

```
Asp Ala Glu Phe Gln Glu Arg Leu Gln Glu Asp Thr Ser Phe Gly Gly
                100                 105                 110

Asn Leu Gly Arg Ala Val Phe Gln Ala Lys Lys Arg Val Leu Glu Pro
            115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Ile Gly Glu Pro
            180                 185                 190

Pro Ala Ala Pro Ser Ser Val Gly Ser Gly Thr Met Ala Ala Gly Gly
    195                 200                 205

Gly Ala Pro Met Ala Asp Asn Asn Glu Gly Ala Asp Gly Val Gly Ser
210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
    370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Ser Phe Ser Tyr
                405                 410                 415

Thr Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Ser Thr Gly Gly Thr Ala Gly Thr Gln Gln Leu Leu
    450                 455                 460

Phe Ser Gln Ala Gly Pro Ser Asn Met Ser Ala Gln Ala Arg Asn Trp
465                 470                 475                 480

Leu Pro Gly Pro Cys Tyr Arg Gln Gln Arg Val Ser Thr Thr Leu Ser
                485                 490                 495

Gln Asn Asn Asn Ser Asn Phe Ala Trp Thr Gly Ala Thr Lys Tyr His
            500                 505                 510
```

```
Leu Asn Gly Arg Asp Ser Leu Val Asn Pro Gly Val Ala Met Ala Thr
            515                 520                 525

Asn Lys Asp Asp Glu Asp Arg Phe Phe Pro Ser Ser Gly Ile Leu Met
        530                 535                 540

Phe Gly Lys Gln Gly Ala Gly Lys Asp Asn Val Asp Tyr Ser Asn Val
545                 550                 555                 560

Met Leu Thr Ser Glu Glu Ile Lys Thr Thr Asn Pro Val Ala Thr
                565                 570                 575

Glu Gln Tyr Gly Val Val Ala Asp Asn Leu Gln Gln Asn Thr Ala
                580                 585                 590

Pro Ile Val Gly Ala Val Asn Ser Gln Gly Ala Leu Pro Gly Met Val
        595                 600                 605

Trp Gln Asn Arg Asp Val Tyr Leu Gln Gly Pro Ile Trp Ala Lys Ile
    610                 615                 620

Pro His Thr Asp Gly Asn Phe His Pro Ser Pro Leu Met Gly Gly Phe
625                 630                 635                 640

Gly Leu Lys His Pro Pro Gln Ile Leu Ile Lys Asn Thr Pro Val
                645                 650                 655

Pro Ala Asp Pro Pro Thr Ala Phe Asn Gln Ala Lys Leu Asn Ser Phe
                660                 665                 670

Ile Thr Gln Tyr Ser Thr Gly Gln Val Ser Val Glu Ile Val Trp Glu
            675                 680                 685

Leu Gln Lys Glu Asn Ser Lys Arg Trp Asn Pro Glu Ile Gln Tyr Thr
        690                 695                 700

Ser Asn Tyr Tyr Lys Ser Thr Asn Val Asp Phe Ala Val Asn Thr Glu
705                 710                 715                 720

Gly Val Tyr Ser Glu Pro Arg Pro Ile Gly Thr Arg Tyr Leu Thr Arg
                725                 730                 735

Asn Leu

<210> SEQ ID NO 10
<211> LENGTH: 736
<212> TYPE: PRT
<213> ORGANISM: Artificial Sequence
<220> FEATURE:
<223> OTHER INFORMATION: Adeno-associated virus 9 vp1 capsid protein

<400> SEQUENCE: 10

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125
```

```
Leu Gly Leu Val Glu Glu Ala Ala Lys Thr Ala Pro Gly Lys Lys Arg
        130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525
```

-continued

```
Glu Gly Glu Asp Arg Phe Phe Pro Leu Ser Gly Ser Leu Ile Phe Gly
        530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735
```

<210> SEQ ID NO 11
<211> LENGTH: 52
<212> TYPE: DNA
<213> ORGANISM: Artificial Sequence
<220> FEATURE:
<223> OTHER INFORMATION: Upstream primer for the mutagenesis from NQSKLN
      to SPAKFA

<400> SEQUENCE: 11
atcctccgac cacctccagc cctgccaagt tgcttctttt catcacgcaa ta          52

<210> SEQ ID NO 12
<211> LENGTH: 52
<212> TYPE: DNA
<213> ORGANISM: Artificial Sequence
<220> FEATURE:
<223> OTHER INFORMATION: Downstream primer for the mutagenesis from
      NQSKLN to SPAKFA

<400> SEQUENCE: 12
tattgcgtga tgaaagaagc aaacttggca gggctgaagg tggtcggagg at          52

<210> SEQ ID NO 13
<211> LENGTH: 52
<212> TYPE: DNA
<213> ORGANISM: Artificial Sequence
<220> FEATURE:
<223> OTHER INFORMATION: Upstream primer for the mutagenesis from NQAKLN
      to SPAKFA

<400> SEQUENCE: 13
atcctccaac agcgttcagc cctgccaagt tgcttctttt catcacgcag ta          52

```
<210> SEQ ID NO 14
<211> LENGTH: 52
<212> TYPE: DNA
<213> ORGANISM: Artificial Sequence
<220> FEATURE:
<223> OTHER INFORMATION: Downstream primer for the mutagenesis from
      NQAKLN to SPAKFA

<400> SEQUENCE: 14
tactgcgtga tgaaagaagc aaacttggca gggctgaacg ctgttggagg at          52

<210> SEQ ID NO 15
<211> LENGTH: 52
<212> TYPE: DNA
<213> ORGANISM: Artificial Sequence
<220> FEATURE:
<223> OTHER INFORMATION: Upstream primer for the mutagenesis from NKDKLN
      to SPAKFA

<400> SEQUENCE: 15
atcctccaac ggccttcagc cctgccaagt ttgcttcttt catcacccag ta          52

<210> SEQ ID NO 16
<211> LENGTH: 52
<212> TYPE: DNA
<213> ORGANISM: Artificial Sequence
<220> FEATURE:
<223> OTHER INFORMATION: Downstream primer for the mutagenesis from
      NKDKLN to SPAKFA

<400> SEQUENCE: 16
tactgggtga tgaaagaagc aaacttggca gggctgaagg ccgttggagg at          52

<210> SEQ ID NO 17
<211> LENGTH: 52
<212> TYPE: DNA
<213> ORGANISM: Artificial Sequence
<220> FEATURE:
<223> OTHER INFORMATION: Upstream primer for the mutagenesis from SPAKFA
      to NKDKLN

<400> SEQUENCE: 17
atcctccgac gactttcaac aaggacaagc tgaactcatt tatcactcag ta          52

<210> SEQ ID NO 18
<211> LENGTH: 52
<212> TYPE: DNA
<213> ORGANISM: Artificial Sequence
<220> FEATURE:
<223> OTHER INFORMATION: Downstream primer for the mutagenesis from
      SPAKFA to NKDKLN

<400> SEQUENCE: 18
tactgagtga taaatgagtt cagcttgtcc ttgttgaaag tcgtcggagg at          52

<210> SEQ ID NO 19
<211> LENGTH: 6
<212> TYPE: PRT
<213> ORGANISM: Artificial Sequence
<220> FEATURE:
<223> OTHER INFORMATION: Epitope as NQSKLN

<400> SEQUENCE: 19

Asn Gln Ser Lys Leu Asn
1               5
```

```
<210> SEQ ID NO 20
<211> LENGTH: 6
<212> TYPE: PRT
<213> ORGANISM: Artificial Sequence
<220> FEATURE:
<223> OTHER INFORMATION: Epitope as SPAKFA

<400> SEQUENCE: 20

Ser Pro Ala Lys Phe Ala
1               5

<210> SEQ ID NO 21
<211> LENGTH: 7
<212> TYPE: PRT
<213> ORGANISM: Artificial Sequence
<220> FEATURE:
<223> OTHER INFORMATION: Epitope as SNQAKLN

<400> SEQUENCE: 21

Ser Asn Gln Ala Lys Leu Asn
1               5

<210> SEQ ID NO 22
<211> LENGTH: 6
<212> TYPE: PRT
<213> ORGANISM: Artificial Sequence
<220> FEATURE:
<223> OTHER INFORMATION: Epitope as NKDKLN

<400> SEQUENCE: 22

Asn Lys Asp Lys Leu Asn
1               5
```

SCALABLE PURIFICATION METHOD FOR AAVRH10

CROSS-REFERENCE TO RELATED APPLICATIONS

This is a continuation of U.S. patent application Ser. No. 16/060,404, filed Jun. 7, 2018, which is a National Stage Entry under 35 U.S.C. 371 of International Patent Application No. PCT/US2016/066013, filed Dec. 9, 2016, which claims the benefit of U.S. Provisional Patent Application No. 62/266,347, filed Dec. 11, 2015, and U.S. Provisional Patent Application No. 62/322,055, filed Apr. 13, 2016. These applications are incorporated by reference herein.

BACKGROUND OF THE INVENTION

This invention describes a novel scalable method for producing rAAV suitable for clinical applications.

The use of recombinant adeno-associated viruses (rAAV) for a variety of gene therapy and vaccine approaches have been described. However, even with these approaches, scalable methods for purification of rAAV have been lacking.

Adeno-associated virus (AAV), a member of the Parvovirus family, is a small, non-enveloped virus. AAV particles comprise an AAV capsid composed of 60 capsid protein subunits, VP1, VP2 and VP3, which enclose a single-stranded DNA genome of about 4.7 kilobases (kb). These VP1, VP2 and VP3 proteins are present in a predicted ratio of about 1:1:10, and are arranged in an icosahedral symmetry. Individual particles package only one DNA molecule strand, but this may be either the plus or minus strand. Particles containing either strand are infectious. AAV is assigned to the genus, Dependovirus, because the virus was discovered as a contaminant in purified adenovirus stocks. AAV's life cycle includes a latent phase and an infectious phase. Replication occurs by conversion of the linear single stranded DNA genome to a duplex form, and subsequent amplification, from which progeny single strands are rescued, replicated, and packaged into capsids in the presence of helper functions. The properties of non-pathogenicity, broad host range of infectivity, including non-dividing cells, and integration make AAV an attractive delivery vehicle.

Recombinant AAV particles are produced in permissive (packaging) host cell cultures and co-expression of helper virus AAV rep and AAV cap genes are required, for replication and packaging, the recombinant genome into the viral particle. Genes necessary for genome replication, capsid formation and genome packaging can be expressed from transfected plasmids, integrated into the host cell genome or introduced to the cell by recombinant viruses. Typically, cells are lysed to release rAAV particles and maximize yield of recovered rAAV. However, the cell lysate contains various cellular components such as host cell DNA, host cell proteins, media components, and in some instances, helper virus or helper virus plasmid DNA, which must be separated from the rAAV vector before it is suitable for in vivo use. Recent advances in rAAV production include the use of non-adherent cell suspension processes in stirred tank bioreactors and production conditions whereby rAAV vectors are released into the media or supernatant reducing the concentration of host cellular components present in the production material but still containing appreciable amounts of in-process impurities. See U.S. Pat. No. 6,566,118 and PCT WO 99/11764. Therefore, rAAV particles may be collected from the media and/or cell lysate and further purified.

Certain previously described purification methods for rAAV are not scalable and/or not adaptable to good manufacturing practices, including, e.g., cesium chloride gradient centrifugation and iodixanol gradient separation. See, e.g., M. Potter et al, Molecular Therapy—Methods & Clinical Development (2014), 1: 14034, pp 1-8.

US Patent Publication No. 2005/0024467 reports that rAAV capsid serotypes such as rAAV-1, 4, 5, and 8 bind weakly to anionic resins either as purified virus stock or in the presence of in-process production impurities such as host cell DNA, host cell proteins, serum albumin, media components, and helper virus components. Purification of those capsid serotypes is described as involving anion-exchange chromatography in combination with other purification methods, such as iodixinol density-gradient centrifugation. See, e.g., Zolotukhin et al., Methods 28(2):158-167 (2002) and Kaludov et al., Hum. Gene Therapy 13:1235-1243 (2002); and U.S. Patent Publication No. 2004/0110266 A1. However, those methods are not readily scalable to commercial scale processes.

Other examples of one- or two-step ion-exchange chromatography purification have been reported for rAAV serotypes 1, 2, 4, 5, and 8. [Brument, N, et al. (2002). Mol Ther 6: 678-686; Okada, T, et al. (2009). Hum Gene Ther 20: 1013-1021; Kaludov, N, et al (2002). Hum Gene Ther 13: 1235-1243; Zolotukhin, S, et al. (2002). Methods 28: 158-167; Davidoff, A M, et al. (2004). J Virol Methods 121: 209-215]. More recently, an affinity media incorporating an anti-AAV VHH ligand, a single-domain camelid antibody derivative, was described as being useful to purify serotypes 1, 2, 3, and 5. [Hellstrom, M, et al. (2009) Gene Ther 16: 521-532]. This affinity capture method focuses on purifying rAAV vectors from in-process production components of the cell culture including helper virus, as well as helper virus proteins, cellular proteins, host cell DNA, and media components present in the rAAV production stock. The affinity capture method described for purifying rAAV 1, 2, 3 and 5 particles is designed to purify rAAV from host cell and helper virus contaminants, but not to separate AAV particles from empty AAV capsids lacking packaged genomic sequences. Further, it is not clear from the literature that this separation is desirable. See, e.g., F. Mingozzi et al, Sci Transl med. 2013 Jul. 17: 5(194), avail in PMC 2014 Jul. 14, which suggests it may be desirable to include empty capsids as decoys which can be used to overcome preexisting humoral immunity to AAV can be overcome using capsid decoys. However, other authors have reported increase efficacy in rAAV1 vectors when they were separated from empty AAV1 capsids. See, e.g., M. Urabe et al, Molecular Therapy, 13(4):823-828 (April 2006).

There remains a need for scalable methods for separating pharmacologically active (full) rAAV particles having the desired transgene packaged from rAAV capsids which lack the desired transgene.

SUMMARY OF THE INVENTION

The present invention provides a scalable method for efficiently separating genome-containing AAVrh10 vector particles (full) from genome-deficient rAAVrh10 intermediates (empty capsids). Also provided are purified AAV1 vector particles.

In one aspect, the method for separating full AAVrh10 viral particles from empty AAVrh10 intermediates comprises subjecting a mixture comprising recombinant AAVrh10 viral particles and AAV rh10 vector intermediates/byproducts to fast performance liquid chromatography (FPLC), wherein the AAVrh10 viral particles and AAVrh10 intermediates are bound to a strong anion exchange resin equilibrated at a pH of about 10.0 and subjected to a salt gradient while monitoring the eluate for ultraviolet absorbance at about 260 nm and about 280 nm. The AAVrh10 full capsids are collected from a fraction which is eluted when the ratio of A260/A280 reaches an inflection point. More particularly, the full capsids are collected from the eluted fraction(s) characterized by having a higher peak (area under the curve) at an absorbance of 260 nm as compared to the peak (area under the curve) at an absorbance of 280 nm. The majority of the fractions observed for the process of the invention have a higher amount of empty capsids (higher peak/area under curve at A280). The absorbance peak at 260 nm being equal to or exceeding the absorbance peak at 280 nm is indicative of the fraction containing the full capsids.

In a further aspect, the sample loaded into the fast protein liquid chromatography (FPLC) method contains full recombinant AAVrh10 viral particles and AAV rh10 intermediates (empty capsids) that had been purified from production system contaminants using affinity capture. In one embodiment, the affinity capture is performed using a high performance affinity resin having an antibody specific for AAV.

In still another aspect, a scalable method is provided for separating full AAVrh10 viral particles from AAVrh10 intermediates by using an anti-AAV antibody based affinity capture resin followed by an anion exchange resin. In one embodiment, the mixture containing the AAVrh10 viral particles and AAVrh10 intermediates is loaded onto the affinity resin in a buffer having a high salt concentrations, e.g., about 400 nM NaCl to about 650 mM NaCl or another salt(s) having an equivalent ionic strength. The wash step for the affinity resin is thereafter performed at an even higher salt concentration, e.g., in the range of about 750 mM to about 1 M NacCl or equivalent. In one embodiment, the AAVrh10 mixture is maintained at a salt concentration of about 400 mM NaCl to about 650 mM NaCl, or equivalent prior to being applied to the anion exchange resin column. In a further embodiment, the rAAVrh10 mixture is maintained at this salt concentration following concentration and prior to loading onto the affinity resin.

In yet another aspect, a method for separating AAVrh10 viral particles from AAVrh10 capsid intermediates is provided, said method comprising: (a) mixing a suspension comprising recombinant AAVrh10 viral particles and AAV rh10 vector intermediates and a Buffer A comprising 20 mM to 50 mM Bis-Tris propane (BTP) and a pH of about 10.0; (b) loading the suspension of (a) onto a strong anion exchange resin column; (c) washing the loaded anion exchange resin with Buffer 1% B which comprises a salt having the ionic strength of 10 mM to 40 mM NaCl and BTP with a pH of about 10.0; (d) applying an increasing salt concentration gradient to the loaded and washed anion exchange resin, wherein the salt gradient is the equivalent of 10 mM to about 40 mM NaCl; and (e) collecting rAAVrh10 particles from the eluate collected at the inflection point, where the rAAVrh10 particles are at least about 90% purified from AAVrh10 intermediates.

In a further aspect, a scalable method is provided for separating pharmacologically active recombinant AAVrh10 viral particles containing DNA genomic sequences from inert genome-deficient (empty) AAVrh10 vector intermediates, said method comprising: (a) forming a loading suspension comprising: recombinant AAVrh10 viral particles and empty AAV rh10 capsid which have been purified to remove contaminants from an AAV producer cell culture in which the particles and intermediates were generated; and a Buffer A comprising 20 mM Bis-Tris propane (BTP) and a pH of about 10.0; (b) loading the suspension of (a) onto a strong anion exchange resin, said resin being in a vessel having an inlet for flow of a suspension and/or solution and an outlet permitting flow of eluate from the vessel; (c) washing the loaded anion exchange resin with Buffer 1% B which comprises 10 mM NaCl and 20 mM BTP with a pH of about 10.0; (d) applying an increasing salt concentration gradient to the loaded and washed anion exchange resin, wherein the salt gradient ranges from 10 mM to about 190 mM NaCl, inclusive of the endpoints, or an equivalent; and (e) collecting the rAAV particles from eluate collected at an inflection point, said rAAV particles being purified away from rh10 intermediates.

In a further aspect, the affinity resin separation comprises: (i) equilibrating the affinity resin with Buffer A1 which comprises about 200 mM to about 600 mM NaCl, about 20 mM Tris-Cl and a neutral pH prior to applying the material to the affinity resin; (ii) washing the loaded resin of (a) with Buffer C1 which comprises about 800 mM NaCl to about 1200 mM NaCl, 20 mM Tris-Cl and a neutral pH; (iii) washing the Buffer C1-washed resin of (b) with Buffer A1 to reduce salt concentration; (iv) washing the affinity resin of (c) with Buffer B which comprises about 200 nM to about 600 nM NaCl, 20 mM Sodium Citrate, pH about 2.4 to about 3; and (v) collecting the eluate of (iv) which comprises the full AAVrh10 particles and the empty AAVrh10 capsid fraction for loading onto the anion exchange resin.

In still another aspect, vector preparations are provided that have less than 5% contamination with AAV intermediates (including AAV empty capsids). In another aspect, vector preparations are provided that have less than 2% contamination with AAV empty capsids, or less than 1% contamination with AAV empty capsids. In a further aspect, AAV compositions are provided which are substantially free of AAV empty capsids.

Still other advantages of the present invention will be apparent from the detailed description of the invention.

BRIEF DESCRIPTION OF THE DRAWINGS

FIGS. 1A to 1H provide separation of rh10 AAV vector particle populations on AEX monolith columns. FIG. 1A is a chromatogram of a CIMmultus™ QA column run. $2 \times 10^{14}$ GC vector particles were loaded to an 8 mL column and eluted with a linear salt gradient (System: Avant 150, load: AVB eluate, load: 2E+14 GC; flowrate: 40 mL/min (133 cm/h); Buffer A: 20 mM BTP ph10; Buffer B: 20 mm BTP, pH 10/1 M NaCl, wash: 2% B; gradient: 20-180 mM NaCl in 60 CV (2.7 mM/CV). A260 (line extending highest at peaks P2-P3 and second highest at peaks P1, P4 and P5), A280 (line extending second highest at peaks P2-P3 and highest at peaks P1, P4 and P5) and conductivity (smooth line extending from y axis and reaching ~227 mAU when the run volume is ~1300 mL) profiles are shown. Absorbance (mAU) is shown on the y-axis and run volume (mL) on the x-axis. The percentage of loaded GC (% GC recovery) detected in each major fraction (load, wash, elute, column strip) is indicated at the bottom of the figure. Several peaks observed in the salt gradient and high salt column strip are labeled P1-P5. FIG. 1B provides an expanded view of the linear gradient portion of the chromatogram showing two major peaks obtained, P1 (empty particles) and P2 (full particles). A260 (line extending highest at peaks P2-P3 and second highest at peak P1), A280 (line extending highest at peaks P1 and second highest at peaks P2-P3) and conductivity (line across peak P2 horizontally) profiles are shown.

Absorbance (mAU) is shown on the y-axis. Run volume (mL) is shown as solid line beneath the x axis while buffer is indicated on the x axis above the run volume. FIG. 1C is a photo of the SDS-PAGE gel showing AAV protein content (VP1, VP2 and VP3); the GC content of each fraction are indicated below the chromatogram. FIG. 1D is a photo of a gel from an SDS PAGE capsid quantification assay, in which the gel was loaded with serial dilutions of an iodixanol gradient-purified "full" standard (WL618) alongside similar dilutions of pooled "full peak" fractions from two Rh10 vector (PD005 and PD008) runs over CIMmultus™ QA columns. FIG. 1E shows the WL618 standard curve with quantified VP3 band volumes plotted against particle (pt) number. FIGS. 1F and 1G provide the pt numbers for PD005 and PD008, respectively, determined by comparison of VP3 peak volumes with the VP3 volumes of the WL618 standard curve. pt: GC ratios and percent empty capsids are derived by comparison of GC loaded and the pt number determined. FIG. 1H is a linear gradient chromatogram of an 8 mL CIMmultus™ QA column run with an increased Rh10 vector load (system: Avant 25, load: AVB eluate; 5.5E_14 GC; flowrate: 10 mL/min (35 cm/h); Buffer A: 20 mM BTP pH10; Buffer B: 20 mM BTP pH 10/1M NaCl; wash 1% B; gradient: 10-180 nM NaCl in 60 CV (2.8 mM/CV). A260 (line extending highest at peaks P2-P3 and second highest at peaks P1 and P5), A280 (line extending second highest at peaks P2-P3 and highest at peaks P1 and P5) and conductivity (line across peak P2 horizontally and reaching maximum after peak P5) profiles are shown. Absorbance (mAU) is shown on the y-axis. Run volume (mL) is shown as solid line beneath the x axis while buffer is indicated on the x axis above the run volume. The major peak elution conductivities (provided with the unit of mS/cm and below the peak identification numbers P1 and P2) and the absorbance maximum (provided with the unit of mAU and below the peak identification number P2) of the major "full peak" are indicated. GC recoveries for the major peaks as well as particle content and empty full ratios are given below the chromatogram.

FIGS. 2A to 2F show the effect of flow rate on rh10 vector elution profiles on CIMmultus™ QA columns. FIG. 2A is a chromatogram of AAVrh10 vector elution from 1 mL CIMmultus QA columns at 0.4 mL/min (16 cm/h), 60 CV, pH10. A260 is the line forming the higher peak at P2, P3 and P4. A280 is the line forming the lower peak at P2 and P3. Programmed conductivity is the lower line passing through P2 and turning vertical. Actual conductivity is the higher line passing through P2 and curving at P5. FIG. 2B is a chromatogram of AAVrh10 vector elution from 1 mL CIMmultus QA columns at 0.9 mL/min (35 cm/h), 60 CV, pH10. A260 is the line forming the higher peak at P2 and P3 and is lower in P1 and P5. A280 is the line forming the higher peak at P1 and P5. Programmed conductivity is the lower line passing through P2 and turning vertical. Actual conductivity is the higher line passing through P2 and curving at P5. FIG. 2C is a chromatogram of AAVrh10 vector elution from 1 mL CIMmultus QA columns at 1.7 mL/min (66 cm/h), 60 CV, pH10. A260 is the line forming the higher peak at P2 and P3. A280 is represented by the line forming the higher peak at P1 and P5. Programmed conductivity is the lower line passing through P2 and turning vertical. Actual conductivity is the higher line passing through P2 and curving at P5. FIG. 2D is a chromatogram of AAVrh10 vector elution from 1 mL CIMmultus QA columns at 3.4 mL/min (133 cm/h), 60 CV, pH10. A260 is represented by the line forming the higher peak at P2 and P3. A280 is represented by the higher line at P1 and P5. All runs were performed with 20 mM Bis-Tris-Propane (BTP) pH10 as the loading buffer (buffer A) and 20 mM BTP pH10-1M NaCl as the column strip buffer (Buffer B). A linear salt gradient from 1-18% Buffer B was used to elute vector. The column was stripped with 100% Buffer B. Absorbance (mAU) is shown on the y-axis and run volume (mL) on the x-axis. Conductivities (mS/cm) and elution positions (% B) of the major peaks (labelled P1-P5) are indicated. FIG. 2E is an overlay of the A280 absorbance profiles generated at different flow rates: (0.4 mL/min (16 cm/h); 0.9 mL/min (35 cm/h), 1.7 mL/min (66 cm/h), 3.4 mL/min (133 cm/h). A280 at 3.4 mL/min (133 cm/h) is represented by the line which is the highest at about 137 mL and is the lowest at the final peak at about 170-172 mL (strip). A280 at 0.9 mL/min (35 cm/h) is represented by the line forming the lower peak at about 137 mL and is the second highest at the strip. A280 at 1.7 mL/min (66 cm/h) is represented by the line forming the slightly higher peak at about 138 mL and is the third highest at the strip. A280 at 0.4 mL/min (16 cm/h) is represented by the lower peak starting slightly beyond 138 mL and forms the highest peak at the strip. FIG. 2F is an expanded view of a column strip peak, more clearly showing the separation, with the A280 peaks from highest to lowest: 0.4 mL/min, 0.9 mL/min; 1.7 mL/min; 3.4 mL/min.

FIGS. 3A-3E shows the effect of pH on rh10 vector elution profiles on CIMmultus™ QA columns. FIG. 3A provides a chromatogram of AAVrh10 vector elution from 1 mL CIMmultus™ QA columns (0.9 mL/min (35 cm/h), 60 CV, pH10). A260 is represented by the line forming the higher peak in P2 and P3. A280 is represented by the line forming the higher peak in P1 and P5. FIG. 3B provides a chromatogram of AAVrh10 vector elution from 1 mL CIMmultus™ QA columns (0.9 mL/min (35 cm/h), 60 CV, pH9.8). A260 is represented by the line forming the higher peak at P2 and P3. A280 is represented by the line forming the higher peak at P1 and P5. FIG. 3C provides a chromatogram of AAVrh10 vector elution from 1 mL CIMmultus™ QA columns (0.9 mL/min (35 cm/h), 60 CV, pH 9.0). FIG. 3D provides a chromatogram of AAVrh10 vector elution from 1 mL CIMmultus™ QA columns (0.9 mL/min (35 cm/h), 60 CV, pH 9.5). A260 is represented by the line forming the higher peak at P2. A280 is represented by the line forming the higher peak at P1 and P5. All runs were performed with 20 mM Bis-Tris-Propane (BTP) pH 9-10 as the loading buffer (buffer A) and 20 mM BTP pH 9-10-1M NaCl as the column strip buffer (Buffer B). A linear salt gradient from 1-18% Buffer B was used to elute vector. The column was stripped with Buffer B. Absorbance (mAU) is shown on the y-axis and run volume on the x-axis. Conductivities (mS/cm) and elution positions (% B) of the major peaks (labelled P1-P5) are indicated. FIG. 3E is an overlay of the A280 absorbance profiles generated at different pH values. The data indicate that each reduction in pH below 10 caused both full and empty particles to bind less strongly to the column and elute earlier in the elution gradient, reducing separation between full and empty capsids.

FIG. 4 provides the vector genome distribution among the AVB column fractions for AAVrh10, AAVhu37, AAVrh64R1, AAV8 and AAV3B. AAV vectors were diluted in binding buffer AVB.A (for AAV3, culture supernatant was buffer-exchanged into the binding buffer) and then loaded onto the AVB column. Fractions from flow through (FT), AVB.A wash (W1), AVB.C wash (W2) and elution (AVB.B) (E) were collected. Vector genome copies were determined by real-time PCR.

DETAILED DESCRIPTION OF THE INVENTION

Figure 1A:
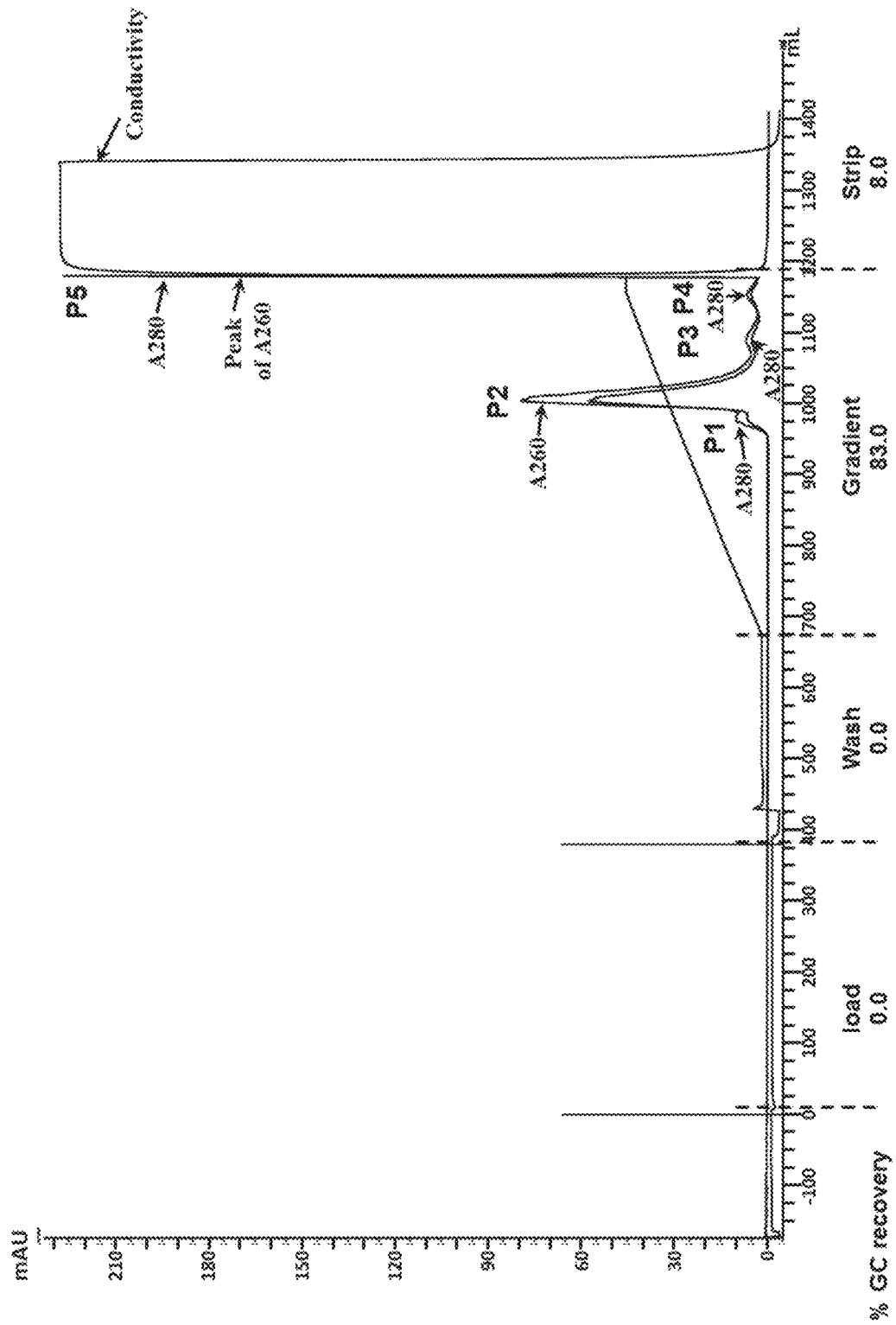

A scalable technology for production of purified rAAVrh10 for use in a variety of gene transfer and/or other applications is described. Suitably, the method purifies rAAVrh10 viral particles from production culture contaminants such as helper virus, helper virus proteins, plasmids, cellular proteins and DNA, media components, serum proteins, AAV rep proteins, unassembled AAV VP1, AAV VP2 and AAV VP3 proteins, and the like. Further, the method provided herein is particularly well suited for separating full rAAVrh10 viral particles from rAAV intermediates. In addition to being useful for AAV1 as defined herein, the method is useful for certain other AAV which share certain required structural with AAVrh10 as described herein.

In one aspect, the method for separating full AAVrh10 viral particles from empty AAVrh10 intermediates comprises subjecting a mixture comprising recombinant AAVrh10 viral particles and AAV rh10 vector intermediates to fast performance liquid chromatography, wherein the AAVrh10 viral particles and AAVrh10 intermediates are bound to a strong anion exchange resin equilibrated at a pH of 9.5 to about 10.2 and subjected to a salt gradient while monitoring eluate for ultraviolet absorbance at about 260 nm and about 280 nm, respectively.

More particularly, the presence of AAVrh10 capsids having genomic sequences packaged therein ("full") and 260/280 absorbance ratios less than 1 is characteristic of AAVrh10 intermediates as defined herein. In general, the production cell culture may yield a mixture of rAAVrh10 "full" and rAAVrh10 "empty" or other intermediates in which 50% or greater are intermediates (including empties), at least 60% are intermediates, or greater than 70% are intermediates. In other embodiments, more or less of the genome copies are "empty"; as a consequence, a corresponding amount of eluted fractions are characterized by having 280 nm peaks (and corresponding larger areas under the curve which are larger than the 260 nm peaks). Fractions characterized by peaks (and corresponding larger areas under the curve) at an absorbence of about 260 nm (A260) that are higher than the corresponding peaks at 260 nm (A260/280 ratio is >1) are highly enriched in full rAAVrh10 particles. The AAVrh10 full capsids are collected from a fraction which is eluted when the peak for A260 crosses over and exceeds the peak for A280 (i.e., reaches an inflection point).

As used herein, "recombinant AAVrh10 viral particle" refers to nuclease-resistant particle (NRP) which has an AAVrh10 capsid, the capsid having packaged therein a heterologous nucleic acid molecule comprising an expression cassette for a desired gene product. Such an expression cassette typically contains an AAV 5' and/or 3' inverted terminal repeat sequence flanking a gene sequence, in which the gene sequence is operably linked to expression control sequences. These and other suitable elements of the expression cassette are described in more detail below and may alternatively be referred to herein as the transgene genomic sequences. This may also be referred to as a "full" AAV capsid. Such a rAAV viral particle is termed "pharmacologically active" when it delivers the transgene to a host cell which is capable of expressing the desired gene product carried by the expression cassette.

In many instances, rAAV particles are referred to as DNase resistant (DRP). However, in addition to this endonuclease (DNase), exonucleases may also be used in the purification steps described herein, to remove contaminating nucleic acids. Such nucleases may be selected to degrade single stranded DNA and/or double-stranded DNA, and RNA. Such steps may contain a single nuclease, or mixtures of nucleases directed to different targets, and may be endonucleases or exonucleases.

The term "nuclease-resistant" indicates that the AAV capsid has fully assembled around the expression cassette which is designed to deliver a transgene to a host cell and protects these packaged genomic sequences from degradation (digestion) during nuclease incubation steps designed to remove contaminating nucleic acids which may be present from the production process.

As used herein, "AAVrh10 capsid" refers to the rh.10 having the amino acid sequence of GenBank, accession: AAO88201, which is incorporated by reference herein and reproduced in SEQ ID NO: 6. So In addition, the methods provided herein can be used to purify other AAV having a capsid highly related to the AAV1 capsid. For example, AAV having about 99% identity to the referenced amino acid sequence in AAO88201 and US 2013/0045186A1 (i.e., less than about 1% variation from the referenced sequence) may be purified using the methods described herein, provided that the integrity of the ligand-binding site for the affinity capture purification is maintained and the change in sequences does not substantially alter the pH range for the capsid for the ion exchange resin purification. For example, AAVhu37, rh.39, rh.20, rh.25, AAV10, bb.1, bb.2 and pi.2 serotypes should bind to the illustrated affinity resin column because their sequence in the antibody-binding region of the commercially available resin is identical or very similar to rh10. Methods of generating the capsid, coding sequences therefore, and methods for production of rAAV viral vectors have been described. See, e.g., Gao, et al, Proc. Natl. Acad. Sci. U.S.A. 100 (10), 6081-6086 (2003) and US 2013/0045186A1.

The term "identity" or "percent sequence identity" may be readily determined for amino acid sequences, over the full-length of a protein, a subunit, or a fragment thereof. Suitably, a fragment is at least about 8 amino acids in length, and may be up to about 700 amino acids. Examples of suitable fragments are described herein. Generally, when referring to "identity", "homology", or "similarity" between two different adeno-associated viruses, "identity", "homology" or "similarity" is determined in reference to "aligned" sequences. "Aligned" sequences or "alignments" refer to multiple nucleic acid sequences or protein (amino acids) sequences, often containing corrections for missing or additional bases or amino acids as compared to a reference sequence. Alignments are performed using a variety of publicly or commercially available Multiple Sequence Alignment Programs. Examples of such programs include, "Clustal W", "CAP Sequence Assembly", "MAP", and "MEME", which are accessible through Web Servers on the internet. Other sources for such programs are known to those of skill in the art. Alternatively, Vector NTI utilities are also used. There are also a number of algorithms known in the art that can be used to measure nucleotide sequence identity, including those contained in the programs described above. As another example, polynucleotide sequences can be compared using Fasta™, a program in GCG Version 6.1. Fasta™ provides alignments and percent sequence identity of the regions of the best overlap between the query and search sequences. For instance, percent sequence identity between nucleic acid sequences can be determined using Fasta™ with its default parameters (a word size of 6 and the NOPAM factor for the scoring matrix) as provided in GCG Version 6.1, herein incorporated by reference. Multiple sequence alignment programs are also available for amino acid sequences, e.g., the "Clustal X", "MAP", "PIMA", "MSA", "BLOCKMAKER", "MEME", and "Match-Box" programs. Generally, any of these programs are used at default settings, although one of skill in the art can alter these settings as needed. Alternatively, one of skill in the art can utilize another algorithm or computer program which provides at least the level of identity or alignment as that provided by the referenced algorithms and programs. See, e.g., J. D. Thomson et al, Nucl. Acids Res., "A comprehensive comparison of multiple sequence alignments", 27(13):2682-2690 (1999).

As used herein the term "AAVrh10 intermediate" or "AAVrh10 vector intermediate" refers to an assembled rAAV capsid which lacks genomic sequences packaged therein. These may also be termed an "empty" capsid. Such a capsid may contain no detectable genomic sequences of an expression cassette, or only partially packaged genomic sequences which are insufficient to achieve expression of the gene product. These empty capsids are non-functional to transfer the gene of interest to a host cell.

In one aspect, a method for separating rAAVrh10 particles having packaged genomic sequences from genome-deficient AAVrh10 intermediates is provided. This method involves subjecting a suspension comprising recombinant AAVrh10 viral particles and AAV rh10 capsid intermediates to fast performance liquid chromatography, wherein the AAVrh10 viral particles and AAVrh10 intermediates are bound to a strong anion exchange resin equilibrated at a pH of about 10.0 and subjected to a salt gradient while monitoring eluate for ultraviolet absorbance at about 260 and about 280. Although less optimal for rAAVrh10, the pH may be as low as 9.8 or as high as 10.2. In this method, the AAVrh10 full capsids are collected from a fraction which is eluted when the ratio of A260/A280 reaches an inflection point.

Fast protein liquid chromatography (FPLC), is a form of liquid chromatography that is often used to analyze or purify mixtures of proteins. As in other forms of chromatography, separation is possible because the different components of a mixture have different affinities for two materials, a moving fluid (the "mobile phase") and a porous solid (the stationary phase). In the present method, the mobile phase is an aqueous solution, or "buffer". The buffer flow rate may be controlled by gravity or a pump (e.g., a positive-displacement pump) and can be kept constant or varied. Suitably, the composition of the buffer can be varied by drawing fluids in different proportions from two or more external reservoirs. The stationary phase described herein is a strong anion exchange resin, typically composed of beads. These beads may be packed into a vessel, e.g., a cylindrical glass or plastic column, or another suitable vessel. As provided herein, volumes of the mobile phase are described as "column volumes". These volumes may be extrapolated to other vessel shapes and designs.

The eluate from the anion exchange resin column or other vessel is monitored for ultraviolet absorbance at about 260 nm and 280 nm. As provided herein, "full" AAVrh10 capsids are characterized by having a UV absorbance of about 260 nm, whereas as "empty" capsids are characterized by having a UV absorbance of about 280 nm. Typically, the majority of the eluate fractions contain empty capsids and as the salt gradient progresses, the majority of the eluate is characterized by a curve for A280 exceeding that of A260. By monitoring UV absorbance for when the eluate is characterized by the curve for A260 crossing over the curve for A280 (ratio of A260/A280 greater than 1), one can selectively collect the "full capsids" until such time as the ratio reverts to A280/A260 greater than 1.

In one embodiment, this fraction(s) selectively collected at the inversion point is characterized by having the total collected rAAV contain at least about 90% "full capsids", and preferably, at least 95% "full capsids". In a further embodiment, these fractions may be characterized by having a ratio of "intermediate" to "full" less than 0.75, more preferably 0.5, preferably less than 0.3.

As used herein, an "anion exchange resin" refers to an insoluble matrix or solid support (e.g., beads) capable of having a surface ionization over a pH range of about 1 to about 14. In one embodiment, a strong anion exchange resin is a solid support having a surface coated with quaternized polyethyleneimine. An example of such a strong anionic exchange resin is the solid support of the CIMultus QA™ column. For example, the anion exchange resin may be a quaternary amine ion exchange resin. In a further embodiment, the anion exchange resin comprises trimethylamine and a support matrix comprising poly(glycidyl methacrylate-co-ethylene dimethacrylate). However, other suitable anion exchange resins may be selected. An example of such a strong anionic exchange resin is that of the POROS HQ™ column. The resins for the columns listed above can be obtained from Amersham/Pharmacia (Piscataway, N.J.), PerSeptive Biosystems (Foster City, Calif.), TosoHaas (Montgomeryville, Pa.) and other suppliers.

The anion exchange material may be in the form of a monolith column or a traditional bead-based column. The ion exchange material can be in a column having a capacity of 0 to 0.5 mL column, 1 mL column, and more preferably, at least an 8 mL column, a 10 mL column, a 20 mL column, a 30 mL column, a 50 mL column, a 100 mL column, a 200 mL column, a 300 mL column, a 400 mL column, a 500 mL column, a 600 mL column, a 700 mL column, an 800 mL column, a 900 mL column, a 1000 mL (1 L) column, a 2000 mL (2 L) column, a 10 L column, a 20 L column, a 30 L column, a 40 L column, a 50 L column, a 60 L column, a 70 L column, an 80 L column, a 90 L column, a 100 L column, a 140 L column, or a column with a capacity greater than 140 L as well as any other column with a capacity between the volumes listed above. Alternatively, another vessel type may be used to contain the anion exchange resin solid support.

As shown in the examples, regulation of the loading and flow rate enhances separation of the empty and full capsids. In one embodiment, the sample loading flow rate is less than or equal to the elution flow rate. For example, the loading flow rate may be in the range of about 10 mL/min to about 40 mL/min, about 15 mL/min to about 30 mL/min, or about 20 mL/min to about 25 mL/min, about 10 mL/min, about 20 mL/min, or about 30 cm/hr to about 135 cm/hr, for a 8 mL monolith column. Suitable flow rates may be extrapolated for a non-monolith column.

The specification describes salt concentrations herein with reference to NaCl for convenience. However, it will be understood that another salt of an equivalent ionic strength (e.g., KCl) may be substituted therefor, another salt having a different ionic strength, but its concentration adjusted to an equivalent ionic strength (e.g., NH4AC), or a combination of salts, may be substituted. The formula for ionic strength is well known to those of skill in the art:

$$I = \frac{1}{2}\sum_{i=1}^{n} c_i z_i^2,$$

where $c_i$ is the molar concentration of ion i (M, mol/L), $z_i$ is the charge number of that ion, and the sum is taken over all ions in the solution. For a 1:1 electrolyte such as sodium chloride (NaCl), potassium chloride (KCl), formate ($HCO_2^-$), or acetate ($CH_2CO_2^-$) (e.g., $NH_4Ac$ or NaAc), the ionic strength is equal to the concentration. However, for a sulfate ($SO_4^{2-}$), the ionic strength is four times higher. Thus, where reference is made to a specific concentration of NaCl, or a range of concentrations, one of skill in the art can substitute another salt, or a mixture of suitable salts, adjusted to the appropriate concentration to provide an ionic strength equivalent to that provided for NaCl. As used herein this this may be termed a "salt equivalent", e.g., "NaCl or equivalent". This will be understood to include both a single salt, a mixture of NaCl with other salts, or a mixture of salts which do not include NaCl, but which are compatible with the apparatus and processes (e.g., affinity and/or anion exchange resin processes) described herein.

The novel FPLC strategy provided herein utilizes a strong anion exchange resin complex as described herein. The anion exchange resin binds the rAAVrh10 empty and full capsids are bound by a charge interaction while in buffer A (the running buffer). In one embodiment, the anion exchange resin column in equilibrated using Buffer A which contains about 200 nM NaCl to about 700 nM NaCl, or about 400 mM NaCl to about 650 mM NaCl, or salt equivalent. Suitable buffers may include ions contributed from a variety of sources, such as, e.g., N-methylpiperazine; piperazine; Bis-Tris; Bis-Tris propane; MES, Hepes, BTP or a phosphate buffer N-methyldiethanolamine; 1,3-diaminopropane; ethanolamine; acetic acid and the like. Such buffers are generally used at a neutral pH (e.g., about 6.5 to about 8, preferably, about 7 to about 7.5, or about 7.5). In one embodiment, a Tris buffer component is selected. In one embodiment, Buffer A contains about 20 mM Tris-Cl, about 400 nM NaCl or equivalent, pH 7.5.

The rAAV particles and intermediates become dissociated and returns to solution (suspension) in buffer B (the elution buffer). Buffer B is used to equilibrate the anion exchange resin. As provided herein, Buffer B is preferably at a pH about 10.0 (preferably 10.0). In one embodiment, the buffer contains about 20 mM Bis-Tris Propane (BTP) and about 10 mM NaCl to about 40 nM NaCl (or salt equivalent).

A mixture containing rAAVrh10 empty and full particles may be suspended in about 100% Buffer A and applied to the column (vessel). The rAAVrh10 particles and intermediates bind to the resin while other components are carried out in the buffer. In one embodiment, the total flow rate of the buffer is kept constant; however, the proportion of Buffer B (the "elution" buffer) is gradually increased from 0% to 100% according to a programmed change in concentration (the "gradient").

In one embodiment, at least one nuclease digestion step is performed prior to loading the mixture onto the anion exchange resin, i.e., during the harvest of the rAAV particles and intermediates from the production cell culture. In a further embodiment, a second nuclease digestion step (e.g., Benzonase) is performed prior to loading the mixture onto the anion exchange resin. Suitably, this may be performed during affinity capture. For example, an additional wash step may be incorporated into the affinity method in which the selected nuclease(s) are pre-mixed with a buffer and used in a wash step. Suitably, the buffer is at neutral pH and a relatively low salt concentration, e.g., about 10 to about 100 mM, about 20 mM to about 80 mM, about 30 mM NaCl to about 50 mL, or about 40 mM, based on the ionic strength of NaCl or a salt equivalent to any of the preceding ranges or amounts. In one embodiment, the flow rate for this wash step is performed at a slower rate than the other wash steps to allow for greater exposure of the nuclease to the loaded rAAV particles and intermediates.

In one embodiment, the salt gradient has an ionic strength equivalent to at least about 10 mM NaCl to about 200 mM NaCl or salt equivalent. In another embodiment the salt gradient has an ionic strength equivalent to at least about 40 mM to about 190 mM NaCl, or about 70 nM to about 170 nM NaCl. In one embodiment, the AAVrh10 intermediates are separated from the anion exchange resin when the salt gradient reaches an ionic strength equivalent to about 50 nM NaCl or greater, or about 70 nM NaCl or greater.

At different points during this process, as described herein, the bound rAAVrh10 particles and rAAVrh10 empty intermediates dissociate and appear in the effluent. The effluent passes through two detectors which measure salt concentration (by conductivity) and protein concentration (by absorption of ultraviolet light at a predetermined wavelength). However, other suitable detection means may be used. As each protein is eluted it appears in the effluent as a "peak" in protein concentration and can be collected for further use.

As described herein, the fractions under the 260 nm elution peak containing the rAAVrh10 viral particles ("full") are collected and processed for further use. In one embodiment, the resulting rAAVrh10 preparation or stock contains a ratio of particles to vector genomes of 1. Optionally, the rAAVrh10 viral particles are placed in a suspension having a pH closer to a neutral pH which will be used for long-term storage and/or delivery to patients. Such a pH may be in the range of about 6.5 to about 8, or about 7 to about 7.5.

In one embodiment, particles elute in a pH of about 10.0 and the rAAV particles are at least about 50-90% purified from AAVrh10 intermediates, or a pH of 10.0 and about 90% to about 99% purified from AAVrh10 intermediates. A stock or preparation of rAAVrh10 particles (packaged genomes) is "substantially free" of AAV empty capsids when the rAAVrh10 particles in the stock are at least about 75% to about 100%, at least about 80%, at least about 85%, at least about 90%, at least about 95%, or at least 99% of the rAAVrh10 in the stock and "empty capsids" are less than about 1%, less than about 5%, less than about 10%, less than about 15% of the rAAVrh10 in the stock or preparation.

In a further embodiment, the average yield of rAAV particles from loaded material is at least about 70%. This may be calculated by determining titer (genome copies) in the mixture loaded onto the column and the amount presence in the final elutions. Further, these may be determined based on q-PCR analysis and/or SDS-PAGE techniques such as those described herein (see figure legends) or those which have been described in the art.

For example, to calculate empty and full particle content, VP3 band volumes for a selected sample (e.g., in examples herein an iodixanol gradient-purified preparation where # of GC=# of particles) are plotted against GC particles loaded. The resulting linear equation (y=mx+c) is used to calculate the number of particles in the band volumes of the test article peaks. The number of particles (pt) per 20 µL, loaded is then multiplied by 50 to give particles (pt)/mL. Pt/mL divided by GC/mL gives the ratio of particles to genome copies (pt/GC). Pt/mL-GC/mL gives empty pt/mL. Empty pt/mL divided by pt/mL and ×100 gives the percentage of empty particles.

Generally, methods for assaying for empty capsids and AAV vector particles with packaged genomes have been known in the art. See, e.g., Grimm et al., *Gene Therapy*

(1999) 6:1322-1330; Sommer et al., *Molec. Ther.* (2003) 7:122-128. To test for denatured capsid, the methods include subjecting the treated AAV stock to SDS-polyacrylamide gel electrophoresis, consisting of any gel capable of separating the three capsid proteins, for example, a gradient gel containing 3-8% Tris-acetate in the buffer, then running the gel until sample material is separated, and blotting the gel onto nylon or nitrocellulose membranes, preferably nylon. Anti-AAV capsid antibodies are then used as the primary antibodies that bind to denatured capsid proteins, preferably an anti-AAV capsid monoclonal antibody, most preferably the B1 anti-AAV-2 monoclonal antibody (Wobus et al., *J. Virol.* (2000) 74:9281-9293). A secondary antibody is then used, one that binds to the primary antibody and contains a means for detecting binding with the primary antibody, more preferably an anti-IgG antibody containing a detection molecule covalently bound to it, most preferably a sheep anti-mouse IgG antibody covalently linked to horseradish peroxidase. A method for detecting binding is used to semi-quantitatively determine binding between the primary and secondary antibodies, preferably a detection method capable of detecting radioactive isotope emissions, electromagnetic radiation, or colorimetric changes, most preferably a chemiluminescence detection kit.

For example, for SDS-PAGE, samples from column fractions can be taken and heated in SDS-PAGE loading buffer containing reducing agent (e.g., DTT), and capsid proteins were resolved on pre-cast gradient polyacylamide gels (e.g., Novex). Silver staining may be performed using SilverXpress (Invitrogen, CA) according to the manufacturer's instructions. In one embodiment, the concentration of AAV vector genomes (vg) in column fractions can be measured by quantitative real time PCR (Q-PCR). Samples are diluted and digested with DNase I (or another suitable nuclease) to remove exogenous DNA. After inactivation of the nuclease, the samples are further diluted and amplified using primers and a TaqMan™ fluorogenic probe specific for the DNA sequence between the primers. The number of cycles required to reach a defined level of fluorescence (threshold cycle, Ct) is measured for each sample on an Applied Biosystems Prism 7700 Sequence Detection System. Plasmid DNA containing identical sequences to that contained in the AAV vector is employed to generate a standard curve in the Q-PCR reaction. The cycle threshold (Ct) values obtained from the samples are used to determine vector genome titer by normalizing it to the Ct value of the plasmid standard curve. End-point assays based on the digital PCR can also be used.

In one aspect, an optimized q-PCR method is provided herein which utilizes a broad spectrum serine protease, e.g., proteinase K (such as is commercially available from Qiagen). More particularly, the optimized qPCR genome titer assay is similar to a standard assay, except that after the DNase I digestion, samples are diluted with proteinase K buffer and treated with proteinase K followed by heat inactivation. Suitably samples are diluted with proteinase K buffer in an amount equal to the sample size. The proteinase K buffer may be concentrated to 2 fold or higher. Typically, proteinase K. treatment is about 0.2 mg/mL, but may be varied from 0.1 mg/mL to about 1 mg/mL. The treatment step is generally conducted at about 55° C. for about 15 minutes, but may be performed at a lower temperature (e.g., about 37° C. to about 50° C.) over a longer time period (e.g., about 20 minutes to about 30 minutes), or a higher temperature (e.g., up to about 60° C.) for a shorter time period (e.g., about 5 to 10 minutes). Similarly, heat inactivation is generally at about 95° C. for about 15 minutes, but the temperature may be lowered (e.g., about 70 to about 90° C.) and the time extended (e.g., about 20 minutes to about 30 minutes). Samples are then diluted (e.g., 1000 fold) and subjected to TaqMan analysis as described in the standard assay.

Additionally, or alternatively, droplet digital PCR (ddPCR) may be used. For example, methods for determining single-stranded and self-complementary AAV vector genome titers by ddPCR have been described. See, e.g., M. Lock et al, Hu Gene Therapy Methods, Hum Gene Ther Methods. 2014 April; 25(2):115-25. doi: 10.1089/hgtb.2013, 131. Epub 2014 Feb. 14.

In one embodiment, the mixture which is applied to the anion exchange resin has been purified from contamination with materials present from the production system. Suitably, the mixture comprising the recombinant AAVrh10 viral particles and AAVrh10 intermediates contains less than about 10% contamination from non-AAV viral and cellular proteinaceous and nucleic acid materials, or less than about 5% contaminants, or less than 1% contaminating viral and cellular proteinaceous and nucleic acid materials. Thus, the mixture loaded onto the anion exchange resin is about 95% to about 99% free of contaminants.

As used herein, the term "contaminants" refer to host cell, viral, and other proteinaceous materials which are present in the production culture or are by-products thereof. This term does not include rAAV particles or rAAV intermediates having formed AAV capsids.

In one embodiment, the invention utilizes a two-step chromatography method in which affinity capture is utilized to separate a mixture of recombinant AAVrh10 viral particles and AAV rh10 capsid intermediates from production system contaminants. Advantageously, this processing has been found to allow approximately 3 times to 5 times the amount of starting material (based on the concentration of rAAV genome copies) to be processed using approximately 5 to 10 less resin, as compared to certain prior art approaches (e.g., one prior art approach utilized affinity capture after anion exchange and another utilized multiple, sequential, ion exchange resin columns).

This affinity capture is suitably performed using an antibody-capture affinity resin. In one embodiment, the solid support is a cross-linked 6% agarose matrix having an average particle size of about 34 μm and having an AAV-specific antibody. An example of one such commercially available affinity resin is AVB Sepharose™ high performance affinity resin using an AAV-specific camelid-derived single chain antibody fragment of llama origin which is commercially available from GE Healthcare (AVB Sepharose). The manufacturer's product literature indicates that the product binds AAV 1, 2, 3 and 5, but has no reference to AAVrh10. The manufacturer's literature further recommends up to a 150 cm/h flow rate and a relatively low loading salt concentration. Other suitable affinity resins may be selected or designed which contain an AAV-specific antibody, AAVrh10 specific antibody, or other immunoglobulin construct which is an AAV-specific ligand. Such solid supports may be any suitable polymeric matrix material, e.g., agarose, sepharose, sephadex, amongst others.

Suitable loading amounts may be in the range of about 2 to about $5 \times 10^{15}$ GC, or less, based on the capacity of a 30-mL column. Equivalent amounts may be calculated for other sized columns or other vessels. At this point prior to anion exchange resin separation as described herein, the term "genome copy" refers to the full particles in a mixture of both rAAVrh10 full particles and rAAVrh10 empties/intermediates.

In one embodiment, the mixture is buffer exchanged with the column equilibration/loading buffer. The method described herein utilizes a relatively high salt concentration for loading the column. In one embodiment, the mixture containing the AAVrh10 viral particles and AAVrh10 intermediates is loaded onto the affinity resin in a buffer having a high salt concentrations, e.g., about 400 nM NaCl to about 650 mM NaCl or another salt(s) having an equivalent ionic strength. The wash step for the affinity resin is thereafter performed at an even higher salt concentration, e.g., in the range of about 750 mM to about 1 M NaCl or equivalent. In one embodiment, the AAVrh10 mixture is maintained at a salt concentration of about 400 mM NaCl to about 650 mM NaCl, or equivalent prior to being applied to the anion exchange resin column. In a further embodiment, the rAAVrh10 mixture is maintained at this salt concentration following concentration and prior to loading onto the affinity resin. One example of a suitable buffer is AVB Buffer A, containing about 200 nM to about 600 nM NaCl, or about 400 nM NaCl, or the ionically equivalent of another salt, about 10 mM to about 40 mM Tris-Cl or another buffer, at a neutral pH. The flow rate at loading may be a manufacturer's recommended value, e.g., about 149 cm/hr. A wash step using AVB Buffer C is applied (1 M NaCl or an equivalent salt, 20 mM sodium citrate, neutral pH), followed by a wash with AVB Buffer A, and use of AVB Buffer B for elution. In one embodiment, AVB Buffer B is about 200 nM to about 600 nM NaCl, or about 400 nM NaCl, or the ionically equivalent of another salt, about 10 mM to about 40 mM Tris-Cl, or about 20 nM Tris-Cl or another buffer. In one embodiment, this step is performed at the range recommended by the manufacturer, e.g., a low pH such as, e.g., about 2.5. In one embodiment, about 2 to about 8, or about 5 column volumes of buffer are used for these steps.

In one embodiment, at least one nuclease digestion step is performed prior to loading the mixture onto the anion exchange resin, i.e., during the harvest of the rAAV particles and intermediates from the production cell culture. In a further embodiment, a second nuclease digestion step is performed during affinity capture. For example, an additional wash step may be incorporated into the affinity method in which the selected nuclease(s) are pre-mixed with a buffer and used in a wash step. Suitably, the buffer is at neutral pH and a relatively low salt concentration, e.g., about 20 to about 60 mM, about 30 mM NaCl to about 50 mL, or about 40 mM, based on the ionic strength of NaCl or a salt equivalent to any of the preceding ranges or amounts. In one embodiment, the flow rate for this wash step is performed at a slower rate than the other wash steps to allow for greater exposure of the nuclease to the loaded rAAV particles and intermediates.

A single nuclease, or a mixture of nucleases, may be used in this step. Such nucleases may target single stranded DNA, double-stranded DNA, or RNA. While the working examples illustrate use of a deoxyribonuclease (DNase) (e.g., Benzonase or Turbonuclease), other suitable nucleases are known, many of which are commercially available. Thus, a suitable nuclease or a combination of nucleases, may be selected. Further, the nuclease(s) selected for this step may be the same or different from the nuclease(s) used during the processing preceding the affinity step and which more immediately follows harvest from the cell culture.

In one embodiment, the load for the first affinity chromatography step is obtained following harvest and subsequent processing of cell lysates and/or supernatant of a production cell culture. This processing may involve at least one of the following processes, including, optional lysis, optional collection from supernatant (media), filtrations, clarification, concentration, and buffer exchange.

Numerous methods are known in the art for production of rAAV vectors, including transfection, stable cell line production, and infectious hybrid virus production systems which include Adenovirus-AAV hybrids, herpesvirus-AAV hybrids and baculovirus-AAV hybrids. See, e.g., G Ye, et al, Hu Gene Ther Clin Dev, 25: 212-217 (December 2014); R M Kotin, Hu Mol Genet, 2011, Vol. 20, Rev Issue 1, R2-R6; M. Mietzsch, et al, Hum Gene Therapy, 25: 212-222 (March 2014); T Virag et al, Hu Gene Therapy, 20: 807-817 (August 2009); N. Clement et al, Hum Gene Therapy, 20: 796-806 (August 2009); DL Thomas et al, Hum Gene Ther, 20: 861-870 (August 2009). rAAV production cultures for the production of rAAV virus particles may require; 1) suitable host cells, including, for example, human-derived cell lines such as HeLa, A549, or 293 cells, or insect-derived cell lines such as SF-9, in the case of baculovirus production systems; 2) suitable helper virus function, provided by wild type or mutant adenovirus (such as temperature sensitive adenovirus), herpes virus, baculovirus, or a nucleic acid construct providing helper functions in trans or in cis; 3) functional AAV rep genes, functional cap genes and gene products; 4) a transgene (such as a therapeutic transgene) flanked by AAV ITR sequences; and 5) suitable media and media components to support rAAV production.

A variety of suitable cells and cell lines have been described for use in production of AAV. The cell itself may be selected from any biological organism, including prokaryotic (e.g., bacterial) cells, and eukaryotic cells, including, insect cells, yeast cells and mammalian cells. Particularly desirable host cells are selected from among any mammalian species, including, without limitation, cells such as A549, WEHI, 3T3, 10T1/2, BHK, MDCK, COS 1, COS 7, BSC 1, BSC 40, BMT 10, VERO, WI38, HeLa, a HEK 293 cell (which express functional adenoviral E1), Saos, C2C12, L cells, HT1080, HepG2 and primary fibroblast, hepatocyte and myoblast cells derived from mammals including human, monkey, mouse, rat, rabbit, and hamster. In certain embodiments, the cells are suspension-adapted cells. The selection of the mammalian species providing the cells is not a limitation of this invention; nor is the type of mammalian cell, i.e., fibroblast, hepatocyte, tumor cell, etc.

AAV sequences may be obtained from a variety of sources. For example, a suitable AAV sequence may be obtained as described in WO 2005/033321 or from known sources, e.g., the American Type Culture Collection, or a variety of academic vector core facilities. Alternatively, suitable sequences are synthetically generated using known techniques with reference to published sequences. Examples of suitable AAV sequences are provided herein.

In addition to the expression cassette, the cell contains the sequences which drive expression of an AAV capsid in the cell (cap sequences) and rep sequences of the same source as the source of the AAV ITRs found in the expression cassette, or a cross-complementing source. The AAV cap and rep sequences may be independently selected from different AAV parental sequences and be introduced into the host cell in a suitable manner known to one in the art. While the full-length rep gene may be utilized, it has been found that smaller fragments thereof, i.e., the rep78/68 and the rep52/40 are sufficient to permit replication and packaging of the AAV.

In one embodiment, the host cell contains at least the minimum adenovirus DNA sequences necessary to express an E1a gene product, an E1b gene product, an E2a gene product, and/or an E4 ORF6 gene product. In embodiments in which the host cell carries only E1, the E2a gene product and/or E4 ORF6 gene product may be introduced via helper plasmid or by adenovirus co-infection. In another embodiment, the E2a gene product and/or E4 ORF6 may be substituted by herpesvirus helper functions. The host cell may contain other adenoviral genes such as VAI RNA, but these genes are not required. In one embodiment, the cell used does not carry any adenovirus gene other than E1, E2a and/or E4 ORF6; does not contain any other virus gene which could result in homologous recombination of a contaminating virus during the production of rAAV; and it is capable of infection or transfection by DNA and expresses the transfected gene (s).

One cell type useful in the methods and systems described herein is a host cell stably transformed with the sequences encoding rep and cap, and which is transfected with the adenovirus E1, E2a, and E4ORF6 DNA and a construct carrying the expression cassette as described above. Stable rep and/or cap expressing cell lines, such as B-50 (International Patent Application Publication No. WO 99/15685), or those described in U.S. Pat. No. 5,658,785, may also be similarly employed. Another desirable host cell contains the minimum adenoviral DNA which is sufficient to express E4 ORF6. Yet other cell lines can be constructed using the novel modified cap sequences of the invention.

The preparation of a host cell involves techniques such as assembly of selected DNA sequences. This assembly may be accomplished utilizing conventional techniques. Such techniques include cDNA and genomic cloning, which are well known and are described in Sambrook et al., Molecular Cloning: A Laboratory Manual, Cold Spring Harbor Press, Cold Spring Harbor, N.Y., including polymerase chain reaction, synthetic methods, and any other suitable methods which provide the desired nucleotide sequence.

The required components for AAV production (e.g., adenovirus E1a, E1b, E2a, and/or E4ORF6 gene products, rep or a fragment(s) thereof, cap, the expression cassette, as well as any other desired helper functions), may be delivered to the packaging host cell separately, or in combination, in the form of any genetic element which transfer the sequences carried thereon.

Alternatively, one or more of the components required to be cultured in the host cell to package an expression cassette in an AAV capsid may be provided to the host cell in trans using a suitable genetic element.

Suitable media known in the art may be used for the production of rAAV vectors. These media include, without limitation, media produced by Hyclone Laboratories and JRH including Modified Eagle Medium (MEM), Dulbecco's Modified Eagle Medium (DMEM), custom formulations such as those described in U.S. Pat. No. 6,566,118, and Sf-900 II SFM media as described in U.S. Pat. No. 6,723,551, each of which is incorporated herein by reference in its entirety, particularly with respect to custom media formulations for use in production of recombinant AAV vectors.

rAAV production culture media may be supplemented with serum or serum-derived recombinant proteins at a level of 0.5%-20% (v/v or w/v). Alternatively, as is known in the art, rAAV vectors may be produced in serum-free conditions which may also be referred to as media with no animal-derived products. One of ordinary skill in the art may appreciate that commercial or custom media designed to support production of rAAV vectors may also be supplemented with one or more cell culture components know in the art, including without limitation glucose, vitamins, amino acids, and or growth factors, in order to increase the titer of rAAV in production cultures.

rAAV production cultures can be grown under a variety of conditions (over a wide temperature range, for varying lengths of time, and the like) suitable to the particular host cell being utilized. As is known in the art, rAAV production cultures include attachment-dependent cultures which can be cultured in suitable attachment-dependent vessels such as, for example, roller bottles, hollow fiber filters, microcarriers, and packed-bed or fluidized-bed bioreactors. rAAV vector production cultures may also include suspension-adapted host cells such as HeLa, 293, and SF-9 cells which can be cultured in a variety of ways including, for example, spinner flasks, stirred tank bioreactors, and disposable systems such as the Wave bag system.

rAAV vector particles may be harvested from rAAV production cultures by lysis of the host cells of the production culture or by harvest of the spent media from the production culture, provided the cells are cultured under conditions known in the art to cause release of rAAV particles into the media from intact cells, as described more fully in U.S. Pat. No. 6,566,118).

Suitable methods of lysing cells are also known in the art and include for example multiple freeze/thaw cycles, sonication, microfluidization, and treatment with chemicals, such as detergents and/or proteases.

At harvest, rAAV production cultures may contain one or more of the following: (1) host cell proteins; (2) host cell DNA; (3) plasmid DNA; (4) helper virus; (5) helper virus proteins; (6) helper virus DNA; and (7) media components including, for example, serum proteins, amino acids, transferrins and other low molecular weight proteins.

In some embodiments, the rAAV production culture harvest is clarified to remove host cell debris. In some embodiments, the production culture harvest is clarified by filtration through a series of depth filters including, for example, a grade DOHC Millipore Millistak+HC Pod Filter, a grade A1HC Millipore Millistak+HC Pod Filter, and a 0.2 µm Filter Opticap XL10 Millipore Express SHC Hydrophilic Membrane filter. Clarification can also be achieved by a variety of other standard techniques known in the art, such as, centrifugation or filtration through any cellulose acetate filter of 0.2 µm or greater pore size known in the art. Still other suitable depth filters, e.g., in the range of about 0.045 µm to about 0.2 µm or other filtration techniques may be used.

Suitably, the rAAV production culture harvest is treated with a nuclease, or a combination of nucleases, to digest any contaminating high molecular weight nucleic acid present in the production culture. The examples herein illustrate a DNAse, e.g., Benzonase® digestion performed under standard conditions known in the art. For example, a final concentration of 1 unit/mL to 2.5 units/mL of Benzonase® is used at a temperature ranging from ambient temperature to 37° C. for a period of 30 minutes to several hours, or about 2 hours. In another example, a turbonuclease is used. However, one of skill in the art may utilize other another suitable nuclease, or a mixture of nucleases. Examples of other suitable nuclease is described earlier in this specification.

The mixture containing full rAAV particles and rAAV intermediates (including empty capsids) may be isolated or purified using one or more of the following purification steps: tangential flow filtration (TFF) for concentrating the rAAV particles, heat inactivation of helper virus, rAAV capture by hydrophobic interaction chromatography, buffer exchange by size exclusion chromatography (SEC), and/or nanofiltration. These steps may be used alone, in various combinations, or in different orders. In some embodiments, the method comprises all the steps in the order as described below.

In some embodiments, the Benzonase®-treated mixture is concentrated via tangential flow filtration ("TFF"). Large scale concentration of viruses using TFF ultrafiltration has been described by R. Paul et al., Hu Gene Ther, 4:609-615 (1993). TFF concentration of the feedstream enables a technically manageable volume of feedstream to be subjected to the chromatography steps of the present invention and allows for more reasonable sizing of columns without the need for lengthy recirculation times. In some embodiments, the rAAV feedstream is concentrated between at least two-fold and at least ten-fold. In some embodiments, the feedstream is concentrated between at least ten-fold and at least twenty-fold. In some embodiments, the feedstream is concentrated between at least twenty-fold and at least fifty-fold. One of ordinary skill in the art will also recognize that TFF can also be used at any step in the purification process where it is desirable to exchange buffers before performing the next step in the purification process.

As used herein, the singular form of the articles "a," "an," and "the" includes plural references unless indicated otherwise. For example, the phrase "a virus particle" includes one or more virus particles.

As used herein, the terms "comprise", "comprising", "contain", "containing", and their variants are open claim language, i.e., are permissive of additional elements. In contrast, the terms "consists", "consisting", and its variants are closed claim language, i.e., exclusive additional elements.

Reference to "about" a value or parameter herein includes (and describes) embodiments that are directed to that value or parameter per se. For example, description referring to "about X" includes description of "X." In the context of pH values, "about" refers to a variability of ±0.2 from the given value. For example, "about 10.0" encompasses to 9.8 to 10.2. As to other values, unless otherwise specified "about" refers to a variability of ±10% from a given value. In certain embodiments, the variability may be 1%, 5%, 10%, or values therebetween.

While the purification methods described herein are designed particularly for separating full rAAVrh10 particles from empty rAAVrh10 intermediates, one of skill in the art may apply these techniques to other rAAV which are closely related to AAVrh10, including, e.g., rh39, rh20, rh25, AAV10, bb1, bb2, and pi2, which are described in US 2013/0045186, AAV described in U.S. Pat. No. 7,906,111 (e.g., hu37), derivate of rh10 or other AAV. As described in the examples below, while other AAV are closely related to rAAVrh10, not all of the closely related AAV have the same binding affinity for the resins under the conditions described herein for AAVrh10.

In still another aspect, the invention provides a scalable method for separating full AAVrh10 viral particles from AAVrh10 intermediates by using an anti-AAV antibody based affinity capture resin followed by an anion exchange resin. In one embodiment, the mixture containing the AAVrh10 viral particles and AAVrh10 intermediates is loaded onto the affinity resin in a buffer having a high salt concentrations, e.g., about 400 nM NaCl to about 650 mM NaCl or another salt(s) having an equivalent ionic strength. The wash step for the affinity resin is thereafter performed at an even higher salt concentration, e.g., in the range of about 750 mM to about 1 M NaCl or equivalent. In one embodiment, the AAVrh10 mixture is maintained at a salt concentration of about 400 mM NaCl to about 650 mM NaCl, or equivalent prior to being applied to the anion exchange resin column. In one embodiment, the affinity capture includes a nuclease digestion step. In a further embodiment, the rAAVrh10 mixture is maintained at this salt concentration following concentration and prior to loading onto the affinity resin.

In a further embodiment, the affinity purified mixture containing the viral particles having packaged genomic sequences are separated from genome-deficient AAVrh10 capsid intermediates by subjecting the mixture to fast performance liquid chromatography at a pH of about 10. More particularly, the AAVrh10 viral particles and AAVrh10 intermediates are bound to an anion exchange resin equilibrated at a pH of about 9.8 to about 10 and subjected to a salt gradient while monitoring eluate for ultraviolet absorbance at about 260 and about 280, wherein the AAVrh10 full capsids are collected from a fraction which is eluted when the ratio of A260/A280 reaches an inflection point.

In one aspect, a method for separating AAVrh10 viral particles from AAVrh10 capsid intermediates is provided which involves:
(a) mixing a suspension comprising recombinant AAVrh10 viral particles and AAV rh 10 capsid intermediates and a Buffer A comprising 20 mM to 50 mM Bis-Tris propane (BTP) and a pH of about 10.0;
(b) loading the suspension of (a) onto a strong anion exchange resin column;
(c) washing the loaded anion exchange resin with Buffer 1% B which comprises a salt having the ionic strength of 10 mM to 40 mM NaCl and BTP with a pH of about 10.0;
(d) applying an increasing salt concentration gradient to the loaded and washed anion exchange resin, wherein the salt gradient is the equivalent of about 10 mM to about 400 mM NaCl, or about 10 mM to about 200 mM, or about 10 mM to about 190 mM; and
(e) collecting rAAVrh10 particles from elute obtained at a salt concentration equivalent to at least 70 mM NaCl, where the rAAVrh10 particles are at least about 90% purified from AAVrh10 intermediates.

In one embodiment, the intermediates are eluted from the anion exchange resin when the salt concentration is the equivalent of greater than about 50 mM NaCl. In still a further embodiment, Buffer A is further admixed with NaCl to a final concentration of 1M in order to form or prepare Buffer B. In yet another embodiment, the salt gradient has an ionic strength equivalent to 10 mM to about 190 mM NaCl. In still a further embodiment, the salt gradient has an ionic strength equivalent to 20 mM to about 190 mM NaCl, or about 20 mM to about 170 mM NaCl. The elution gradient may be from 1% buffer B to about 19% Buffer B. Optionally, the vessel containing the anion exchange resin is a monolith column; loading, washing, and eluting in about 60 column volumes.

In still a further embodiment, a method for separating recombinant AAVrh10 viral particles containing DNA comprising genomic sequences from genome-deficient (empty) AAVrh10 capsid intermediates is provided. The method involves:
(a) forming a loading suspension comprising recombinant AAVrh10 viral particles and empty AAV rh10 capsid intermediates which have been purified to remove non-AAV materials from an AAV producer cell culture in which the particles and intermediates were generated; and a Buffer A comprising 20 mM Bis-Tris propane (BTP) and a pH of about 10.0;

(b) loading the suspension of (a) onto a strong anion exchange resin, said resin being in a vessel having an inlet for flow of a suspension and/or solution and an outlet permitting flow of eluate from the vessel;

(c) washing the loaded anion exchange resin with Buffer 1% B which comprises 10 mM NaCl and 20 mM BTP with a pH of about 10.0;

(d) applying an increasing salt concentration gradient to the loaded and washed anion exchange resin, wherein the salt gradient ranges from 10 mM to about 190 mM NaCl, inclusive of the endpoints, or an equivalent; and (e) collecting the rAAV particles from eluate collected following a salt concentration of at least about 70 mM NaCl, or an equivalent salt or ionic strength, said rAAV particles being purified away from rh10 intermediates.

In one embodiment, the pH is 10.0 and the rAAV particles are at least about 90% purified from AAVrh10 intermediates. In a further embodiment, the average yield of rAAV particles is at least about 70%.

In a further embodiment, the rAAVrh10 producer cell culture is selected from a mammalian cell culture, a bacterial cell culture, and an insect cell culture, wherein said producer cells comprise at least (i) nucleic acid sequence encoding an AAVrh10 capsid operably linked to sequences which direct expression of the AAVrh10 capsid in the producer cells; (ii) a nucleic acid sequence comprising AAV inverted terminal repeat sequences and genomic transgene sequences for packaging into the AAV rh10 capsid; and (iii) functional AAV rep sequences operably linked to sequences which direct expression thereof in the producer cells. In another embodiment, producer cells further comprise helper virus sequences required for packaging and replication of the AAVrh10 into a viral particle.

In still another embodiment, the material harvested from the cell culture is applied to an affinity resin to separate contaminants from AAVrh10 viral particles and empty AAVrh10 capsid intermediates.

In a further embodiment, the affinity resin separation comprises:

(i) equilibrating the affinity resin with Buffer A1 which comprises about 200 mM to about 600 mM NaCl, about 20 mM Tris-Cl and a neutral pH prior to applying the material to the affinity resin;

(ii) washing the loaded resin of (a) with Buffer C1 which comprises about 800 mM NaCl to about 1200 mM NaCl, 20 mM Tris-Cl and a neutral pH;

(iii) washing the Buffer C1-washed resin of (b) with Buffer A1 to reduce salt concentration;

(iv) washing the affinity resin of (c) with Buffer B which comprises about 200 nM to about 600 nM NaCl, 20 mM Sodium Citrate, pH about 2.4 to about 3; and (v) collecting the eluate of (iv) which comprises the full AAVrh10 particles and the empty AAVrh10 capsid fraction for loading onto the anion exchange resin.

The following examples are illustrative of methods for producing AAV particles in the supernatant of cell cultures according to the present invention.

EXAMPLES

A two-step chromatography purification scheme is described which selectively captures and isolates the genome-containing AAV vector particles from the clarified, concentrated supernatant of HEK 293 cells five days post transfection. The load for the first chromatography step using AVB Sepharose High Performance affinity resin (GE), consists of the filter-clarified, 10×TFF-concentrated supernatant harvested from ten 36-layer Hyperstack cell culture vessels that have been previously treated at 37° C. with 958,500 units of Benzonase for 2 h followed by a hypertonic shock with 0.5 M NaCl for 2 h. Prior to loading, the bulk harvest is buffer-exchanged with the column equilibration/loading buffer (AVB Buffer A) incubated overnight at 4° C., and then filtered with a 0.2 µm PES depth filter (Sartorius). The sample is applied to a flow-packed, 30-ml AVB column with a bed height of approximately 15 cm using an AKTA Avant 150 liquid chromatography station (GE) and the following method:

Flow rate: 149 cm·hr$^{-1}$ (5 ml/min)
Equilibration: 3 CV AVB Buffer A (400 mM NaCl, 20 mM Tris-Cl, pH 7.5)
Sample Application: approx. 4200 ml
Wash 1: 5 CV AVB Buffer D (1.5 mM MgCl$_2$, 40 mM NaCl, 20 mM Tris-Cl, pH 7.5)
  Premix with 150 µl (37,500 u) Benzonase Nuclease
  Reduce the flow rate to 30 cm·hr$^{-1}$ (5 ml/min)
Wash 2: 5 CV AVB Buffer C (1M NaCl, 20 mM Tris-Cl, pH 7.5)
Wash 3: 3 CV AVB Buffer A
Elution: 2 CV AVB Buffer B (400 mM NaCl, 20 mM Sodium Citrate, pH 2.5)
Re-equilibration: 3 CV Poros-9 Buffer A A volume of 500 µl of AVB Neutralization Buffer (0.01% Pluronic F-68, 0.2 M Bis-Tris propane, pH10.0) is pre-added to the elution fraction tubes and upon completion of the run, the 5-ml fractions under the main 280-nm elution peak (typically three fractions) are pooled and diluted 50× with AEX Buffer A-10.0 (20 mM Bis-Tris Propane pH 10.0) plus Pluronic F-68 (0.001% final) in a polypropylene bottle.

Anion exchange chromatography is subsequently performed to separate the full or DNA-carrying viral particles from the contaminating empty particles in the second step. Specifically, the diluted column eluate from the capture step is applied to a pre-equilibrated CIMmultus QA-8 ml monolith column (BIA Separations) and the following method is run:

Flow rate: 10 ml/min
Equilibration: 20 CV AEX Buffer 1% B (20 mM Bis-Tris Propane pH 10.0, 10 mM NaCl)
Sample Application: approx. 800 ml for three diluted AVB fractions
Wash 1: 10 CV AEX Buffer 1% B-10.0
Elution: 1-19% AEX Buffer B-10.0 (20 mM Bis-Tris Propane pH 10.0, 1 M NaCl)
  Linear gradient in 60 CV @ 20 ml/min
Strip: 20 CV 100% AEX Buffer B-10.0
Re-equilibration: 10 CV AEX Buffer 1% B-10.0

A volume of 370 µl of AEX Neutralization Buffer (0.027% Pluronic F-68, 1M Bis-Tris pH 6.3) is pre-added to the elution tubes to minimize exposure of the vector to the extreme pH after elution. Finally, the 10-ml fractions under the main 260-nm elution peak (about 10) are ultimately pooled and concentrated/diafiltrated with a formulation buffer using a hollow fiber membrane.

Upstream Vector Production

Rh10 AAV vectors are produced by the triple transfection method in HEK293 cells as described previously (Lock et al. 2010, Hum Gene Ther, 21(1): 1259-1271). Media from ten 36-layer Hyperstack cell culture vessels is harvested and treated at 37° C. with Benzonase at 25 U/mL for 2 h followed by a hypertonic shock with 0.5 M NaCl for 2 h. The media is filter-clarified and concentrated 10× by tangential flow filtration (TFF) and then buffer-exchanged using the same apparatus with column equilibration/loading buffer (AVB Buffer A). This "bulk harvest material" is incubated overnight at 4° C. and then filtered with a 0.2 μm PES depth filter (Sartorius).

Example 1—Separation of Full AAVrh10 Particles (Containing Packaged Genomic Sequences) and Empty Capsids Clarified AAVrh10 vector production culture supernatant was loaded to an AVB affinity column (GE) at neutral pH in 400 mM salt and eluted with a low pH (~2.5) buffer. The eluate was immediately adjusted to neutral pH and then diluted 50-fold into a 20 mM Bis-Tris-propane (BTP) at pH 10 (Buffer A). $2\times10^{14}$ vector genome copies (GC) of the affinity purified vector material was loaded onto an 8 mL CIMmultus-QA™ column (Bia Separations) at a flowrate of 40 mL/min (133 cm/h).

The column was washed in Buffer A with 20 mM NaCl, eluted with a shallow (20-180 mM NaCl, 60 column volumes (CV), i.e., 2.7 mM/CV)) salt gradient at the same flow-rate and then stripped with high salt (2%) Buffer B (20 mM BTP, 1M NaCl). A chromatogram of the CIMmultus-QA™ run is shown in FIG. 1A. Fractions representing the load, wash, elution gradient and column strip were combined and assessed for DNase-resistant GC content by qPCR. The majority of the DNase-resistant vector genomes were recovered in the gradient fractions demonstrating the presence of full particles. Five peaks (FIG. 1A; P1-P5) were observed on the chromatogram in the elution gradient and the column strip. The major peak (P2) and a minor peak (P3) had A260 readings which exceeded the A280 readings whereas the A280 reading of P1, P4 and P5 was higher than the A260 reading. Since DNA absorbs at predominantly 260 nm and protein at predominantly 280 nm, the inversion of A260/A280 in these two peak sets suggested the presence of full (genome-containing) and empty (genome-deficient) vector particles, respectively.

Figure 1D:
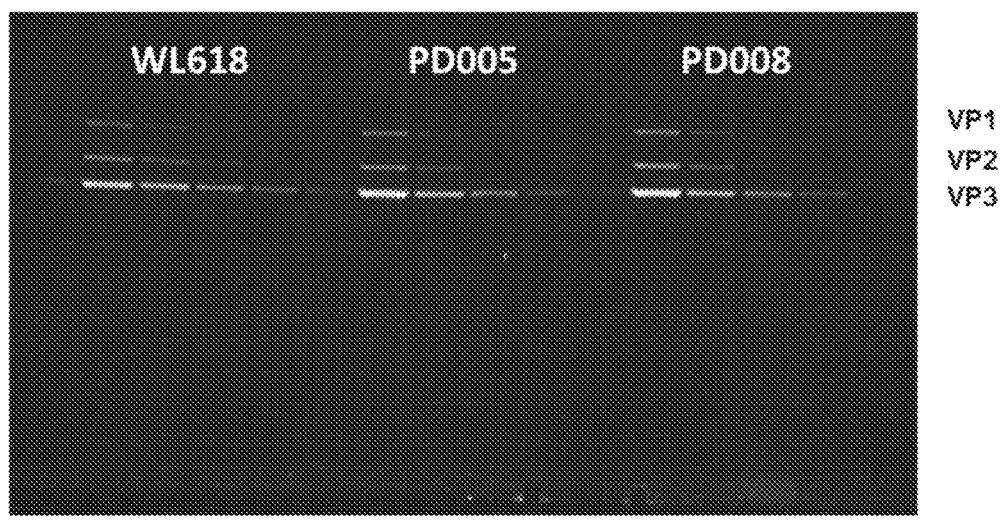
Figure 1E:
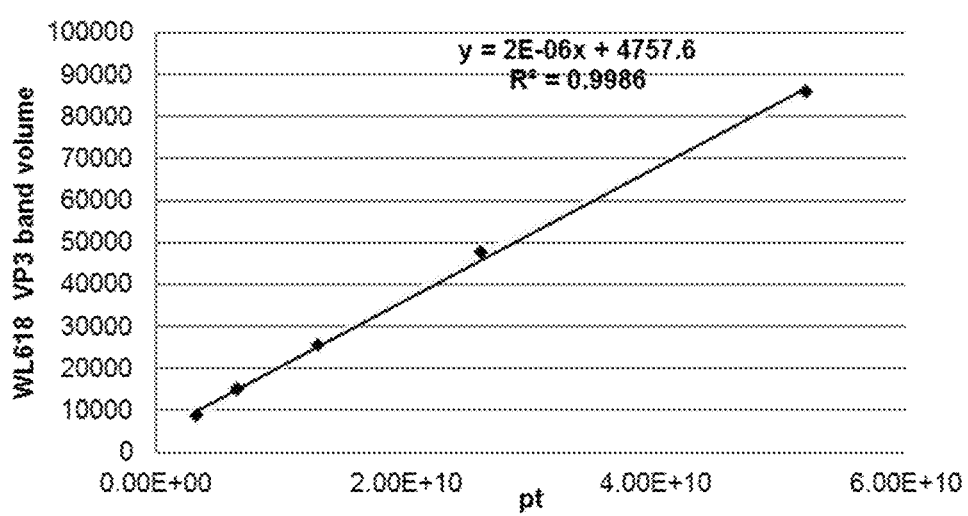

To confirm this finding, individual fractions within P1 and P2 were analyzed both by DNase-resistant GC assay and SDS PAGE (FIGS. 1B-1C). P1 and P2 contained 1.75% and 75% respectively of the vector GC's loaded onto the CIMmultus column; however the total amount of AAV capsid protein observed in the two peaks was similar. These observations confirm that P1 contains mostly empty capsids while P2 contains mostly full capsids. An SDS-PAGE-based method to quantify total capsids was developed (FIG. 1D-F.) and the P2 pooled peak fraction was further analyzed (FIG. 1D, PD005). In this method, a preparation purified by iodixanol gradient purification (FIG. 1D, WL618) and known to contain 100% full capsids was serially diluted and run on an SDS-PAGE gel alongside the similarly diluted P2 pooled peak fraction. The stained gel was scanned and the area under the VP3 capsid protein peaks was determined. In the case of the full reference standard (WL618), the GC number loaded equates to vector particle number and hence a standard curve of particle number versus VP3 peak volume can be plotted (FIG. 1E). The standard curve is used to determine the number of particles in the loaded P2 pooled peak fraction and division of this number with the GC number loaded gives the pt:GC ratio. As shown in FIGS. 1F-1G, for both PD005 and another P2 preparation (PD008) prepared by an identical method, the pt:GC ratios were close to 1 at most dilutions tested, thus further reinforcing the conclusion that the P2 peak contains predominantly full vector capsids.

Example 2—Scalability of Process

Figure 1H:
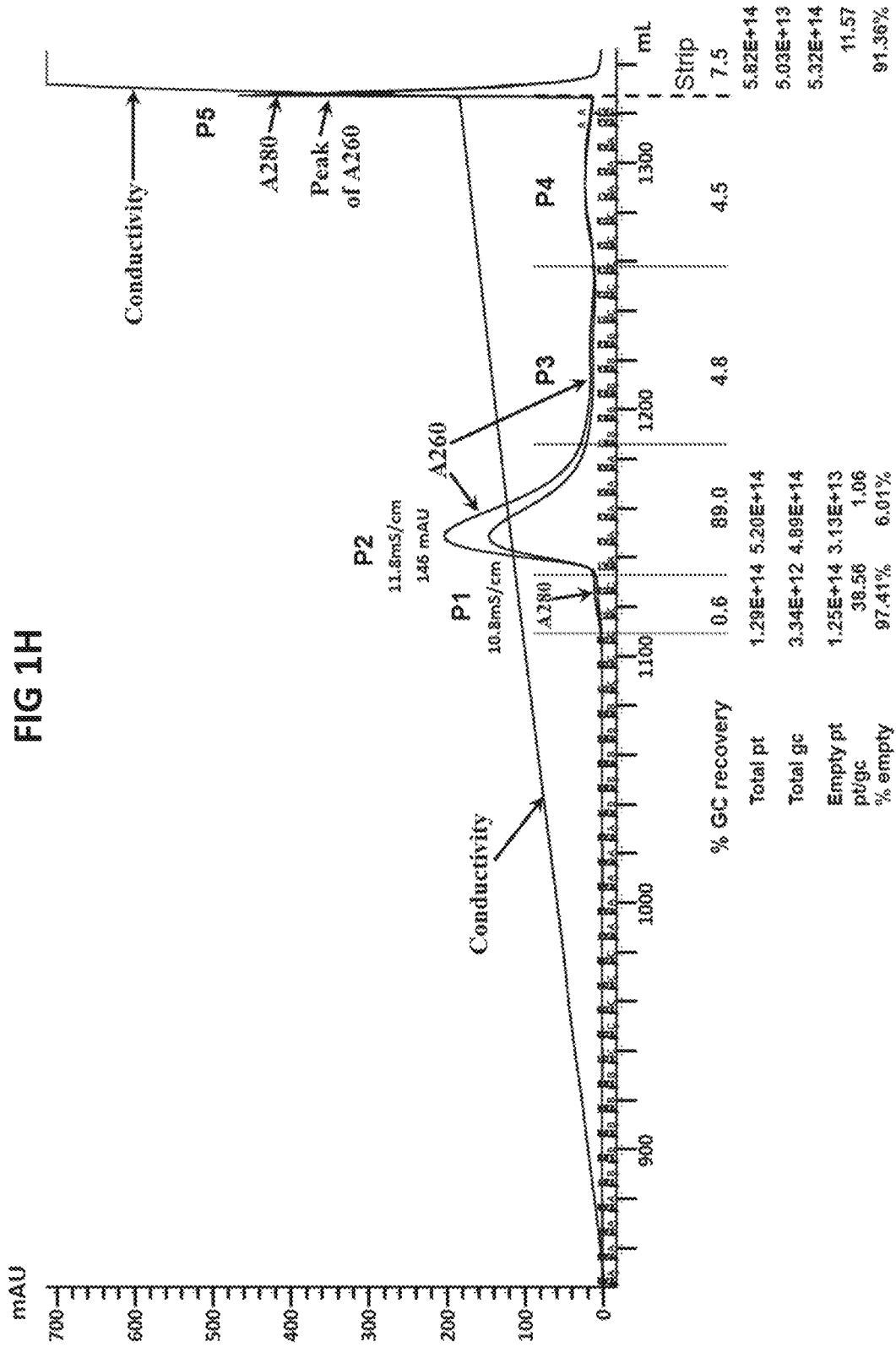

A separate AVB-purified AAVrh10 vector preparation containing $5.5\times10^{14}$ GC was loaded onto an 8 mL CIMmultus-QA™ column under essentially identical conditions except that the flow rate was adjusted to 10 mL/min (wash with 1% Buffer B, gradient 10-180 nM NaCl in 60 CV (2.8 mM/CV)). Despite the increased amount of vector loaded and the reduced flow rate, a similar chromatographic profile was obtained with 5 peaks (P1-P5) detected in the elution gradient and the column strip (FIG. 1H). Analysis of GC content once again showed that the majority of the full particles eluted in P2. These results demonstrate the scalability of the method and the robustness with respect to changes in flow rate. Peaks 1, 2 and 5 were analyzed by the SDS-PAGE particle assay described in Example 1 and the results are provided below the chromatogram. P1 and P2 were once again demonstrated to contain predominantly empty and full particles respectively. Interestingly, the column strip peak (P5) also contained empty particles in similar quantities to the total amount of full particles. This observation supports the conclusion that under the run conditions used, the CIMmultus column is able to separate the major populations of empty (P5) and full (P2) particles by binding the empty particles more strongly such that they are only eluted in the high salt column strip. In addition, the results reveal the existence of at least two different populations of empty particles, those that bind tightly to the column (P5) and those that bind less strongly and elute before the full particles (P1). A third population of empty particles is also suggested by the low A260/A280 ratio of P4 (FIG. 1A) as describe in Example 1. These different particle populations are thought to represent different assembly intermediates of the recombinant AAVrh10 vectors.

Example 3—Effect of Flow Rate on Separation of Full and Empty Capsids

Figure 2B:
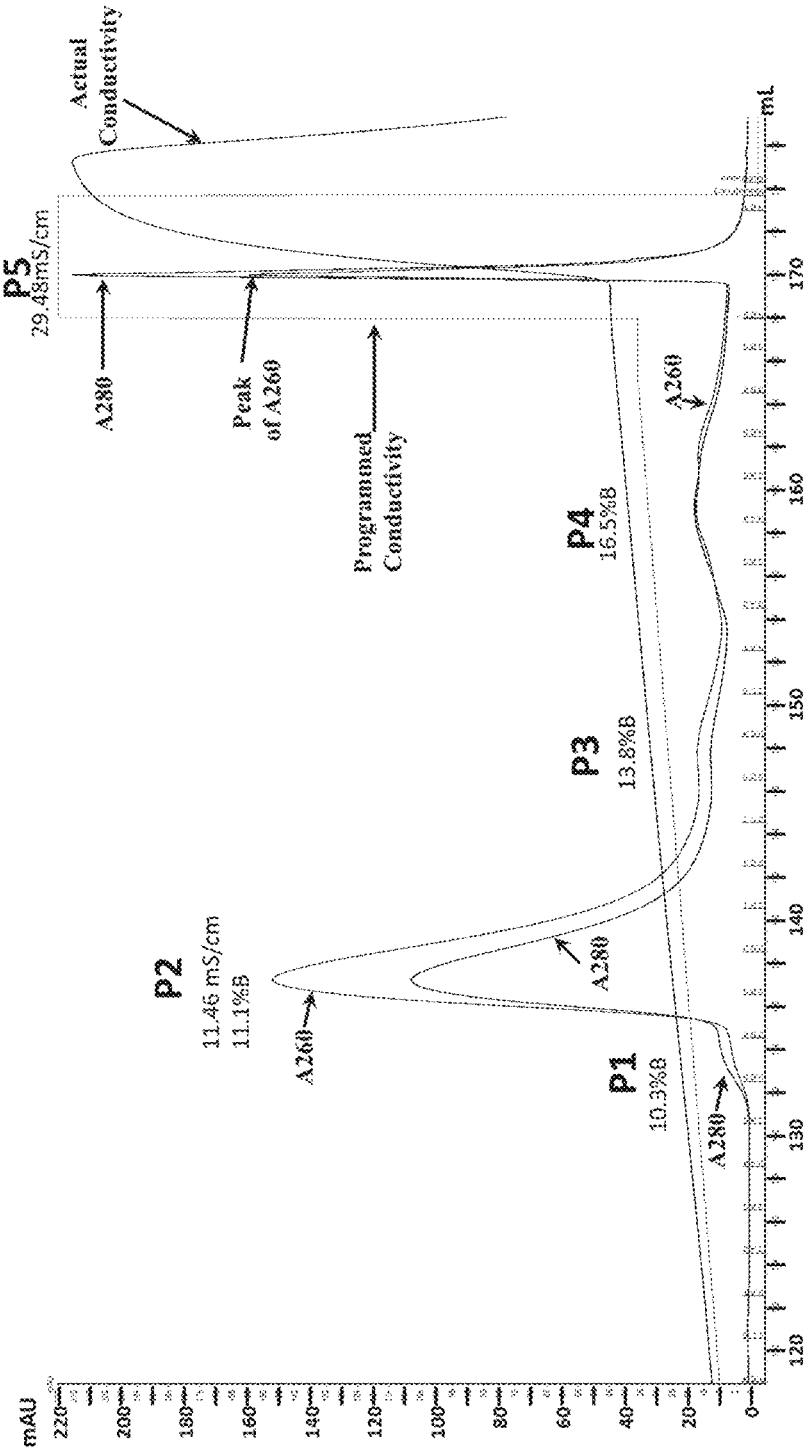

The effect of changes in flow rate on particle separation was investigated at reduced scale on 1 mL CIMmultus-QA columns. $7\times10^{13}$ GC of AVB-purified AAVRh10 vector was loaded per run and flow rates were scaled-down appropriately to the size of the column. The resulting chromatograms from these runs are shown in FIGS. 2A-2D and an overlay of the A280 traces from these runs is shown in FIG. 2E. The same five peaks observed at larger scale were reproduced in the scaled down runs (FIG. 1B, P1-P5) which demonstrates the scalability of the system. With increasing flow rate the size of the empty particle peak obtained in the column strip diminished proportionately indicating weaker binding of this particle population at higher flow rates (FIG. 2E). This effect was accompanied by a slight increase in P1 and P2 peak size with increased flow rates suggesting that the displaced empty particles now elute in the elution gradient. The data indicates that running at optimal flow rates is important for optimal separation of particle populations.

Example 4—pH Effects Changes on Separation of Empty Vs. Full Capsids

The effect of changes in pH on particle separation while maintaining a constant flow rate (0.9 mL/min) was investigated at reduced scale on 1 mL CIMmultus-QA™ columns. $7\times10^{13}$ GC of AVB-purified AAVRh10 vector was loaded per run and the pH of the loading and elution buffers was varied from pH9 to pH10. The resulting chromatograms are shown in FIGS. 3A-3D. The same five peaks observed in previous large scale runs were present in all runs except for the pH9 run where P4 was no longer observed (FIG. 3A-D). Overlaying the A280 traces from the four runs demonstrates a dramatic shift of the P2 full particle peak towards the beginning of the elution gradient with decreasing pH (FIG. 3E). In addition, the size of peaks P5 and P4 were substantially reduced while P2 increased with decreasing pH. The data indicate that each reduction in pH below 10 caused both full and empty particles to bind less strongly to the column and elute earlier in the elution gradient, reducing separation between full and empty capsids.

Example 5—Effect of pH on AAVrh10 Potency

Vector stock from an rAAVrh10 particle having packaged therein an expression cassette having a liver specific promoter and a human transgene for Factor IX and AAV2 5' and 3' ITRs was purified using the two-step affinity capture process and anion exchange resin process described in Examples 1 and 2 at pH 9.5 or pH10.0, following production using conventional techniques. The vector stock was maintained in pH 10.0 or pH 9.5 and assessed for potency at 1 hour, 4 hours, and overnight and then neutralized, with a control being maintained at neutral pH. These data show no difference in potency for these vectors at either of the pH as compared to the controls.

Example 6—Affinity Resin Purification

In one aspect, the process described herein uses sepharose high performance column (e.g., a cross-linked 6% agarose) which utilizes a 14 kD fragment from a single chain llama antibody expressed in yeast (AVB Sepharose™, GE Healthcare) prior to the anion exchange column.

A. Plasmids.

Constructs pAAV2/8, pAAV2/rh.64R1, pAAV2/9 and pAAV2/3B expressing one of the AAV8, rh.64R1, AAV9, and AAV3B capsid protein [SEQ ID NO: 8, 9, 10 and 4, respectively] were used. Mutagenesis of these plasmids was carried out with QuikChange™ Lightning Site-Directed Mutagenesis Kit (Agilent Technologies, CA), following the manual's instructions. The primers for the mutagenesis were: SEQ ID NO: 11: 5'-ATCCTCCGACCA CCTTCAGCCCTGCCAAGTTTGCTTCTTTCATCACG CAATA-3' and SEQ ID NO: 12: 5'-TATTGCGTGAT-GAAAGAAGCAAACTTGGCAGGGCTGAAGGTGG TCGGAGGAT-3' for pAAV2/8 (NQSKLN→SPAKFA, SEQ ID NO: 19 and 20, respectively), SEQ ID NO: 13: 5'-ATCCTCCAACA GCGTTCAGCCCTGCCAAGTTTGCTTCTTTCAT-CACGCAGTA-3' and SEQ ID NO: 14: 5'-TACTGCGTGAT GAAAGAAGCAAACTTGGCAGGGCTGAACGCT GTTGGAGGAT-3' for pAAV2/rh.64R1 (NQAK-LN→SPAKFA, SEQ ID NO: 21 and 20, respectively), SEQ ID NO: 15: 5'-ATCCTCCAAC GGCCTTCAGCCCTGCCAAGTTTGCTTCTTTCATC ACCCAGTA-3' and SEQ ID NO: 16: 5'-TACTGGGTGAT-GAAAGAAGCAAACTTGGCAGGGCTGAAGG CCGTTGGAGGAT-3' for pAAV2/9 (NKDKLN→ SPAKFA, SEQ ID NO: 22 and 20, respectively), SEQ ID NO: 17: 5'-ATCCTCCGACGACTTT-CAACAAGGACAAGCTGAACTCATTTATCACTCA GTA-3' and SEQ ID NO: 18: 5'-TACTGAGTGATAAA-TGAGTTCAGCTTGTCCTTGTTGAAAGTCGTCGGA-GGAT-3' for pAAV2/3B (SPAKFA→NKDKLN, SEQ ID NO: 20 and 22, respectively).

B. Vectors.

Purified vector preparations AAV2/8.CMV.ffluciferase.SV40 AAV2/rh.64R1.CMV.PI.EGFP.WPRE.bGH, AAV2/hu.37.TBG.EGFP.bGH and AAV2/rh.10.CMV.PI.Cre.RBG, were produced and titrated by Penn Vector Core as previously described [Lock, M, et al. (2010). Rapid, Simple, and Versatile Manufacturing of Recombinant Adeno-Associated Viral Vectors at Scale. Human Gene Therapy 21: 1259-1271]. Briefly, one cell stack (Corning, N.Y.) of HEK293 cells was transfected with triple-plasmid cocktail by Polyethylenimine (PEI) when the cell confluency reached around 85%. Culture supernatant was harvested 5 days post transfection and digested with Turbonuclease (Accelagen, CA). NaCl was added to a concentration of 0.5M and the treated supernatant was then concentrated with Tangential Flow Filtration (TFF). Concentration was followed by iodixanol density gradient ultracentrifugation and final formulation by buffer-exchange through Amicon® Ultra-15 (EMD Millipore, MA) into DPBS (Dulbecco's Phosphate-Buffered Saline without calcium and magnesium, 1×, Mediatech, VA) with 35 mM NaCl. Glycerol was added to 5% (v/v) and the vectors were stored at −80° C. until use. For titration, real-time PCR with Taqman reagents (Applied Biosystems, Life Technologies, CA) was performed targeting RBG, bGH and SV40 polyadenylation sequences respectively. AAV2/3B.CB7.CI.ffluciferase.RBG was made the same way, except that at the TFF step, AVB.A buffer (Tris pH 7.5, 20 mM, NaCl 0.4 M) was used for buffer-exchange. The retentate was then stored at 4° C. and 0.22 μm-filtered before application to the AVB column.

For the vectors used for the wild type—SPAKFA mutant comparison, each wild type capsid and its mutants were made in parallel from one 15-cm plate, using a version of the protocol described above but scaled down proportionally according to the culture area of the plate. Culture supernatant was treated with Turbonuclease and then stored at −20° C. Before application to the AVB column, the supernatant was clarified at 47,360×g and 4° C. for 30 minutes followed by 0.22 μm filtration. The transgene cassette for these vectors was CB7.CI.ffluciferase.RBG.

C. Chromatography.

An AKTAFPLC system (GE Healthcare Life Sciences, NJ) was used for all binding studies. The HiTrap column (1 mL) used was prepacked with AVB Sepharose™ High Performance resin (GE Healthcare Life Sciences, NJ). AAV vectors were reconstituted in AVB.A buffer and loaded onto a column equilibrated in the same buffer. The column was washed with 6 mL of AVB.A buffer and 5 mL of AVB.C buffer (Tris pH 7.5, 1 M NaCl) and then eluted with 3 mL of AVB.B buffer (20 mM sodium citrate, pH 2.5, 0.4 M NaCl). The eluted peak fractions were immediately neutralized with 1/10× volume of BTP buffer (0.2 M Bis tris-propane, pH 10). The flow rate was 0.7 mL/min (109 cm/hour). For testing the affinity of AAV vectors for the AVB resin, equal genome copy numbers (GC) of purified AAV8, rh.10 and hu.37 vectors were mixed together before loading. For rh.64R1, the load consisted of an equal amount (GC) of rh.10 and rh.64R1 in AVB.A buffer. For AAV3B, the clarified AAV3B product was loaded directly onto the AVB column.

For the comparison of AAV vectors and their SPAKFA mutants, 9.5 mL of the clarified product was loaded onto the AVB column at 0.7 mL/min, followed by washing with 8 ml of DPBS and 5 ml of AVB.C at 1 mL/min, and then eluted with 4 mL of AVB.B at 0.25 mL/min. The eluate was immediately neutralized as above.

D. In Vitro Infectivity Assay.

Huh7 cells were seeded in 96-well plates at a density of 5e4 cells/well. The cells were then infected with AAV vectors carrying the CB7.CI.ffluciferase.RBG transgene cassette 48 hours after seeding. Three days post-infection, luciferase activity was measured using a Clarity luminometer (BioTek, VT).

E. Sequence Alignment and Structure Analysis.

Sequence alignments were done with the ClustalW algorithm by the AlignX component of Vector NTI Advance 11.0 (Invitrogen, CA). The protein sequences were: AAV1 (accession:NP_049542) [SEQ ID NO:1], AAV2 (accession: YP_680426) [SEQ ID NO:2], AAV3 (accession: NP_043941) [SEQ ID NO:3], AAV3B (accession: AAB95452) [SEQ ID NO:4], AAV5 (accession: YP_068409) [SEQ ID NO:5], rh.10 (accession:AA088201) [SEQ ID NO:6], hu.37 (accession:AAS99285) [SEQ ID NO:7], AAV8 (accession:YP_077180) [SEQ ID NO:8], rh.64R1 (accession:ACB55316) [SEQ ID NO:9], AAV9 (accession:AAS99264) [SEQ ID NO:10], which are incorporated herein by reference. Structure analysis was performed with the Chimera program [Pettersen, E F, et al. (2004). J Comput Chem 25: 1605-1612; Sanner, M F, et al, (1996). Biopolymers 38: 305-320] and the AAV8 capsid structure (PDB: 2QA0) [Nam, H J, et al, (2007). Structure of adeno-associated virus serotype 8, a gene therapy vector. J Virol 81: 12260-12271].

Results

F. The Affinity of AVB Resin for AAV Serotypes Varied Significantly.

To test the affinity of AVB resin for AAV8, rh.64R1 and hu.37 serotypes, AAV vector preparations were mixed together and the rh.10 serotype was added as an internal positive control. This mixing of preparations was performed in order to minimize variations during chromatography. Because of limited choices of real-time PCR probes, two types of vector mixes were made, AAV8+hu.37+rh.10 and rh.64R1+rh.10, and run on the AVB affinity column. The rh.10 vector genome distribution among the different fractions collected was very similar between the two runs (data not shown), so the average of the two runs was used for reporting the rh.10 data. As shown in FIG. 4, 84% of the loaded rh.10 vector genome was present in the elution fraction. The affinity of the hu.37 vector was similar to rh.10, with 82% in the elution fraction. On the contrary, both AAV8 and rh.64R1 vectors bound AVB resin poorly, with only 20% and 22% in the elution fraction, respectively. The affinity of AAV3B for AVB resin was remarkable, with 98% of vector genomes recovered in the elution fraction.

G. Sequence Alignment and Structure Analysis Showed that the Amino Acid Region 665-670 (AAV8 VP1 Numbering) was the Most Diverse Region on the Capsid Surface Between the High AVB-Affinity AAV Serotypes, AAV3B, Rh.10 and Hu.37, and the Low Affinity Serotypes, AAV8 and Rh.64R1.

Among the residues exposed on the surface of the AAV8 capsid (PDB accession number: 2QA0 [Nam, H J, et al, J Virol, 81: 12260-12271 (2007)]), the following twenty six residues are identical between rh.10 and hu.37 serotypes but different from AAV8 (numbering format: AAV8 residue-AAV8 VP1 numbering-rh.10/hu.37 residue): A269S, T453S, N459G, T462Q, G464L, T472N, A474S, N475A, T495L, G496S, A507G, N517D, I542V, N549G, A551G, A555V, D559S, E578Q, I581V, Q594I, I595V, N665S, S667A, N670A, S712N, V722T. Among the 26 residues, only residue 665 (AAV8 VP1 numbering, SEQ ID NO: 8), is identical among AAV1, 2, 3B, AAV5, rh.10 and hu.37. All the poor affinity AAV serotypes (AAV8, rh.64R1 and AAV9) have an Asn residue at this position while the high affinity serotypes have Ser. The 665 residue locates in a small variable patch (665-670, AAV8 VP1 numbering) of the AAV capsid. The entire patch is exposed at the capsid surface, near the pore region and this whole epitope was therefore selected for swapping experiments. Because the affinity of the AAV3B serotype for AVB resin is very good, the SPAKFA epitope from AAV3B was selected to swap into the AAV8, rh.64R1 and AAV9 serotypes using site-specific mutagenesis. The resulting mutants were denoted as AAVx-SPAKFA. As a control, a reverse swap mutant was made where the corresponding epitope of AAV9 (NKDKLN, SEQ ID NO: 22) was swapped into the AAV3B capsid; the resulting mutant was named AAV3B-NKDKLN. The vector production yield of the SPAKFA epitope mutants was 81% (AAV8), 82% (rh.64R1) and 137% (AAV9) of their wild-type counterparts. The yield of AAV3B-NKDKLN was 28% of AAV3B.

H. SPAKFA Epitope Exchange Greatly Improved the AVB-Affinity of AAV8, Rh.64R1 and AAV9 Serotypes.

After SPAKFA substitution, clear improvement in the affinity of AAV8, rh.64R1 and AAV9 serotypes was shown, with the percentage recovery of loaded vector in the elution fraction rising from 30%, 18%, and 0.6% of total fractions to 93%, 91% and 51%, respectively. In contrast, when the NKDKLN epitope of AAV9 was swapped into AAV3B, the elution fraction yield decreased from 98% to 87%, and the fractions of flow-through (FT), wash 1 (W1) and wash 2 (W2), rose from 1.3% to 8.2%, 0.0% to 0.1%, and 0.3% to 4.6% respectively. The majority of AAV3B-NKDKLN was still in the elution fraction however, indicating the existence of other epitope(s) which are involved in binding to AVB resin.

I. The Infectivity of AAV Vectors Containing SPAKFA Substitutions were Unaffected by the SPAKFA Swapping.

One key question was whether the epitope swapping performed impaired the potency of the recipient vector. To address this question, an in vitro infectivity assay was performed with the epitope substitution mutants in Huh7 cells. A range of vector concentrations were used for infection in order to avoid the possible saturation of transduction pathways at high multiplicity of infection (M.O.I.). For AAV3B and AAV3B-NKDKLN, the vector concentration used for infection was 1 log lower than for the other AAV vectors due to the very high infectivity of the AAV3B serotype for Huh7 cells. The infectivity of the SPAKFA mutants was comparable to that of the wild-type AAV vectors. The infectivity of AAV3B-NKDKLN was 59% of AAV3B.

A simple, efficient, generic and easily scalable purification protocol which can be used for all AAV serotypes is highly desirable. Affinity resins such as AVB will likely play an important role in enabling such a process as recently demonstrated in a study by Mietzsch and colleagues, [(2014) Human Gene Therapy 25: 212-222] in which 10 serotypes (AAV1-8, rh.10 and AAV12) were purified in a single step from clarified crude lysate using the AVB resin. However, this example shows that although AAV8, rh.64R1, hu.37, rh.10 and AAV3B can be captured by AVB resin, the affinity of the resin for these different serotypes is very different, with AAV3B having a strong affinity and AAV8 and rh.64R1 binding more poorly. While further optimization of buffers and flow rate can improve binding of AAV8 in our hands (data not shown), conditions and the resulting resin capacity are still not optimal for process scale-up.

The variation in AVB affinity for AAV serotypes rh.10, AAV8, hu.37 and rh.64R1 serotypes was intriguing since they all belong to Clade E and display a high degree of sequence similarity. By contrast, another serotype, AAV5, binds well to AVB but is distantly related to Clade E members. These observations led us to speculate that some subtle sequence differences may play a role in the different binding affinities of these serotypes to AVB. Sequence alignment and structure analysis of the VP3 capsid proteins of these serotypes led us to narrow in on residue 665. At this position, AAV8 and rh.64R1 are asparagine while rh.10, hu.37 and AAV5 are serine. Because the sequence patch around residue 665 is a small variable region, it was decided to swap the whole patch of AAV8, rh.64R1 and AAV9 with the patch (SPAKFA) from AAV3B. The clear improvement in affinity observed following these substitutions indicates that the SPAKFA sequence patch is an epitope of the AVB resin. Importantly, the substitutions did not affect the capsid fitness, in terms of yield and in vitro infectivity.

Another interesting observation was made when the corresponding sequence patch from the AAV9 serotype, NKDKLN, was substituted in place of the SPAKFA epitope in the AAV3B capsid. While the affinity of the AAV3B-NKDKLN vector was apparently weakened, as evidenced by the appearance of the vector in the flow-through fraction, the majority still bound to the column. This result, in conjunction with the fact that substitution of the SPAKFA epitope into AAV9 did not produce the affinity observed with AAV3B, suggests there are other epitopes besides SPAKFA in the AAV3B VP3 amino acid sequence which contribute to AVB binding. One epitope candidate is the region containing residues 328-333. This region is at the outside surface of the pore wall, and is spatially close to the residues 665-670 region. Residue 333 is especially close in spatial terms to the residues 665-670 region and for weak AVB binders such as AAV8, rh.64R1 and AAV9, this residue is Lysine, while in stronger binding serotypes such as AAV3B it is threonine. The hypothesis suggested by these observations is that the regions containing residues 665-670 and 328-333 both contribute to AVB binding, although residues 665-670 make the major contribution. The AVB binding data generated in this study in addition to the AAV3B-NKDLN data described above, support this hypothesis. Serotypes with high SPAKFA homology in the 665-670 region and a threonine residue at position 333 bind best to AVB (AAV3B, AAV1, AAV2 and AAV5). Serotypes with low SPAKFA homology and a lysine residue at position 333 bind poorly (AAV8, rh64R1 and AAV9). Intermediate cases such as serotypes rh10, hu37 and epitope-substituted mutants which contain SPAKFA but have lysine rather than threonine at position 333 (AAV8-SPAKFA and rh64R1-SPAKFA) do bind to AVB resin but less well than serotypes such as AAV3B. Further mutagenic analysis of the 328-333 region and confirmation of its role in AVB binding is complicated because it overlaps the coding sequences for the assembly-activation protein (AAP) in another reading frame [Sonntag, F, et al, (2010), Proc Natl Acad Sci USA, 107: 10220-10225].

The discovery of the SPAKFA-epitope can be useful in predicting whether AVB is a suitable resin for purification of some of the less commonly used AAV serotypes. For example, among the Glade E members, rh.8, rh.43 and rh.46 serotypes have sequences very similar to AAV8 at residues 665-670 and so their affinity for AVB will probably be low. On the other hand, rh.39, rh.20, rh.25, AAV10, bb.1, bb.2 and pi.2 serotypes are likely to bind well because their sequence in this region is identical (or very similar) to rh.10. Similarly, for many clade D members the 665-670 amino acid sequence is TPAKFA and thus these serotypes are likely to display high affinity to AVB, while the rh.69 serotype is likely to bind poorly since the 665-667 amino acid sequence is NQAKLN.

Substitution of the SPAKFA epitope into the capsids of poor-affinity AAV serotypes such as AAV9 would permit for the use of AVB as a universal affinity chromatography resin for all AAV serotypes. In the studies presented here, yields and infectivity of epitope-substituted vectors were unaffected but the impact on tropism was not investigated since it was beyond the scope of this work. However, there are reports which show that the tropism of AAV8 vectors relates mainly to hyper-variable region VII (AAV8 549-564) and IX (AAV8 708-720) [Tenney, R M, et al (2014), Virology 454: 227-236], and/or the subloop 1 (AAV8 435-482) and subloop 4 (AAV8 574-643) [Shen, X, (2007) Molecular Therapy 15: 1955-1962] of the AAV8 capsid. Neutralizing epitope mapping data also supports the notion that the pore structure of AAV capsids and its nearby regions which are responsible for binding to AVB resin are not involved in cell transduction and therefore tropism. Neutralizing epitopes identified so far mainly locate around the 3-fold protrusion of the AAV capsid [Gurda, B L, et al. (2012). Journal of Virology 86: 7739-7751; Adachi, K, et al (2014). Nat Commun 5: 3075; Moskalenko, et al. (2000) Journal of Virology 74: 1761-1766; Wobus, C E, et al (2000). Journal of Virology 74: 9281-9293; Gurda, B L, et al. (2013). Journal of Virology 87: 9111-9124]. Indeed, for AAV2, switching the tip (RGNR) of the 3-fold protrusion resulted in dramatic changes in the tropism of the vector. Another relevant antibody study was performed with monoclonal mouse antibody 3C5 raised against AAV5. This antibody is not neutralizing [Harbison, C E, et al (2012). Journal of General Virology 93: 347-355] and one of its epitopes locates in the 665-670 region [Gurda et al, 2013, cited above]. This observation therefore suggests that antibody binding in this region does not affect cell transduction and by extension, tropism.

The ability to screen for AVB resin binding based upon the primary amino acid sequence, would greatly facilitate the process of selecting suitable AAV. For those serotypes where AVB resin binding is predicted to be poor, the substitution of the SPAKFA epitope may present a viable solution and enable the institution of a universal purification process for multiple serotypes.

(Sequence Listing Free Text)
The following information is provided for sequences containing free text under numeric identifier <223>

| SEQ ID NO: (containing free text) | Free text under <223> |
|---|---|
| 1 | <223> Adeno-associated virus 1 vp1 capsid protein |
| 2 | <223> Adeno-associated virus 2 vp1 capsid protein |
| 3 | <223> Adeno-associated virus 3 vp1 capsid protein |
| 4 | <223> Adeno-associated virus 3B vp1 capsid protein |
| 5 | <223> Adeno-associated virus 5 vp1 capsid protein |
| 6 | <223> Adeno-associated virus rh.10 vp1 capsid protein |
| 7 | <223> Adeno-associated virus hu.37 vp1 capsid protein |
| 8 | <223> Adeno-associated virus 8 vp1 capsid protein |

(Sequence Listing Free Text)
The following information is provided for sequences containing free text under numeric identifier <223>

| SEQ ID NO: (containing free text) | Free text under <223> |
|---|---|
| 9 | <223> Adeno-associated virus rh.64R1 vp1 capsid protein |
| 10 | <223> Adeno-associated virus 9 vp1 capsid protein |
| 11 | <223> Upstream primer for the mutagenesis from NQSKLN to SPAKFA |
| 12 | <223> Downstream primer for the mutagenesis from NQSKLN to SPAKFA |
| 13 | <223> Upstream primer for the mutagenesis from NQAKLN to SPAKFA |
| 14 | <223> Downstream primer for the mutagenesis from NQAKLN to SPAKFA |
| 15 | <223> Upstream primer for the mutagenesis from NKDKLN to SPAKFA |
| 16 | <223> Downstream primer for the mutagenesis from NKDKLN to SPAKFA |
| 17 | <223> Upstream primer for the mutagenesis from SPAKFA to NKDKLN |
| 18 | <223> Downstream primer for the mutagenesis from SPAKFA to NKDKLN |
| 19 | <223> Epitope as NQSKLN |
| 20 | <223> Epitope as SPAKFA |
| 21 | <223> Epitope as SNQAKLN |
| 22 | <223> Epitope as NKDKLN |

All publications and references to GenBank and other sequences cited in this specification are incorporated herein by reference. While the invention has been described with reference to particularly preferred embodiments, it will be appreciated that modifications can be made without departing from the spirit of the invention.

The invention claimed is:

1. A method for separating recombinant adeno-associated virus (AAV) rh10 (rAAVrh10) viral particles having packaged genomic sequences from genome-deficient AAVrh10 capsid intermediates, said method comprising:
   (a) performing filtration through a series of depth filters to afford a clarified rAAVrh10 production culture harvest;
   (b) treating the clarified rAAVrh10 production culture harvest with a nuclease or a combination of nucleases to digest contaminating high molecular weight nucleic acid and to afford a mixture comprising rAAVrh10 viral particles and genome-deficient AAVrh10 capsid intermediates;
   (c) concentrating the nuclease-treated mixture of (b) via tangential flow filtration (TFF) to afford a concentrated rAAVrh10 feedstream;
   (d) contacting the concentrated rAAVrh10 feedstream of (c) comprising the rAAVrh10 viral particles and genome-deficient AAVrh10 capsid intermediates with a high-performance AAVrh10-capsid binding affinity resin to afford purified mixture;
   (e) performing anion exchange chromatography with an anion exchange resin on the affinity purified mixture of (d) containing the rAAVrh10 viral particles at a pH of 9.8 to 10.2;
   (f) monitoring an eluate of (e) for ultraviolet absorbance at 260 nm (A260) and at 280 nm (A280); and
   (g) collecting rAAVrh10 viral particles from fractions eluted when the ratio of A260 to A280 (A260/A280) reaches an inflection point.

2. The method according to claim 1, wherein the inflection point is when the ratio of A260/A280 changes from less than 1 to greater than 1.

3. The method according to claim 1, wherein the rAAVrh10 production culture harvest is from a production cell culture system, wherein the cell culture is selected from a mammalian cell culture, a bacterial cell culture, and an insect cell culture, wherein the production cell culture system comprise at least (i) nucleic acid sequence encoding an AAVrh10 capsid operably linked to sequences which direct expression of the AAVrh10 capsid in the cells; (ii) a nucleic acid sequence comprising AAV inverted terminal repeat sequences and genomic transgene sequences for packaging into the AAVrh10 capsid; and (iii) functional AAV rep sequences operably linked to sequences which direct expression thereof in the cells.

4. The method according to claim 1, wherein the method comprises performing anion exchange chromatography of (e) has a sample loading flow rate less than or equal to the elution flow rate.

5. The method according to claim 1, wherein the anion exchange resin is a quaternary amine strong anion exchange resin.

6. The method according to claim 1, wherein the anion exchange resin is in a column.

7. The method according to claim 6, wherein the affinity capture is performed using a high performance affinity resin.

8. A method for separating recombinant adeno-associated virus (AAV) rh10 (rAAVrh10) viral particles from genome-deficient AAVrh10 capsid intermediates, said method comprising:
   (a) performing filtration through a series of depth filters to afford a clarified rAAVrh10 production culture harvest;
   (b) treating the clarified rAAVrh10 production culture harvest with a nuclease or a combination of nucleases to digest contaminating high molecular weight nucleic acid and to afford a mixture comprising rAAVrh10 viral particles and genome-deficient AAVrh10 capsid intermediates;

(c) contacting the mixture of (b) comprising the rAAVrh10 viral particles and genome-deficient AAVrh10 capsid intermediates with a high-performance AAVrh10-capsid binding affinity resin to afford a purified mixture;

(d) mixing a suspension of the affinity purified mixture of (c) comprising rAAVrh10 viral particles and genome-deficient AAVrh10 capsid intermediates and a first buffer at a neutral pH;

(e) loading the suspension of (d) onto a strong anion exchange resin column comprising quaternary amine string anion exchange resin;

(f) washing the loaded anion exchange resin with a second buffer having a pH of about 10.0 and further comprising a salt in an amount equivalent to 10 mM to 40 mM NaCl or a salt equivalent and Bis-Tris Propane (BTP);

(g) applying an increasing salt concentration gradient to the loaded and washed anion exchange resin, wherein the salt gradient is sufficient to elute the rAAVrh10 viral particles; and (h) collecting rAAVrh10 viral particles which are at least about 90% purified from genome-deficient AAVrh10 capsid intermediates.

9. The method according to claim 8, wherein the rAAVrh10 viral particles and genome-deficient AAV rh10 capsid intermediates of step (c) have been affinity purified at a salt concentration of about 400 mM to 650 mM NaCl or a salt equivalent.

10. The method according to claim 8, wherein the quaternary amine string anion exchange resin column comprises trimethylamine and a support matrix comprising poly(glycidyl methacrylate-co-ethylene dimethacrylate).

11. The method according to claim 8, wherein the salt gradient of (g) is rom about 10 mM to about 190 mM NaCl or a salt equivalent.

12. The method according to claim 8, wherein the vessel is a monolith column and wherein column loading, washing, and elution occur in about 60 column volumes.

13. The method according to a claim 8, wherein the elution in (g) has an elution flow rate which is about 10 mL/min to about 40 mL/min.

14. The method according to claim 13, wherein the elution flow rate is about 20 mL/min.

15. The method according to claim 1, wherein the anion exchange chromatography of (e) is performed with a salt gradient which has an ionic strength equivalent to at least 20 mM to 190 mM NaCl, or a salt gradient having an ionic strength equivalent thereto, and wherein the ionic strength is calculatable using a $$\text{formula } I = \frac{1}{2}\sum\nolimits_{i=1}^{n} c^i z_i^2,$$

where $c_i$ is the molar concentration of ion i (M, mol/L), $z_i$ is the charge number of that ion, and I is taken over all ions in the solution.

16. The method according to claim 1, wherein genome-deficient AAVrh10 capsid intermediates are eluted from the anion exchange resin when a salt gradient reaches an ionic strength equivalent to about 50 mM NaCl or greater, or a salt gradient having an ionic strength equivalent thereto, and wherein the ionic strength is calculatable using a $$\text{formula } I = \frac{1}{2}\sum\nolimits_{i=1}^{n} c^i z_i^2,$$

where $c_i$ is the molar concentration of ion i (M, mol/L), $z_i$ is the charge number of that ion, and I is taken over all ions in the solution.

17. The method according to claim 1, wherein genome deficient AAVrh10 capsid intermediates are eluted from the anion exchange resin when a salt gradient reaches an ionic strength equivalent to about 50 mM KCl or greater, or a salt gradient having an ionic strength equivalent thereto, and wherein the ionic strength is calculatable using a $$\text{formula } I = \frac{1}{2}\sum\nolimits_{i=1}^{n} c^i z_i^2,$$

where ci is the molar concentration of ion i (M, mol/L), $z_i$ is the charge number of that ion, and I is taken over all ions in the solution.

18. The method according to claim 1, wherein the rAAVrh10 viral particles and the genome-deficient AAVrh10 capsid intermediates of step (d) have been affinity purified at a high salt concentration.

19. The method according to claim 1, wherein the series of depth filters of (a) comprise filters of 0.2 μm or greater pore size.

20. The method according to claim 1, wherein the series of depth filters of (a) comprise filters in the range of about 0.045 μm to about 0.2 μm pore size.

21. The method according to claim 1, wherein the anion exchange chromatography of (e) is performed at a pH of about 10.0.

22. The method according to claim 8, wherein the series of depth filters of (a) comprise filters of 0.2 μm or greater pore size.

23. The method according to claim 8, wherein the series of depth filters of (a) comprise filters in the range of about 0.045 μm to about 0.2 μm pore size.

24. The method according to claim 8, wherein the washing buffer of (f) comprising BTP comprises 20 mM to 50 mM BTP.

* * * * *